(12) United States Patent
Ramli et al.

(10) Patent No.: US 7,538,204 B2
(45) Date of Patent: May 26, 2009

(54) RECOMBINANT ENZYME AND USES THEREFOR

(75) Inventors: Umi Salamah Ramli, Selangor (MY); Mohd. Basri Wahid, Selangor (MY); Ravigadevi Sambanthamurthi, Selangor (MY); Cheah Suan Choo, Wilayah Persekutuan (MY); Sharifah Shahrul Rabiah Syed Alwee, Nilai (MY); Siti Nor Akmar Abdullah, Selangor (MY); Ahmad Parveez Ghulam Kadir, Selangor (MY); Abrizah Othman, Selangor (MY); Mohd. Arif Abdul Manaf, Selangor (MY); Omar Abdul Rasid, Putrajaya (MY); Dzulfazly Aminudin, Selangor Darul Ehsan (MY); Abdul Masani Mat Yunus, Selangor (MY)

(73) Assignee: Malaysian Palm Oil Board, Selangor (MY)

( * ) Notice: Subject to any disclaimer, the term of this patent is extended or adjusted under 35 U.S.C. 154(b) by 519 days.

(21) Appl. No.: 11/022,382

(22) Filed: Dec. 23, 2004

(65) Prior Publication Data

US 2006/0026713 A1    Feb. 2, 2006

(30) Foreign Application Priority Data

Jan. 21, 2004    (MY) .............................. PI 20040179

(51) Int. Cl.
*C07H 21/04*    (2006.01)
*C12N 15/00*    (2006.01)
*C12N 1/20*    (2006.01)

(52) U.S. Cl. ................. 536/23.2; 435/320.1; 435/252.3

(58) Field of Classification Search ...................... None
See application file for complete search history.

(56) References Cited

U.S. PATENT DOCUMENTS 5,510,255 A * 4/1996 Knauf et al. ............... 435/91.3

* cited by examiner

*Primary Examiner*—Elizabeth F McElwain
(74) *Attorney, Agent, or Firm*—Knobbe, Martens, Olson & Bear LLP

(57) ABSTRACT

The present invention relates to an isolated nucleic acid molecule comprising a sequence of nucleotides encoding a β-ketoacyl ACP synthase II from a plant, or a variant, derivative, homolog or analog of said β-ketoacyl ACP synthase II. The invention also relates to an isolated β-ketoacyl ACP synthase II enzyme from a plant. The polynucleotide sequences of the present invention may be used inter alia for the generation of cells or plants comprising such cells which have a modified phenotype and/or which exhibit a desired characteristic.

16 Claims, 22 Drawing Sheets

CATTATGCTG AGTGATATCT TTTTTTTTTG CCTTGCTCAC AAGTTATTGC CACATCCTGA
AGGTAGAGGGGTTATCCTTTGTATTGAAAATGCACTAGCAGATGCAGGAG TAGCAAAGGA
AGACATTAATTATGTAAATGCCCATGCAACATCGACGCAGATGGGTGATTTGAAGGAATT
TGAAGCTCTCAACCGCTGTTTTGGTCAGAACCCTCAGCTTAGAGTAAACTCAACAAAGTC
AATGACGGGTCATCTGCTAGGAGCTGCAGGTGGAATAGAAGCTGTGGCTGCTATACAAGC
TATAAGGACTGGTTGGGTCCACCCAAATATCAATTTAGACAACCCGGAGAAAAATGTGGA
TGTCAGCATTCTAGTGGGATCACAAAAAGAGAGATGTGATGTAAAGGTGG CGTTGTCGAA
CTCGTTCGGATTCGGTGGGCATAACTCAA

Figure 1

```
GCCCTTCTCTCGCAGAGAAATAGTGATCCGACTAAAGCGTCACGGCCTTGGGACATTGATCGTGAT
GGATTCGTGATGGGGGAGGGGGCTGGCGTGCTTCTACTGGAAGAATTAGAGCATGCTAAGCAAAG
AGGAGCAAATATCTATGCTGAATTTCTTGGGGGAAGCTTCACATGTGATGCTTACCACATGACTGA
GCCACATCCTGAGGGGGCAGGCATTGCTCTTTGCATTGAGAACGCATTAGCACAAGCAGGGGTAG
CCAAAGAAGATGTTAATTATGTAAATGCTCATGCAACTTCAACACCTGCTGGTGACCTAAAAGAG
TATCAAGCTCTCATTCGTTGTTTTGGGCAGAATCCTGAGCTGAGAGTGAACTCTACAAAATCAATG
ATTGGTCACCTACTAGGAGCTTCTGGTGCGGTGGAAGCTGTTGCTGCAATTCAGGCAATTCGAACA
GGGTGGGTCCATCCAAATGTCAATCTCGAAAACCCAGAAAAAAGTGTGGATATAAATGTGCTGGT
GGGCTCGAAAAAAGGAAAAGGTTGGATGTGATAAGCTGGTGGGCTCAAAGAAGGAAAGATTGGA
TGTGAAGGTGGCCCTGTCAAACTCTTTTGGCTTTGGTGGCCACAACTCGTCTATCCTGTTTGCACCA
TACAAATAAGCATCAGCTATGGGCCTACAAAAGCATCAAGGTCATCTTACATGTAATTTGTATCAG
AAATGACTGTGTGGTGCTTATGTTTTTATTTGGCACCAACATCTTGATCATATGGAATTGGTCTAGA
TGCCGTTATAGCTCATAATAGAATGGTATATAGTGCACTACTTTCAAAAAAAAAAAAAAACTCAG
G
```

Figure 2

```
GCCCTTGGAC ACTGACATGG ACTGAAGGAG TAGAAAATTG CAGGAGAAAT TAATTTTTTT
TCAACAGATG GATTGGTGGC ACCTAAATTA TCTAAACGAA TGGCAAATTC ATGCTCTATT
TACTTATTGC TGGAAAGAAA GCATTAGCCA ATGGTGGGGT TATTGAAGAG GTCATGAGTC
AGCTTGACAA GGCAAAATGC GGAGTGCTCA TAGGCTCTGC GATGGGTGGA ATGAAGGTTT
TTAATGATGC CATCGAAGCT TTAAGGGTCT CATATAAGAA GATGAATCCA TTTTGTGTTC
CATTTGCAAC GACAAACATG GGTTCTGCAA TCCTTGCCAT GGATCTGGGT TGGATGGGCC
CAAATTACTC TATTTCAACT GCTTGTGCTA CAAGCAATTT CTGTATCCTG AATGCAGCAA
ACCATATAAT AAGAGGGGAA GCGGATGTGA TGCTTTGTGG TGGATCAGAT GCTGCTATTA
TACCAATTGG ACTGGGGGGT TTTGTTGCTT GCAGAGCACT CTCGCAGAGA AATAGTGATC
CGACTAAAGC GTCACGGCCT TGGGACATTG ATCGTGATGG ATTCGTGATG GGGGAGGGGG
CTGGCGTGCT TCTACTGGAA GAATTAGAGC ATGCTAAGGG CGAATTCGTT TAAACCTGCA
GGACTAGTCC CTTTAGTGAG GGTTAATTCT GAGCTTGGCG TAGGCAGGTC AACGTTTTAA
CCTC
```

```
              10        20        30        40        50        60
KasU26RC  GCCCTTGGACACTGACATGGACTGAAGGAGTAGAAAATTGCAGGAGAAATTAATTTTTTT
KasU86m   ------------------------------------------------------------

70        80        90       100       110       120
KasU26RC  TCAACAGATGGATTGGTGGCACCTAAATTATCTAAACGAATGGCAAATTCATGCTCTATT
KasU86m   ------------------------------------------------------------

130       140       150       160       170       180
KasU26RC  TACTTATTGCTGGAAAGAAAGCATTAGCCAATGGTGGGGTTATTGAAGAGGTCATGAGTC
KasU86m   ------------------------------------------------------------

190       200       210       220       230       240
KasU26RC  AGCTTGACAAGGCAAAATGCGGAGTGCTCATAGGCTCTGCGATGGGTGGAATGAAGGTTT
KasU86m   ------------------------------------------------------------

250       260       270       280       290       300
KasU26RC  TTAATGATGCCATCGAAGCTTTAAGGGTCTCATATAAGAAGATGAATCCATTTTGTGTTC
KasU86m   ------------------------------------------------------------
```

Figure 4 continued

```
              310       320       330       340       350       360
KasU26RC   CATTTGCAACGACAAACATGGGTTCTGCAATCCTTGCCATGGATCTGGGTTGGATGGGCC

KasU86m    ------------------------------------------------------------

370       380       390       400       410       420
KasU26RC   CAAATTACTCTATTTCAACTGCTTGTGCTACAAGCAATTTCTGTATCCTGAATGCAGCAA

KasU86m    ------------------------------------------------------------

430       440       450       460       470       480
KasU26RC   ACCATATAATAAGAGGGGAAGCGGATGTGATGCTTTGTGGTGGATCAGATGCTGCTATTA

KasU86m    ------------------------------------------------------------

490       500       510       520       530
KasU26RC   TACCAATTGGACTGGGGGGTTTTGTTGCTTGCAGAGCACT----CTCGCAGAGAAATAGTG
                                                  :: ::  ::::::::::::::::
KasU86m    ------------------------------GCCCTTCTCTCGCAGAGAAATAGTG
                                                    10        20

540       550       560       570       580       590
KasU26RC   ATCCGACTAAAGCGTCACGGCCTTGGGACATTGATCGTGATGGATTCGTGATGGGGGAGG
           ::::::::::::::::::::::::::::::::::::::::::::::::::::::::::::
KasU86m    ATCCGACTAAAGCGTCACGGCCTTGGGACATTGATCGTGATGGATTCGTGATGGGGGAGG
              30        40        50        60        70        80

600       610       620       630       640       650
KasU26RC   GGGCTGGCGTGCTTCTACTGGAAGAATTAGAGCATGCTAAGGGCGAATTCGTTTAAACCT
           ::::::::::::::::::::::::::::::::::::::::::     :  ::   ::: :
KasU86m    GGGCTGGCGTGCTTCTACTGGAAGAATTAGAGCATGCTAAG--CAAAGAGGAGCAAATAT
              90       100       110       120       130       140

660       670       680       690       700       710
KasU26RC   GCAGGACTAGTCCCTTTAGTGAGGGTTAAT-TCTGA-GCTTGGCGTAGG-CAGGTCAACG
            :  :    : :   :::  : :: :  :  : :::  ::::  :  : :  : :   ::
KasU86m    CTATGCTGAATTTCTTGGGGGAAGCTTCACATGTGATGCTTACCACATGACTGAGCCACA
              150       160       170       180       190       200

720
KasU26RC   TTTTAACCTC---------------------------------------------------
           : : :
KasU86m    TCCTGAGGGGGCAGGCATTGCTCTTTGCATTGAGAACGCATTAGCACAAGCAGGGGTAGC
              210       220       230       240       250       260

KasU26RC   ------------------------------------------------------------

KasU86m    CAAAGAAGATGTTAATTATGTAAATGCTCATGCAACTTCAACACCTGCTGGTGACCTAAA
              270       280       290       300       310       320

KasU26RC   ------------------------------------------------------------

KasU86m    AGAGTATCAAGCTCTCATTCGTTGTTTTGGGCAGAATCCTGAGCTGAGAGTGAACTCTAC
              330       340       350       360       370       380
```

Figure 4 continued[1]

| KasU26RC | |
|---|---|
| KasU86m | AAAATCAATGATTGGTCACCTACTAGGAGCTTCTGGTGCGGTGGAAGCTGTTGCTGCAAT |
| | 390    400    410    420    430    440 |

| KasU26RC | |
|---|---|
| KasU86m | TCAGGCAATTCGAACAGGGTGGGTCCATCCAAATGTCAATCTCGAAAACCCAGAAAAAAG |
| | 450    460    470    480    490    500 |

| KasU26RC | |
|---|---|
| KasU86m | TGTGGATATAAATGTGCTGGTGGGCTCGAAAAAAGGAAAAGGTTGGATGTGATAAGCTGG |
| | 510    520    530    540    550    560 |

| KasU26RC | |
|---|---|
| KasU86m | TGGGCTCAAAGAAGGAAAGATTGGATGTGAAGGTGGCCCTGTCAAACTCTTTTGGCTTTG |
| | 570    580    590    600    610    620 |

| KasU26RC | |
|---|---|
| KasU86m | GTGGCCACAACTCGTCTATCCTGTTTGCACCATACAAATAAGCATCAGCTATGGGCCTAC |
| | 630    640    650    660    670    680 |

| KasU26RC | |
|---|---|
| KasU86m | AAAAGCATCAAGGTCATCTTACATGTAATTTGTATCAGAAATGACTGTGTGGTGCTTATG |
| | 690    700    710    720    730    740 |

| KasU26RC | |
|---|---|
| KasU86m | TTTTTATTTGGCACCAACATCTTGATCATATGGAATTGGTCTAGATGCCGTTATAGCTCA |
| | 750    760    770    780    790    800 |

| KasU26RC | |
|---|---|
| KasU86m | TAATAGAATGGTATATAGTGCACTACTTTCAAAAAAAAAAAAAAAACTCAGG |
| | 810    820    830    840    850 |

```
CCACTCACAA GGCTGTAAAG AATAAAAAAG TTAGGTTTAA ACTTTAAATC ACCTTTTTAT
ATCTATATCC CCTCTTTNGC AAGTTGGCGA TGGCTTTCGC CACGTCCCCT TGGTTTCGCC
AAAGCTCGTG CCTTTTCTTC CGTAAGATCG ATGCCATCTT TCATTCCCTT CGTCAGCTTT
TCTCCCCTCC CAAAACCTTT CGCCATCCTC TTCGACCCGT TTCCTCCTTC CCAAAATCGC
ATATTTTCTC GTTAAAAATC GCTCTTTTTT CTCTCGCTGT TTCTTAGTCC GCTCTTTGAG
ATCTTGAATC CCTTCTTGGC CTCTTCTCCT CTCTCAACTT CGATCGGAAC GTTCTCGAGT
TCTAGCTTCT GCCCGCTCCG CTTTTGGAGC TTCTCTCCTC CCTTATTCCG GCTTTGCTCT
GTTCTTCTCC AATGGCGGGC GCCGCCGTGG CCTCGCCGCT GTGCACGTGG CTGGTGGCGG
CGTGCATGAC GGTGGCGTGC GACAAGGAGT GGCCGCTGGG GCCGGGGAGT GCGTCCCCCC
GGCGGAGGTG GCGGAGGGCG TCGCTCTCCG GCGGCGTGGG CCGGGCTTCG CCGAGGCGGC
TGATCTCGGC CTTCTGTGGG GCGGGGATCC AGGGGTTGAT GAGCTCGTGC CTGGCCTTCG
AGCCCTGCGC CGAGTTCTAC AGCTCGAGAA ATGGGTCGGC GTTCTTTGGG GGGGATGGCT
TCTCTCTGCT TGGGCGGCAG AATGCTGAGA CTACTCGAAG GCAGCAAGG GGTGCCCGTT
CTTCTCCTTC TTCTGTTGCA GGAAAAGTCA TGTCCATTGC TGTGCAGCCT GAAAAGAAGG
TTGCAGAGAA AGAGAGAACC CAAACCAAAC AGCGGAGGGT TGTTGTGACG GGAATGGGTG
TGGTGACTCC ATTAGGCCAT GATCCAGATC ATTTCTATGA AGAGCTCCTC AAGGGTGTTA
GTGGCATAAG TGAAATAGAA ACATTCGACT GTTCCAGTTA TCCAACGAGG ATTGCAGGAG
AAATTAAATC TTTTTCCTCG GATGGATGGG TGGCACCAAA ACTATCCAAA AGGATGGACA
AGTTTATGCT TTACTTACTT ACTGCTGGCA AGAAAGCATT GGAAAATGGT GGACTTACAG
AAGAGGCTAT GAGTTGGTTG GATAAGGAAA GATGTGGAGT TCTCATTGGG TCTGCAATGG
GTGGAATGAA AGTTTTTAAT GATGCAATTG AGGCTTTAAG GATCTCGTAC AAGAAGATGA
ACCCCTTTTG TGTACCCTTT GCAACTACGA ATATGGGCTC TGCAATGCTT GCAATGGATC
TAGGTTGGAT GGGCCCAAAC TATTCTATTT CTACTGCATG TGCAACTAGC AACTTCTGTA
TTTTGAATGC AGCAAACCAT ATTATAAGAG ATGAAGCTGA TGTGATGCTT TGTGGTGGCT
CTGATGCAGC AATTATACCA ATTGGATTGG GGGGTTTTGT GGCATGCGGA GCACTTTCAC
```

```
KasU86m    ----------  ----------  ----------  ----------  ----------
KasU26RC   ----------  ----------  ----------  ----------  ----------
   KasU24  CCACTCACAA  GGCTGTAAAG  AATAAAAAAG  TTAGGTTTAA  ACTTTAAATC

KasU86m    ----------  ----------  ----------  ----------  ----------
KasU26RC   ----------  ----------  ----------  ----------  ----------
   KasU24  ACCTTTTTAT  ATCTATATCC  CCTCTTTGCA  AGTTGGCGAT  GGCTTTCGCC

KasU86m    ----------  ----------  ----------  ----------  ----------
KasU26RC   ----------  ----------  ----------  ----------  ----------
   KasU24  ACGTCCCCTT  GGTTTCGCCA  AAGCTCGTGC  CTTTTCTTCC  GTAAGATCGA

KasU86m    ----------  ----------  ----------  ----------  ----------
KasU26RC   ----------  ----------  ----------  ----------  ----------
   KasU24  TGCCATCTTT  CATTCCCTTC  GTCAGCTTTT  CTCCCCTCCC  AAAACCTTTC

KasU86m    ----------  ----------  ----------  ----------  ----------
KasU26RC   ----------  ----------  ----------  ----------  ----------
   KasU24  GCCATCCTCT  TCGACCCGTT  TCCTCCTTCC  CAAAATCGCA  TATTTTCTCG
```

Figure 6 continued

| | | | | | |
|---|---|---|---|---|---|
| KasU86m  | ---------- | ---------- | ---------- | ---------- | ---------- |
| KasU26RC | ---------- | ---------- | ---------- | ---------- | ---------- |
| KasU24   | TTAAAAATCG | CTCTTTTTTC | TCTCGCTGTT | TCTTAGTCCG | CTCTTTGAGA |
| | | | | | |
| KasU86m  | ---------- | ---------- | ---------- | ---------- | ---------- |
| KasU26RC | ---------- | ---------- | ---------- | ---------- | ---------- |
| KasU24   | TCTTGAATCC | CTTCTTGGCC | TCTTCTCCTC | TCTCAACTTC | GATCGGAACG |
| | | | | | |
| KasU86m  | ---------- | ---------- | ---------- | ---------- | ---------- |
| KasU26RC | ---------- | ---------- | ---------- | ---------- | ---------- |
| KasU24   | TTCTCGAGTT | CTAGCTTCTG | CCCGCTCCGC | TTTTGGAGCT | TCTCTCCTCC |
| | | | | | |
| KasU86m  | ---------- | ---------- | ---------- | ---------- | ---------- |
| KasU26RC | ---------- | ---------- | ---------- | ---------- | ---------- |
| KasU24   | CTTATTCCGG | CTTTGCTCTG | TTCTTCTCCA | ATGGCGGGCG | CCGCCGTGGC |
| | | | | | |
| KasU86m  | ---------- | ---------- | ---------- | ---------- | ---------- |
| KasU26RC | ---------- | ---------- | ---------- | ---------- | ---------- |
| KasU24   | CTCGCCGCTG | TGCACGTGGC | TGGTGGCGGC | GTGCATGACG | GTGGCGTGCG |
| | | | | | |
| KasU86m  | ---------- | ---------- | ---------- | ---------- | ---------- |
| KasU26RC | ---------- | ---------- | ---------- | ---------- | ---------- |
| KasU24   | ACAAGGAGTG | GCCGCTGGGG | CCGGGGAGTG | CGTCCCCCCG | GCGGAGGTGG |
| | | | | | |
| KasU86m  | ---------- | ---------- | ---------- | ---------- | ---------- |
| KasU26RC | ---------- | ---------- | ---------- | ---------- | ---------- |
| KasU24   | CGGAGGGCGT | CGCTCTCCGG | CGGCGTGGGC | CGGGCTTCGC | CGAGGCGGCT |
| | | | | | |
| KasU86m  | ---------- | ---------- | ---------- | ---------- | ---------- |
| KasU26RC | ---------- | ---------- | ---------- | ---------- | ---------- |
| KasU24   | GATCTCGGCC | TTCTGTGGGG | CGGGGATCCA | GGGGTTGATG | AGCTCGTGCC |
| | | | | | |
| KasU86m  | ---------- | ---------- | ---------- | ---------- | ---------- |
| KasU26RC | ---------- | ---------- | ---------- | ---------- | ---------- |
| KasU24   | TGGCCTTCGA | GCCCTGCGCC | GAGTTCTACA | GCTCGAGAAA | TGGGTCGGCG |
| | | | | | |
| KasU86m  | ---------- | ---------- | ---------- | ---------- | ---------- |
| KasU26RC | ---------- | ---------- | ---------- | ---------- | ---------- |
| KasU24   | TTCTTTGGGG | GGGATGGCTT | CTCTCTGCTT | GGGCGGCAGA | ATGCTGAGAC |
| | | | | | |
| KasU86m  | ---------- | ---------- | ---------- | ---------- | ---------- |
| KasU26RC | ---------- | ---------- | ---------- | ---------- | ---------- |
| KasU24   | TACTCGAAGG | CAGCGAAGGG | GTGCCCGTTC | TTCTCCTTCT | TCTGTTGCAG |

```
KasU86m    ---------- ---------- ---------- ---------- ----------
KasU26RC   ---------- ---------- ---------- ---------- ----------
   KasU24  GAAAAGTCAT GTCCATTGCT GTGCAGCCTG AAAAGAAGGT TGCAGAGAAA

KasU86m    ---------- ---------- ---------- ---------- ----------
KasU26RC   ---------- ---------- ---------- ---------- ----------
   KasU24  GAGAGAACCC AAACCAAACA GCGGAGGGTT GTTGTGACGG GAATGGGTGT

KasU86m    ---------- ---------- ---------- ---------- ----------
KasU26RC   ---------- ---------- ---------- ---------- ----------
   KasU24  GGTGACTCCA TTAGGCCATG ATCCAGATCA TTTCTATGAA GAGCTCCTCA

KasU86m    ---------- ---------- ---------- ---------- ----------
KasU26RC   ---------- ---------- --------GC CCTTGGACAC TGACATGGAC
   KasU24  AGGGTGTTAG TGGCATAAGT GAAATAGAAA CATTCGACTG TTCCAGTTAT

KasU86m    ---------- ---------- ---------- ---------- ----------
KasU26RC   TGAAGGAGTA GAAAATTGCA GGAGAAATTA ATTTTTTTC  AACAGATGGA
   KasU24  CCAACGAGGA -----TTGCA GGAGAAATTA AATCTTTTTC CTCGGATGGA

KasU86m    ---------- ---------- ---------- ---------- ----------
KasU26RC   TTGGTGGCAC CTAAATTATC TAAACGAATG G-CAAATTCA TGCTCTATTT
   KasU24  TGGGTGGCAC CAAAACTATC CAAAAGGATG GACAAGTTTA TGCTTTACTT

KasU86m    ---------- ---------- ---------- ---------- ----------
KasU26RC   ACTTATTGCT GGAAAGAAAG CATTAGCCAA TGGTGGGGTT ATTGAAGAGG
   KasU24  ACTTACTGCT GGCAAGAAAG CATTGGAAAA TGGTGGACTT ACAGAAGAGG

KasU86m    ---------- ---------- ---------- ---------- ----------
KasU26RC   TCATGAGTCA GCTTGACAAG GCAAAATGCG GAGTGCTCAT AGGCTCTGCG
   KasU24  CTATGAGTTG GTTGGATAAG GAAAGATGTG GAGTTCTCAT TGGGTCTGCA

KasU86m    ---------- ---------- ---------- ---------- ----------
KasU26RC   ATGGGTGGAA TGAAGGTTTT TAATGATGCC ATCGAAGCTT TAAGGGTCTC
   KasU24  ATGGGTGGAA TGAAAGTTTT TAATGATGCA ATTGAGGCTT TAAGGATCTC

KasU86m    ---------- ---------- ---------- ---------- ----------
KasU26RC   ATATAAGAAG ATGAATCCAT TTTGTGTTCC ATTTGCAACG ACAAACATGG
   KasU24  GTACAAGAAG ATGAACCCCT TTTGTGTACC CTTTGCAACT ACGAATATGG

KasU86m    ---------- ---------- ---------- ---------- ----------
KasU26RC   GTTCTGCAAT CCTTGCCATG GATCTGGGTT GGATGGGCCC AAATTACTCT
   KasU24  GCTCTGCAAT GCTTGCAATG GATCTAGGTT GGATGGGCCC AAACTATTCT
```

Figure 6 continued

```
KasU86m    ---------- ---------- ---------- ---------- ----------
KasU26RC   ATTTCAACTG CTTGTGCTAC AAGCAATTTC TGTATCCTGA ATGCAGCAAA
KasU24     ATTTCTACTG CATGTGCAAC TAGCAACTTC TGTATTTTGA ATGCAGCAAA

KasU86m    ---------- ---------- ---------- ---------- ----------
KasU26RC   CCATATAATA AGAGGGGAAG CGGATGTGAT GCTTTGTGGT GGATCAGATG
KasU24     CCATATTATA AGAGATGAAG CTGATGTGAT GCTTTGTGGT GGCTCTGATG

KasU86m    ---------- ---------- ---------- ---------- ----GCCCTT
KasU26RC   CTGCTATTAT ACCAATTGGA CTGGGGGGTT TTGTTGCTTG CAGAGCA---
KasU24     CAGCAATTAT ACCAATTGGA TTGGGGGGTT TTGTGGCATG CGGAGCA---

KasU86m    CTCTCGCAGA GAAATAGTGA TCCGACTAAA GCGTCACGGC CTTGGGACAT
KasU26RC   CTCTCGCAGA GAAATAGTGA TCCGACTAAA GCGTCACGGC CTTGGGACAT
KasU24     CTTTCAC--- ---------- ---------- ---------- ----------

KasU86m    TGATCGTGAT GGATTCGTGA TGGGGGAGGG GGCTGGCGTG CTTCTACTGG
KasU26RC   TGATCGTGAT GGATTCGTGA TGGGGGAGGG GGCTGGCGTG CTTCTACTGG
KasU24     ---------- ---------- ---------- ---------- ----------

KasU86m    AAGAATTAGA GCATGCTAAG --CAAAGAGG AGCAAATATC TATGCTGAAT
KasU26RC   AAGAATTAGA GCATGCTAAG GGCGAATTCG TTTAAACCTG CAGGACTAGT
KasU24     ---------- ---------- ---------- ---------- ----------

KasU86m    TTCTTGGGGG AAGCTTCACA TGTGATGCTT ACCACATGAC TGAGCCACAT
KasU26RC   CCCTTTAGTG AGGGTTAAT- TCTGA-GCTT GGCGTAGG-C AGGTCAACGT
KasU24     ---------- ---------- ---------- ---------- ----------

KasU86m    CCTGAGGGGG CAGGCATTGC TCTTTGCATT GAGAACGCAT TAGCACAAGC
KasU26RC   TTTAACCTC- ---------- ---------- ---------- ----------
KasU24     ---------- ---------- ---------- ---------- ----------

KasU86m    AGGGGTAGCC AAAGAAGATG TTAATTATGT AAATGCTCAT GCAACTTCAA
KasU26RC   ---------- ---------- ---------- ---------- ----------
KasU24     ---------- ---------- ---------- ---------- ----------

KasU86m    CACCTGCTGG TGACCTAAAA GAGTATCAAG CTCTCATTCG TTGTTTTGGG
KasU26RC   ---------- ---------- ---------- ---------- ----------
KasU24     ---------- ---------- ---------- ---------- ----------

KasU86m    CAGAATCCTG AGCTGAGAGT GAACTCTACA AAATCAATGA TTGGTCACCT
KasU26RC   ---------- ---------- ---------- ---------- ----------
KasU24     ---------- ---------- ---------- ---------- ----------
```

Figure 6 continued 2

| KasU86m | ACTAGGAGCT | TCTGGTGCGG | TGGAAGCTGT | TGCTGCAATT | CAGGCAATTC |
| --- | --- | --- | --- | --- | --- |
| KasU26RC | ---------- | ---------- | ---------- | ---------- | ---------- |
| KasU24 | ---------- | ---------- | ---------- | ---------- | ---------- |

| KasU86m | GAACAGGGTG | GGTCCATCCA | AATGTCAATC | TCGAAAACCC | AGAAAAAAGT |
| --- | --- | --- | --- | --- | --- |
| KasU26RC | ---------- | ---------- | ---------- | ---------- | ---------- |
| KasU24 | ---------- | ---------- | ---------- | ---------- | ---------- |

| KasU86m | GTGGATATAA | ATGTGCTGGT | GGGCTCGAAA | AAAGGAAAAG | GTTGGATGTG |
| --- | --- | --- | --- | --- | --- |
| KasU26RC | ---------- | ---------- | ---------- | ---------- | ---------- |
| KasU24 | ---------- | ---------- | ---------- | ---------- | ---------- |

| KasU86m | ATAAGCTGGT | GGGCTCAAAG | AAGGAAAGAT | TGGATGTGAA | GGTGGCCCTG |
| --- | --- | --- | --- | --- | --- |
| KasU26RC | ---------- | ---------- | ---------- | ---------- | ---------- |
| KasU24 | ---------- | ---------- | ---------- | ---------- | ---------- |

| KasU86m | TCAAACTCTT | TTGGCTTTGG | TGGCCACAAC | TCGTCTATCC | TGTTTGCACC |
| --- | --- | --- | --- | --- | --- |
| KasU26RC | ---------- | ---------- | ---------- | ---------- | ---------- |
| KasU24 | ---------- | ---------- | ---------- | ---------- | ---------- |

| KasU86m | ATACAAATAA | GCATCAGCTA | TGGGCCTACA | AAAGCATCAA | GGTCATCTTA |
| --- | --- | --- | --- | --- | --- |
| KasU26RC | ---------- | ---------- | ---------- | ---------- | ---------- |
| KasU24 | ---------- | ---------- | ---------- | ---------- | ---------- |

| KasU86m | CATGTAATTT | GTATCAGAAA | TGACTGTGTG | GTGCTTATGT | TTTTATTTGG |
| --- | --- | --- | --- | --- | --- |
| KasU26RC | ---------- | ---------- | ---------- | ---------- | ---------- |
| KasU24 | ---------- | ---------- | ---------- | ---------- | ---------- |

| KasU86m | CACCAACATC | TTGATCATAT | GGAATTGGTC | TAGATGCCGT | TATAGCTCAT |
| --- | --- | --- | --- | --- | --- |
| KasU26RC | ---------- | ---------- | ---------- | ---------- | ---------- |
| KasU24 | ---------- | ---------- | ---------- | ---------- | ---------- |

| KasU86m | AATAGAATGG | TATATAGTGC | ACTACTTTCA | AAAAAAAAAA | AAAACTCAGG |
| --- | --- | --- | --- | --- | --- |
| KasU26RC | ---------- | ---------- | ---------- | ---------- | ---------- |
| KasU24 | ---------- | ---------- | ---------- | ---------- | ---------- |

Figure 6 continued[3]

```
AAAGCTCGTGCCTTTTCTTCCNTAAGATCGATGCCATCTTTCATTCCCTTCGTCAGCTTTTCTCCCCTCCCAAAA
CCTTTCGCCATCCTCTTCGACCCGTTTCCTCCTTCCCAAAATCGCATATTTTCTCGTTAAAAATCGCTCTTTTTT
CTCTCGCTGTTTCTTAGTCCGCTCTTTGAGATCTTGAATTCGCCCTTGGCCTCTTCTCCTCTCTCAACTTCGATC
GGAACGTTCTCGAGTTCTAGCTTCTGCCCGCTCCGCTTTTGGAGCTTCTCTCCTCCCTTATTCCGGCTTTGCTCT
GTTCTTCTCCAATGGCGGGCGCCGCCGTGGCCTCGCCGCTGTGCACGTGGCTGGTGGCGGCGTGCATGACGGTGG
CGTGCGACAAGGAGTGGCCGCTGGGGCCGGGGAGTGCGTCCCCCGGCGGAGGTGGCGGAGGGCGTCGCTCTCCG
GCGGCGTGGGCCGGGCTTCGCCGAGGCGGCTGATCTCGGCCTTCTGTGGGGCGGGGATCCAGGGGTTGATGAGCT
CGTGCCTGGCCTTCGAGCCCTGCGCCGAGTTCTACAGCTCGAGAAATGGGTCGGCGTTCTTTGGGGGGGATGGCT
TCTCTCTGCTTGGGCGGCAGAATGCTGAGACTACTCGAAGGCAGCGAAGGGGTGCCCGTTCTTCTCCTTCTTCTG
TTGCAGGAAAAGTCATGTCCATTGCTGTGCAGCCTGAAAAGAAGGTTGCAGAGAAAGAGAGAACCCAAACCAAAC
AGCGGAGGGTTGTTGTGACGGGAATGGGTGTGGTGACTCCATTAGGCCATGATCCAGATCATTTCTATGAAGAGC
TCCTCAAGGGTGTTAGTGGCATAAGTGAAATAGAAACATTCGACTGTTCCAGTTATCCAACGAGGATTGCAGGAG
AAATTAAATCTTTTTCCTCGGATGGATGGGTGGCACCAAAACTATCCAAAAGGATGGACAAGTTTATGCTTTACT
TACTTACTGCTGGCAAGAAAGCATTGGAAAATGGTGGACTTACAGAAGAGGCTATGAGTTGGTTGGATAAGGAAA
GATGTGGAGTTCTCATTGGGTCTGCAATGGGTGGAATGAAAGTTTTTAATGATGCAATTGAGGCTTTAAGGATCT
CGTACAAGAAGATGAACCCCTTTTGTGTACCCTTTGCAACTACGAATATGGGCTCTGCAATGCTTGCAATGGATC
TAGGTTGGATGGGCCCAAACTATTCTATTTCTACTGCATGTGCAACTAGCAACTTCTGTATTTTGAATGCAGCAA
ACCATATTATAAGAGATGAAGCTGATGTGATGCTTTGTGGTGGCTCTGATGCAGCAATTATACCAATTGGATTGG
GGGGTTTTGTGGCATGCGGAGCACTCTCGCAGAGAAATAGTGATCCGACTAAAGCGTCACGGCCTTGGGACATTG
ATCGTGATGGATTCGTGATGGGGGAGGGGGCTGGCGTGCTTCTACTGGAAGAATTAGAGCATGCTAAGCAAAGAG
GAGCAAATATCTATGCTGAATTTCTTGGGGGAAGCTTCACATGTGATGCTTACCACATGACTGAGCCACATCCTG
AGGGGGCAGGCATTGCTCTTTGCATTGAGAACGCATTAGCACAAGCAGGGGTAGCCAAAGAAGATGTTAATTATG
TAAATGCTCATGCAACTTCAACACCTGCTGGTGACCTAAAAGAGTATCAAGCTCTCATTCGTTGTTTTGGGCAGA
ATCCTGAGCTGAGAGTGAACTCTACAAAATCAATGATTGGTCACCTACTAGGAGCTTCTGGTGCGGTGGAAGCTG
TTGCTGCAATTCAGGCAATTCGAACAGGGTGGGTCCATCCAAATGTCAATCTCGAAAACCCAGAAAAAGTGTGG
ATATAAATGTGCTGGTGGGCTCGAAAAAAGGAAAAGGTTGGACGTCAATAAGCTGGTGGGCTCAAAGAAGGAAA
GATTGGATGTGAAGGTGGCCCTGTCAAACTCTTTTGGCTTTGGTGGCCACAACTCGTCTATCCTGTTTGCACCA
TACAAATAAGCATCAGCTATGGGCCTACAAAAGCATAAGGGCGAATTCCATCTTACATGTAATTTGTATCAGAA
ATGACTGTGTGGTGCTTATGTTTTTATTTGGCACCAACATCTTGATCATATGGAATTGGTCTAGATGCCGTTAT
AGCTCATAATAGAATGGTATATAGTGCACTACTTTCAAAAAAAAAAAAAAACTCAGG
```

```
KasEg2C                        CCACTACAAGGTAAAGAATAAAAAAGTTGGTTTAACTTTAATCACCT
Cuphea_wrightii [CWU67317]     -----------------------------------------------
Perilla_frutescens[AF026149    -----------------------------------------------
Elaeis_guineensis[AF220453]    -----------------------------------------------

KasEg2C                        TTTCTTTCCCCTCTTTGCAAGTTGGCGATGGCTTTCGCCACTCCCCT
Cuphea_wrightii                -----------------------------------------------
Perilla_frutescens[AF026149    -----------------------------------------------
Elaeis_guineensis[AF220453]    -----------------------------------------------

KasEg2C                        TTTCGCCAAAGCTCGTGCCTTTTCTTCCTAAGATCGATGCCATCTTT
Cuphea_wrightii                -----------------------------------------------
Perilla_frutescens[AF026149    -----------------------------------------------
Elaeis_guineensis[AF220453]    -----------------------------------------------

KasEg2C                        TCCCTTCGTCAGCTTTTCTCCCCTCCCAAAACCTTTCGCCATCCTCT
Cuphea_wrightii                -----------------------------------------------
Perilla_frutescens[AF026149    -----------------------------------------------
Elaeis_guineensis[AF220453]    -----------------------------------------------

KasEg2C                        ACCCGTTTCCTCCTTCCCAAAATCGCATATTTTCTCGTTAAAAATCG
Cuphea_wrightii                -----------------------------------------------
Perilla_frutescens[AF026149    -----------------------------------------------
Elaeis_guineensis[AF220453]    -----------------------------------------------

KasEg2C                        TTTTTTCTCTCGCTGTTTCTTAGTCCGCTCTTTGAGATCTTGAATCC
Cuphea_wrightii                ------CAACAACAGAGCAGAAGCATTGTGTTGGGAAGATTGAATGC
Perilla_frutescens[AF026149    -----------------------------------------------
Elaeis_guineensis[AF220453]    -----------------------------------------------

KasEg2C                        CTTGGCCTCTTCTCCTCTCTCAACTTCGATCGGAACGTTCTCGAGTT
Cuphea_wrightii                ---AGTCTCGTCT---------GCTTTGCTCAGAA-GTTGCCACTGA
Perilla_frutescens[AF026149    -----------------------------------------------
Elaeis_guineensis[AF220453]    ---------------------------------------ACCCCAAATCCT
```

Figure 8 continued

```
KasEg2C                     GCTTCTGCCCGCTCCGCTTTTGGAGCTTCTCTCCTCCCTTATTCCGG
Cuphea_wrightii             GCT-CTGTGCGTTCTTCTTCCAAAAGGGTATCCATTTTCTACTT-GG
Perilla_frutescens[AF026149 -----------------------------------------------
Elaeis_guineensis[AF220453] TCTCTTAAACCCTCTCTCTCCCTTCTCTTATAAACCCTTGTAGTCTC KasEg2C                     TGCTCTGTTC--TTCTCCAATGGCGGGCGCCGCC------GTGGCCT
Cuphea_wrightii             GGCTCAGTTTGGTGTTTCAATGGCGGCCGCCGCTTCCATGGTTGCGT
Perilla_frutescens[AF026149 ---------------------------------------------T
Elaeis_guineensis[AF220453] TCCTTCTCTTCTTTCTCCGATGGCGGGATACTCG------GTGGCGG KasEg2C                     CGCTGTGCACGTGGCTGGTGGCGGCGTGCATGACGGTGGCGTGCGAC
Cuphea_wrightii             CATTCTGTACGTGGCTCGTAGCCTCTTGCATGTCCACTTCATTCGAC
Perilla_frutescens[AF026149 TGGTGTGCTCATGGCTAATGGCCGCATGCATGTC--CGTCACGTGTG
Elaeis_guineensis[AF220453] CGCTGTGCACGTGGTTGGTGGCAGCGTGCGTGACGGCGTCGGGTGGA
                              * **   * ***  *    * **   * *** ** *    *   *

KasEg2C                     GAGTGGCC---------GCTGGGGC---CGGGGAGTG--------CG
Cuphea_wrightii             GACCCACG---------TTCGCCGT---CCGTCAA-G--------CG
Perilla_frutescens[AF026149 GAGAATCC------GGCGTTTCTGC--GCTGTCGACGACGT----CG
Elaeis_guineensis[AF220453] GAGGGGCCTTTGGCGGCGCCGGCGCCGGCGGTCGGGGAGGCGAGGCG
                            **    *              *       *  *    *       **

KasEg2C                     CCCCGG----CGGAGGTGGCGGAGGGCGTCGCTCTCCGGCGGCGTGG
Cuphea_wrightii             CCCCCG----C--------CGGAAGAGGGTTCTCTCC--CAACGCGG
Perilla_frutescens[AF026149 AATTCA--CGCCGCCTCACCAAATGG--GCCGCCCACCGCCGCAA--
Elaeis_guineensis[AF220453] GAGCCGGTCGGCGAGGAGGCGGAGGGCGGCGGCGCTCCGCCTCGACG
                                *    *                         *   *  *

KasEg2C                     GGGCTTCGCCGAGGCGGCTGATCTCGGCCTTCTGTGGGGCGGGGATC
Cuphea_wrightii             CACATTC--CAATGC-------CTCGTCGCCCTCATGCATCG---ACC
Perilla_frutescens[AF026149 GAGGGTTCTC-----GCCAAATGT----GCGCCGCGCATTCGGAATC
Elaeis_guineensis[AF220453] GGGATTCCTCTGGAGGACTGATGTCGGCGCTCCGTGGATCGGGGATC
                              *    *              *       *       *   * * *

KasEg2C                     GGGTTGATGAGCTCGTGCCTGGCCTTCGAGCCCTGCGCCGAGTTCTA
Cuphea_wrightii             G---TGATCAA----TACCGGTCCTCCG---CCTCCCTTAGCTTCCT
Perilla_frutescens[AF026149 -------TGGATTCTTCTCTCTCCCTTGAGCCCCGCCACCACTTGCA
Elaeis_guineensis[AF220453] GGGCTGATGAGCTCCTGCCTCGCCTTCGAGCCCTGCGCGGAGTTCTA
                                 *     *     *  **   *  **   *       **

KasEg2C                     CTCGAGAAATGGGTCGGCGTTCTTTGGGGGGATGGCTTCTCTCTGC
Cuphea_wrightii             ----GGATAACGGAT------------------TTGCTTCCCTTT--
Perilla_frutescens[AF026149 ATCTCACGA------ATGTTTCTTCGG---------------CT
Elaeis_guineensis[AF220453] CTCTAAGGGCGCGTCGGCTTTCTTCGGAGAGAGTGGCTTCTCCCTCT
```

| | |
|---|---|
| KasEg2C | GGCGGCAGAATGCTGAGACTACTCGAAGGCAGCGAAGGGGTGCCCGT |
| Cuphea_wrightii | GATCCAAGCCATTCATGTCCAATCGCGGCCACCGGAGGCTCCGCCGT |
| Perilla_frutescens[AF026149 | AATCGAGAAATGCTCCGATGCAGCGCGGCCGCCAGAAACTCCTCCAC |
| Elaeis_guineensis[AF220453] | GGACGTCGAAGGCGGAGACTACGAGAAGGCAGCGAAGGGCCGCGCGC |
| | *   *  * *  *  *      * |

| | |
|---|---|
| KasEg2C | TCTCCTTCTTCTGTTGCAGGAAAAGTCATGTCCATTGCTGTGCAGCC |
| Cuphea_wrightii | TCCCATTCC--------GGGGAGGCCATGGCTGTGGCTCTGCAACC |
| Perilla_frutescens[AF026149 | TCCGCCTATTCT------GGAGAAATGATGGCAGTAGCTGTAAATCC |
| Elaeis_guineensis[AF220453] | TCTTGCGTCTCG------GGCAAAGCAATGGCAGTAGCTGTGCAGCC |
| | **          ** *   ***  *  * ***  *  *  ** |

| | |
|---|---|
| KasEg2C | AAAGAAGGTTGCAGAGAAAGAGAGAACCCAAACCAAACAGCGGAGGG |
| Cuphea_wrightii | ACAGGAAGCTGGCACGAAGAAGAAACCTGTTATCAAGCAAAGGCGAG |
| Perilla_frutescens[AF026149 | CATGGAAGTTTCACCCAAGAAGAAACCTCCAACCAAGCACCGACGAG |
| Elaeis_guineensis[AF220453] | TAAGGAAATTGCAGAAAAGAAGAGAACCCATACAAAGAAGAGGAGAG |
| | *  *   *       **  *** * *    *   **  *  *   * * |

| | |
|---|---|
| KasEg2C | TTGTGACGGGAATGGGTGTGGTGACTCCATTAGGCCATGATCCAGAT |
| Cuphea_wrightii | TTGTTACCGGAATGGGCGTGGTTACTCCTCTAGGCCATGAACCTGAT |
| Perilla_frutescens[AF026149 | TCGTGACAGGTATGGGTGTGGAGACACCACTTGGTAGTGATCCAGAT |
| Elaeis_guineensis[AF220453] | TCGTGACAGGGATGGGTGTGGTGACTCCACTGGGCGTTGATCCTGGT |
| | * **  ** **  ***** ****  **  **  * **    *** ** * ** |

| | |
|---|---|
| KasEg2C | TTCTATGAAGAGCTCCTCAAGGGTGTTAGTGGCATAAGTGAAATAGA |
| Cuphea_wrightii | TTCTACAACAATCTTCTAGATGGAGTAAGCGGCATAAGTGAGATAGA |
| Perilla_frutescens[AF026149 | TTCTATAATAATCTGCTAGAAGGAGTCAGTGGAATTAGTGAGATAGA |
| Elaeis_guineensis[AF220453] | TTCTACAATAACCTTCTTGATGGTGTCAGTGGTATAAGTCAAATTGA |
| | *****   *   *  ** **   * ** ** **  ** ** ***  *  ** ** |

| | |
|---|---|
| KasEg2C | ATTCGACTGTTCCAGTTATCCAACGAGGATTGCAGGAGAAATTAAAT |
| Cuphea_wrightii | CTTCGACTGCACTCAGTTTCCCACGAGAATTGCCGGAGAGATCAAGT |
| Perilla_frutescens[AF026149 | TTTTGATTGCTCGCAGTTTCCAACCAGAATTGCTGGAGAAATCAAGT |
| Elaeis_guineensis[AF220453] | ATTTGACTGTACCAACTATCCAACAAGAATTGCAGGAGAAATTAAAT |
| | ** ** **  *     * *** ** **  ***** **** * * ** ** * |

| | |
|---|---|
| KasEg2C | TTTCCTCGGATGGATGGGTGGCACCAAAACTATCCAAAAGGATGGAC |
| Cuphea_wrightii | TTTCCACAGATGGGTGGGTGGCCCCAAAGCTATCCAAGAGGATGGAC |
| Perilla_frutescens[AF026149 | TCTCAACAGATGGCTGGGTTGTACCTAAACTTTCCAAGAGAATGGAC |
| Elaeis_guineensis[AF220453] | TTTCAACAGATGGATTGGTGGCACCTAAATTATCTAAACGAATGGAC |
| | * **  *  ***** * ***  * **  *  ** **   * ****** |

| | |
|---|---|
| KasEg2C | TTTATGCTTTACTTACTTACTGCTGGCAAGAAAGCATTGGAAAATGG |
| Cuphea_wrightii | TTCATGCTTTACTTGTTGACTGCTGGCAAGAAAGCATTAGCAGATGG |
| Perilla_frutescens[AF026149 | TTCATGCTTTACATGTTGACAGCGGGCAAGAAGGCTTTGGCTGATGG |
| Elaeis_guineensis[AF220453] | TTCATGCTCTATTTACTTATTGCTGGAAAGAAAGCATTAGCCAATGG |
| | ** ***** **  *  *   **  ** *****  **  *    **** |

| | |
|---|---|
| KasEg2C | ACTTACAGAAGAGGCTATGAGTTGGTTGGATAAGGAAAGATGTGGAG |
| Cuphea_wrightii | AATCACCGATGAGGTGATGAAAGAGCTTGATAAAAGAAAGTGTGGAG |
| Perilla_frutescens[AF026149 | AATTACAGTAGATGCCATGGATGAACTAAATAAAGCAAAATGTGGTG |
| Elaeis_guineensis[AF220453] | GGTTACTGAAGAGGTCATGAGTCAGCTTGACAAGGCAAAATGCGGAG |
| |   * ** * ** * ***  ***    *   * *  **  ** *  |

Figure 8 continued

```
KasEg2C                         TCATTGGGTCTGCAATGGGTGGAATGAAAGTTTTTAATGATGCAATT
Cuphea_wrightii                 TCATTGGCTCCGGAATGGGCGGCATGAAGGTGTTCAACGATGCCATT
Perilla_frutescens[AF026149     TAATTGGCTCTGCTATGGGTGGAATGAAAGTTTTTTATGATGCGATT
Elaeis_guineensis[AF220453]     TCATAGGCTCTGCGATGGGTGGAATGAAGGTTTTTAATGATGCCATC
                                 * ** ** ** *  ***** ** ***** **  **   * ***** **

KasEg2C                         GCTTTAAGGATCTCGTACAAGAAGATGAACCCCTTTTGTGTACCCTT
Cuphea_wrightii                 GCTCTGAGGGTTTCATACAAGAAGATGAATCCCTTTTGTGTACCTTT
Perilla_frutescens[AF026149     GCATTGCGGGTCTCATATAGGAAGATGAATCCATTTTGTGTTCCTTT
Elaeis_guineensis[AF220453]     GCTTTAAGGGTCTCATATAAGAAGATGAATCCATTTTGTGTTCCATT
                                 **   *   **   * ** **  * ********* ** ******* ** **

KasEg2C                         AACTACGAATATGGGCTCTGCAATGCTTGCAATGGATCTAGGTTGGA
Cuphea_wrightii                 TACCACAAATATGGGATCAGCTATGCTTGCAATGGACTTGGGATGGA
Perilla_frutescens[AF026149     AACTACCAACATGGGTTCTGCCATGCTTGCAATGGATCTGGGATGGA
Elaeis_guineensis[AF220453]     AACGACAAACATGGGTTCTGCAATCCTTGCCATGGATCTGGGTTGGA
                                 ** ** ** *****  **  **  **  ***** *****   * ** ****

KasEg2C                         GCCCAAACTATTCTATTTCTACTGCATGTGCAACTAGCAACTTCTGT
Cuphea_wrightii                 GTCCTAACTACTCGATATCAACTGCCTGTGCAACAAGTAATTTCTGT
Perilla_frutescens[AF026149     GCCCAAACTACTCAATATCTACTGCTTGTGCAACAAGTAACTTTTGT
Elaeis_guineensis[AF220453]     GCCCAAATTACTCTATTTCAACTGCTTGTGCTACAAGCAATTTCTCT
                                 * ** ** ** ** ** ** ** *****  ***** ** **  * *

KasEg2C                         TTGAATGCAGCAAACCATATTATAAGAGATGAAGCTGATGTGATGCT
Cuphea_wrightii                 CTGAATGCTGCAAACCACATAATCAGAGGCGAAGCTGACATGATGCT
Perilla_frutescens[AF026149     CTGAATGCTGCTAACCACATCATCAGAGGTGAAGCTGACTTGATGCT
Elaeis_guineensis[AF220453]     CTGAATGCAGCAAACCATATAATAAGAGGGGAAGCTGATGTGATGCT
                                 ******* **  *****  ** ** **** ********  *******

KasEg2C                         TGGTGGCTCTGATGCAGCAATTATACCAATTGGATTGGGGGGTTTTG
Cuphea_wrightii                 TGGAGGCTCGGATGCAGTCATTATACCTATTGGTTTGGGAGGTTTTG
Perilla_frutescens[AF026149     TGGTGGCTCAGATGCAGCAATTATACCAATTGGATTGGGAGGCTTTG
Elaeis_guineensis[AF220453]     TGGTGGATCAGATGCTGCTATTATACCAATTGGACTGGGGGGTTTTG
                                 *** ** ** ***** *  ********  ******* * *** ** ****

KasEg2C                         CATGCGGAGCACTCTCGCAGAGAAATAGTGATCCGACTAAAGCGTCA
Cuphea_wrightii                 CGTGCCGAGCTTTGTCACAGAGGAATAGTGACCCTACCAAAGCCTCG
Perilla_frutescens[AF026149     CATGCAGAGCACTGTCACAAAGAAACAGTGATCCAACTAAAGCCTCA
Elaeis_guineensis[AF220453]     CTTGCAGAGCACTCTCGCAGAGAAATAGTGATCCGACTAAAGCGTCA
                                 *  *** ****   *    * **  ** **  ***** **  ***** **

KasEg2C                         CCTTGGGACATTGATCGTGATGGATTCGTGATGGGGGAGGGGCTGG
Cuphea_wrightii                 CCATGGGATAGTAATCGTGATGGATTTGTAATGGGCGAAGGAGCTGG
Perilla_frutescens[AF026149     CCCTGGGATAGTAATCGTGATGGATTTGTTATGGGAGAAGGTGCTGG
Elaeis_guineensis[AF220453]     CCTTGGGACATTGATCGTGATGGATTCGTGATGGGGGAGGGGCTGG
                                 ** *****  * * ************* **  *****  ** ** *****

KasEg2C                         GCTTCTACTGGAAGAATTAGAGCATGCTAAGCAAAGAGGAGCAAATA
Cuphea_wrightii                 GTTACTTCTCGAGGAGTTAGAGCATGCAAAGAAAAGAGGTGCAACCA
Perilla_frutescens[AF026149     ACTGCTCTTGGAGGAACTAGAACATGCAAAGAGTAGAGGTGCAACTA
Elaeis_guineensis[AF220453]     GCTTCTACTGGAAGAATTAGAGCATGCTAAGCAAAGAGGAGCAAATA
                                  ** *  * **  * **  **** ***** ***   ***** ****  *
```

Figure 8 continued²

| | |
|---|---|
| KasEg2C | ATGCTGAATTTCTTGGGGGAAGCTTCACATGTGATGCTTACCACATG |
| Cuphea_wrightii | ATGCGGAGTTTTTAGGGGGAAGTTTCACTTGCGATGCCTATCACATG |
| Perilla_frutescens[AF026149 | ATGCTGAGTTTCTTGGAGGAAGCTTCACTAGTGATGCTTATCACATG |
| Elaeis_guineensis[AF220453] | ATGCTGAATTTCTTGGGGGAAGCTTCACATGTGATGCTTACCACATG |
| | **** ** *** * ** ***** *****  * ***** ** ****** |

| | |
|---|---|
| KasEg2C | GAGCCACATCCTGAGGGGGCAGGCATTGCTCTTTGCATTGAGAACGC |
| Cuphea_wrightii | GAGCCTCACCCTGAAGGAGCTGGAGTGATCCTCTGCATAGAGAAGGC |
| Perilla_frutescens[AF026149 | GAGCCTCATCCACAAGGAACTGGTGTCATTTTATGCTTAGAGAAGGC |
| Elaeis_guineensis[AF220453] | GAGCCACATCCTGAGGGGGCAGGCATTGCTCTTTGCATTGAGAACGC |
| | ***** ** ** * ** * ** *  * *** * ***** ** |

| | |
|---|---|
| KasEg2C | AGCACAAGCAGGGGTAGCCAAAGAAGATGTTAATTATGTAAATGCTC |
| Cuphea_wrightii | GGCTCAGGCCGGAGTCTCTAAAGAGGACGTGAATTACATAAATGCGC |
| Perilla_frutescens[AF026149 | GGCTCAATCAGGAGTATCTAAAGAAGATGTGAATTATATAAATGCAC |
| Elaeis_guineensis[AF220453] | AGCACAAGCAGGGGTAGCCAAAGAAGATGTTAATTATGTAAATGCTC |
| | ** **  * ** **   * ***** ** ** *****  ******* * |

| | |
|---|---|
| KasEg2C | CAACTTCAACACCTGCTGGTGACCTAAAAGAGTATCAAGCTCTCATT |
| Cuphea_wrightii | CAACTTCCACATCCGCTGGAGATATCAAGGAATACCAAGCTCTTGCC |
| Perilla_frutescens[AF026149 | CAACTTCTACTCCAGCTGGTGATCTTAAGGAGTATCAGGCTCTTCTT |
| Elaeis_guineensis[AF220453] | CAACTTCAACACCTGCTGGTGACCTAAAAGAGTATCAAGCTCTCATT |
| | ******* **  * ***** **  *  **  ** **  ** ** ***** |

| | |
|---|---|
| KasEg2C | TGTTTTGGGCAGAATCCTGAGCTGAGAGTGAACTCTACAAAAATCAAT |
| Cuphea_wrightii | TGTTTCGGTCAAAACAGTGAGCTGAGAGTTAATTCCACTAAAATCAAT |
| Perilla_frutescens[AF026149 | TGTTTTGGCAAGAATCCGGAGTTGAGAGTGAACTCCACAAAAATCCAT |
| Elaeis_guineensis[AF220453] | TGTTTTGGGCAGAATCCTGAGCTGAGAGTGAACTCTACAAAAATCAAT |
| | ***** **  *  **    *** ******* **  ** ** ***** ** |

| | |
|---|---|
| KasEg2C | TGGTCACCTACTAGGAGCTTCTGGTGCGGTGGAAGCTGTTGCTGCAA |
| Cuphea_wrightii | CGGTCATCTTCTTGGAGCAGCTGGTGGTGTAGAAGCAGTTACCGTAG |
| Perilla_frutescens[AF026149 | TGGGCACCTACTTGGAGCAGCTGGTGCTGTCGAGGCGGTTGCAACTG |
| Elaeis_guineensis[AF220453] | TGGTCACCTACTAGGAGCTTCTGGTGCGGTGGAAGCTGTTGCTGCAA |
| | ** ** ** ** *****  ****** ** ** *** * |

| | |
|---|---|
| KasEg2C | AGGCAATTCGAACAGGGTGGGTCCATCCAAATGTCAATCTCGAAAAC |
| Cuphea_wrightii | AGGCGATAAGGACCGGGTGGATCCATCCAAATCTTAATTTGGAAGAC |
| Perilla_frutescens[AF026149 | AGGCAATCAGGACTGGCTGGGTTCATCCAAATATTAATCTTGAAAAT |
| Elaeis_guineensis[AF220453] | AGGCAATTCGAACAGGGTGGGTCCATCCAAATGTCAATCTCGAAAAC |
| | **** **  *  ** ** ***  * ********* * *** * *** * |

| | |
|---|---|
| KasEg2C | GAAAAAGTGTGGATATAAATGTGCTGGTGGGCTCGAAAAAAGGAAA |
| Cuphea_wrightii | GACAAAGCTGTGGATGCAAAATTGCTCGTCGGACCTAAGAAGG--AG |
| Perilla_frutescens[AF026149 | GATGGTGGTGTGGATGCAAATGTGTTAGTGGGACCAACAAAAG--AA |
| Elaeis_guineensis[AF220453] | GAAAAAGTGTGGATATAAATGTGCTGGTGGGCTCGAGAAAGG--AA |
| | **     ******* ***   **   **  ** *  ** * * |

| | |
|---|---|
| KasEg2C | TTGGATGTGAATAAGCTGGTGGGCTCAAAGAAGGAAAGATTGGATGT |
| Cuphea_wrightii | CTGAATGTCAA--GGTCGGTTTGTCCAATTCATTCGGGTTCGG---T |
| Perilla_frutescens[AF026149 | CTCGACATTAA--GGTGGCATTGTCTAATTCGTTTGGGTTTGG---T |
| Elaeis_guineensis[AF220453] | TTGGATGTGAA--GGTGGCATTATCAAACTCATTCGGGTTTGG---T |
| |  *   *  ** *    *   ** **     ** * |

```
KasEg2C                        GGTGGCCCTGTCAAACTCTTTTGGCTTTGGTGGCCA----CAACTCG
Cuphea_wrightii                CATAACTCATCCATACTTTTCGCCCCTTGCAATGTC----TAAGTTT
Perilla_frutescens[AF026149    CATAACTCATCGATTTTGTTTGCTCCATACAAGTAGATTTTGTTGTG
Elaeis_guineensis[AF220453]    CACAACTCGTCTATCTTGTTTGCACC-TACAAATAG---------TC
                                 *  *      *    * **           *

KasEg2C                        ATCCTGTTTGCACCATA-CAAATAAGCATCAGCTATGGGCCTACAAA
Cuphea_wrightii                AGAACTACTGCACGTTAGTAGCTTAATGCCAC---TGGACATGGAAA
Perilla_frutescens[AF026149    GAATTGGGATCAAAGTGATGCAGAGATACATGTACTAGTCTCAAGAT
Elaeis_guineensis[AF220453]    GAAA-GAACTTCAGATGTTAAAAGATAGCACGCAGCTTCTTTGTTGG
                                                *

KasEg2C                        ATCA------A-GGTCATCTTACATGTAATTTGTATCAGAAAT-GACT
Cuphea_wrightii                ATTA------TCGGTCGGA--AGCTGTAGTCAGAAACTGTGATAGACC
Perilla_frutescens[AF026149    ACTAGGAAAAAGGCCCTCGAGACAACTGTAAAGACACTACAT-TTCT
Elaeis_guineensis[AF220453]    CC-------AAGATCATCTGAAGAATTCCAAG--CCATAGTT-TTCG
                                   *  *                                  *  *

KasEg2C                        TG---GTGCTTATGTTTTTATTTGGCACCAACATCTTGATCATATGG
Cuphea_wrightii                TACTTATACCGATGCCAAAGATCGGTATTGTTGTTAAGAGTCCACTG
Perilla_frutescens[AF026149    AAGTGATGATCAGAACCAAGGTACATTTTCTTGGTAGTTAGCATCTA
Elaeis_guineensis[AF220453]    AGCTTGCAACTAGGCCCCTGAT-TGTTGTGTAGG--GCTCATTTTGT
                                         *             *

KasEg2C                        TGGTCTAGATGCCGTTATAGCTCATAATAGAATGGTATA----TAGT
Cuphea_wrightii                TGTCCCTTTTTTTTTCCTTCCTCATCG-AGATTAGTCGA----ACTT
Perilla_frutescens[AF026149    TGGAGTTGTTCTTTTCCTGTTATGTATATTCCTGTTAGAGGAGAGCA
Elaeis_guineensis[AF220453]    TGGTAGTGTTATGCTCCTTGCAACGATATCATTACTTT------GTT
                               **        *       *  *                  *  *

KasEg2C                        CTACTTTCAAAAAAA---AAAAAAAAACTCAGG--------------
Cuphea_wrightii                AGCTTTTAATGAAGCCGGTGAAGAAACTAAGACTACTCGGGTACGTA
Perilla_frutescens[AF026149    TTACTTTCTG-TGCCGAGTGAAAGGTTTAGGTTAATTCGTCGGCAGA
Elaeis_guineensis[AF220453]    TTACTTCTAGCTGAATGATGCAAAGGTCAGAAGAAATTTCCCACC--
                                 **                     *

KasEg2C                        -----------------------------------------------
Cuphea_wrightii                GGGGACTGGTTTAGATTGGTGTGTTTTATCCTATGATCATTTGTA
Perilla_frutescens[AF026149    AGAGGTTGTGTTTTGTGGAATTTTATTTCTGATTCAGAGTAGTGTTT
Elaeis_guineensis[AF220453]    -----------------------------------------------

KasEg2C                        -----------------------------------------------
Cuphea_wrightii                TATATTTTGAAAAACCACATCCTTTGGTGCAAAATAATGCCGGCATT
Perilla_frutescens[AF026149    TTGCTACTGACGGGATTATCTACACTCTGCAGTGTTTTGTTTAGAA
Elaeis_guineensis[AF220453]    -----------------------------------------------

KasEg2C                        -----------------------------------------------
Cuphea_wrightii                GC---------------------------------------------
Perilla_frutescens[AF026149    TTATGCTAGAATGGGATTAAAGCAACTAGTGTTGTTGAATTGAAGCC
Elaeis_guineensis[AF220453]    -----------------------------------------------

KasEg2C                        -----------------------------------------------
Cuphea_wrightii                -----------------------------------------------
Perilla_frutescens[AF026149    ATGAAAATGTGATTTCTTTGTTGTGATAAAAAAAAAAAAAAAAAAAA
Elaeis_guineensis[AF220453]    -----------------------------------------------
```

Probe : Ribosomal DNA

RECOMBINANT ENZYME AND USES THEREFOR

RELATED APPLICATIONS

This application claims the benefit of Malaysian Patent Application No.: PI 20040179, filed 21 Jan. 2004.

FIELD OF THE INVENTION

The present invention relates to a polynucleotide sequence encoding an enzyme having β-ketoacyl ACP synthase II activity from a member of the Gramineae, Palmae, Juncaceae and Achenes families, in particular the Palmae family and most preferably from a species of oil palm. The present invention also relates to an enzyme having β-ketoacyl ACP synthase activity encoded by the polynucleotide sequence, methods for isolating the polynucleotide sequence and constructs for the expression of the polynucleotide sequence. The present invention further provides eukaryotic or prokaryotic cells comprising the polynucleotide sequences or constructs comprising same. Plants and parts of plants, such as flowering or reproductive parts including seeds, also form part of the present invention. The polynucleotide sequences of the present invention may be used inter alia for the generation of cells or plants comprising such cells which have a modified phenotype and/or which exhibit a desired characteristic. Examples of these characteristics include inter alia an increase or decrease in the total fatty acid content or a modulation of the ratio of C18 fatty acids to C16 fatty acids.

DESCRIPTION OF THE RELATED ART

Reference to any prior art in this specification is not, and should not be taken as, an acknowledgment or any form of suggestion that this prior art forms part of the common general knowledge in any country.

Numerous plant species are exploited for vegetable oils in the food and many other industries. Economically, oil palm provides a major source of revenue for tropical countries with Malaysia currently providing 50% of the total world production of palm oil. Oil palm (*Elaeis guineensis*) is a monocotyledon, belonging to Palmae family and is a unique crop in that it produces two distinct types of oil; palm oil and palm kernel oil. The oil palm fruit produces palm oil in the mesocarp and palm kernel oil in the seed. Palm oil which is generally extracted from the mesocarp layer of the oil palm fruits contains about 50% saturated, 40% monounsaturated and 10% polyunsaturated fatty acids. Its fatty acid composition consists of 44% palmitic acid (C16:0), 5% stearic acid (C18:0), 39% oleic acid (C18:1) and 10% linoleic acid (C18:2). Biochemical studies of fatty acid biosynthesis in oil palm mesocarp showed that the accumulation of palmitic acid in palm oil is due to limiting β-ketoacyl ACP synthase II (KAS II) activity. Thus, a positive correlation between KAS II activity and the unsaturation level of the fatty acids in the mesocarp has been observed for several palm varieties. Because of the high level of both saturated and monounsaturated fatty acids, palm oil is a semi-solid fat at room temperature. Thus, palm oil is used primarily in the food sector, typically as solid fat for margarine, shortening and cooking oil production. The composition and end-use pattern of palm kernel oil are similar to those of coconut oil due to the presence of high lauric acid. Thus, palm kernel oil is used by the oleochemical industry for the production of oleochemical derivatives such as soap, fatty amines, fatty esters and surfactant.

Fatty acids are normally present as essential components of complex lipid molecules. Higher plants synthesize fatty acids via a common pathway. In developing seeds, de novo production of fatty acids takes place in the proplastids. These fatty acids are attached to triacylglycerides and stored as a source of energy for further germination. The first step is the formation of acetyl-ACP (acyl carrier protein) from acetyl-CoA and ACP catalyzed by the enzyme, acetyl-CoA:ACP transacylase. Elongation of acetyl-ACP to 16- and 18-carbon fatty acids involves a series of four reactions; condensation with a two-carbon unit from malonyl-ACP to form a β-ketoacyl ACP (KAS II), reduction of the keto-function to an alcohol (β-ketoacyl ACP reductase), dehydration to form enoyl-ACP (β-hydroxyacyl-ACP dehydrase) and finally reduction of the enoyl-ACP to form the elongated saturated acyl-ACP (enoyl-ACP reductase). β-Ketoacyl ACP synthase I catalyzes elongation of the main saturated fatty acid in plants, palmitoyl-ACP (C16:0). Elongation of palmitoyl-ACP to stearoyl-ACP requires KAS II. Common plant unsaturated fatty acids are synthesized by desaturase. Desaturation of stearoyl-ACP by a soluble δ-9 desaturase form oleoyl-ACP (C18:1). Further desaturation takes place by action of membrane bound δ-12 desaturase to form linoleoyl-ACP (C18:2) and subsequently to α-linolenoyl-ACP by δ-15 desaturase.

Novel oil compositions are needed to meet the demand of the expanding oil business and changing market requirements. Genetic engineering provides the opportunity to diversify the use and the economic value of palm oil. Reported success in raising the levels of lauric acid and stearic acid in rapeseed oil provide an example of how in vitro gene technology can be used as a means for modifying both fatty acid chain length and the level of fatty acid unsaturation. Changing oil compositions by in vitro gene technology requires tools and techniques such as gene sequences of interest, a reliable transformation technique for ensuring stable integration and regulatory sequences for controlling expression of introduced genes. Thus, the identification of enzyme targets and useful nucleic acid sequences of such enzyme targets capable of modifying fatty acid compositions are needed. In oil palm, the focus of genetic engineering programs are in developing new varieties which have different oil characteristics such as being high in oleate. It is envisaged that higher oleate content will facilitate the entry of palm oil into the liquid oil market, as well as to provide oleic acid feedstock for the oleochemical industry. Significant progress has been made in the development of necessary techniques for the success of the genetic engineering efforts.

A reliable transformation system using biolistics technique for the oil palm has been established. In order to genetically engineer the oil palm for producing high oleic acid, the target genes need to be isolated and specifically expressed in the mesocarp. An important step in the synthesis of fatty acids appears to be the final condensation reaction by KAS II. Biochemical studies have indicated that the proportion of 16C/18C products of de novo synthesis of fatty acids in oil palm is control by KAS II activity. Thus, one strategy of genetic manipulation is to increase the expression of KAS II and to use antisense directed against the gene encoding palmitoyl-ACP thioesterase in order to reduce palmitic acid production and channel fatty acid synthesis toward 18 carbon acyl chains. Manipulation of the stearoyl ACP desaturase gene may also be required to cope with the possible accumulation of stearic acid so that more oleic acid can be produced. Isolation of some genes involved in fatty acid biosynthesis from oil palm mesocarp has already been achieved. These include isolation of the full-length complementary DNA (cDNA) clones of the δ 9 stearoyl ACP desaturase, palmitoyl ACP thioesterase, ACP as well as mesocarp specific promoter genes. The availability of the mesocarp specific promoter from oil palm is also important to ensure that the modifications are confine to storage lipid in the mesocarp without affecting lipid metabolism in other tissues which can otherwise leads to deleterious agronomic effects on the transgenic plants.

There is a need to isolate polynucleotide sequences encoding key components in the fatty acid biosynthesis pathway.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide sequences are referred to by a sequence identifier number (SEQ ID NO:). A summary of the sequence identifiers is provided in Table 1.

The present invention provides isolated genetic sequences which encode an enzyme having KAS II activity from a member of the Gramineae, Palmae, Juncaceae and Achenes families and more particularly from the Palmae family such as but not limited to *Elaeis guineensis* and *Elaeis oleifera*.

The isolation of KAS II encoding genetic sequences from oil palm is an important step towards the production of a transgenic oil palm family. In order to genetically engineer the oil palm to produce high levels of oleic acid, KAS II activity has to be up-regulated. Therefore, the full-length gene is required to be over-expressed. In accordance with the present invention, several techniques were employed for the isolation of KAS II genetic sequence from oil palm cDNA libraries constructed from mesocarp tissues as well total RNA. Partial length KAS II cDNA was first obtained by RT-PCR.

Rapid Amplification of cDNA Ends (RACE) was then used to isolate of 5' and 3' ends of KAS II genetic sequence. Assembly of the sequence fragments, including the 5' and 3' ends, allowed for the full-length sequence of the KAS II gene to be obtained. Subsequently, polymerase chain reaction (PCR) was used to amplify the complete cDNA clone encoding the protein having KAS II activity.

Northern analysis demonstrated that the KAS II encoding genetic sequence is expressed at low levels in various oil palm tissues including the mesocarp and kernel at different stages of development, leaves, germinated seedlings and flowers but not of roots. The expression pattern is similar to that of stearoyl-ACP desaturase and palmitoyl ACP thioesterase, which are other enzymes with direct involvement in mesocarp oil synthesis. Since the KAS II genetic sequence is also expressed in the mesocarp tissue of *E. guineensis*, the high yielding commercial oil-bearing species, modulation of KAS II activity alone or in conjunction with other enzymes such as plant thioesterases, desaturases and the like, will be very useful.

The present invention provides, therefore, in one aspect, the full-length polynucleotide sequence encoding an enzyme having KAS II activity from oil palm. Reference to "oil palm" in this instance includes any member of the Palmae family. The present invention extends, however, to any plant of the Gramineae, Juncaceae and Achenes family in addition to the Palmae family. This sequence has utility in generating genetically modified plants which are capable of modifying the composition and/or quantity of the fatty acids produced by plant cells.

Accordingly, the present invention provides an isolated nucleic acid molecule comprising a sequence of nucleotides encoding or complementary to a sequence encoding a peptide, polypeptide or protein having KAS II activity and comprising the nucleic acid sequence encoded by the nucleotide sequence as set forth in SEQ ID NO: 2 or SEQ ID NO: 1, or a nucleotide sequence encoded by it, or having at least about 70% similarity thereto after optimal alignment.

In a related embodiment, the present invention provides an isolated nucleic acid molecule encoding a peptide, polypeptide or protein, said nucleic acid molecule comprising a sequence of nucleotides as set forth in SEQ ID NO: 1 or a nucleotide sequence having at least about 70% identity thereto after optimal alignment or a nucleotide sequence capable of hybridizing to SEQ ID NO: 1 or its complementary form under low stringency conditions.

The availability of the polynucleotide sequences of the present invention makes alterations to the expression of an endogenous or heterologous KAS II gene possible. The nucleotide sequence set forth herein would facilitate the production of chimeric genetic constructs which can be inserted into vectors for the transformation of eukaryotic or prokaryotic cells, or any multicellular structures generated from such cells. Such genetic constructs may be used to increase the expression of KAS II genetic sequences in plants or other organisms. Alternatively, constructs may be used to down-regulate or knock out KAS II genetic sequences in plants or other organisms or otherwise down-regulate expression of KAS II genetic sequences.

A particularly preferred embodiment of the instant invention provides an isolated nucleic acid molecule comprising a sequence of nucleotides substantially as set forth in SEQ ID NO: 1. Furthermore, although the present invention is particularly exemplified with respect to oil palm plants, this is done with the understanding that the instant invention extends to any monocotyledonous plant. Reference herein to a monocotyledonous plant includes any member of the Gramineae, Palmae, Juncaceae and Achenes families such as but not limited to cereals, grasses, maize, sugar cane, oats, wheat, barley as well as oil palm.

Once a chimeric genetic construct has been cloned into a vector and transformed into target cell, the exogenously introduced KASII coding sequence of the present invention may be translated by the cell to cause the production of the encoded protein, in this case, a fatty acid biosynthetic enzyme. The action of the introduced protein may effect a desirable phenotype that would otherwise not be present. In this regard, particularly preferred phenotypes include an alteration of the total quantity, or relative amounts of fatty acids produced by the cell or a higher plant or organism comprising the cell or a higher plant or organism comprising the cell. In a particularly preferred embodiment, the introduced KAS II gene is over-expressed by a plant cell, particularly an oil palm plant cell, wherein the over-expression of a KAS II genetic sequence leads to an increase in the total amount of fatty acids, or an increase in the relative proportion C18 to C16 fatty acids, produced by the oil palm.

Alternatively, the KAS II genetic sequence is used in co-suppression to generate, for example, RNAi or complexes comprising same involved in gene silencing events.

The present invention further provides a vector for use in generating genetically modified plants exhibiting altered phenotypes, the plants producing a polypeptide having an amino acid sequence encoded by the nucleotide sequence as set forth in SEQ ID NO: 2 or SEQ ID NO: 1, or an amino acid sequence amino acid sequence encoded by the nucleotide sequence having at least 70% similarity to the SEQ ID NO: 2 or SEQ ID NO: 1 after optimal alignment.

Another aspect of the invention provides an isolated, peptide, polypeptide or protein having KAS II activity or a biologically active fragment thereof, the polypeptide comprising an amino acid sequence encoded by the nucleotide sequence set forth in SEQ ID NO: 2 or SEQ ID NO: 1, or an amino acid sequence having at least 70% similarity to the sequence encoded by the nucleotide sequence set forth in SEQ ID NO: 2 or SEQ ID NO: 1.

The KAS II polynucleotide sequence of the present invention may be used to alter the phenotype of a cell or organism or plant comprising the cell or the sequence or part thereof may be used in a diagnostic manner. For example, the genetic sequence encoding KAS II or part thereof or a 3' or 5' non-coding portion thereof may be used as or to generate probes or primers to identify particular oil palm cultivars with high KAS II activities or levels and, hence, produce high quantities of valuable C18 fatty acids. Although palm oil is the plant exemplified herein, as noted above, the present invention extends to any plant of the Gramineae, Palmae, Juncaceae and Achenes families.

In yet another aspect, the present invention provides an isolated polynucleotide defining a 5' or 3' regulatory region and comprising a sequence of nucleotides as set forth in SEQ ID NO: 3 or SEQ ID NO: 4, respectively, or a sequence having at least about 70% identity thereto after optimal alignment or a nucleotide sequence capable of hybridizing to SEQ ID NO: 3 or SEQ ID NO: 4, respectively or its complementary form under low stringency conditions.

The nucleic acid sequences disclosed herein may be applied to alter or modulate a particular trait/phenotype of a target cell or tissue in a plant, animal or bacterial cell and preferably a plant of the Gramineae, Palmae, Juncaceae and Achenes families, preferably of the family Palmae and even more preferably, the E. guineensis or E. oleifera.

Particularly desired phenotypes contemplated herein include increased or decreased total fatty acid yield and/or an increased proportion of stearic acids (C18:0) and subsequently oleic acids (C18:1).

Still another aspect of the present invention contemplates a method for generating a plant with a modified phenotype, the method comprising introducing into the genome of a plant cell or group of plant cells a genetic construct comprising a polynucleotide promoter region or functional equivalent thereof operably linked to a nucleotide sequence as set forth in SEQ ID NO: 2 or SEQ ID NO: 1, which encodes a KAS II polypeptide or a polypeptide having an amino acid sequence having at least 70% similarity to the sequence encoded by the nucleotide sequence set forth in SEQ ID NO: 2 or SEQ ID NO: 1 after optimal alignment.

In a related aspect of the present invention, there is provided a method for generating a plant with a modified phenotype, the method comprising introducing into the genome of a plant cell or group of plant cells a genetic construct comprising a polynucleotide promoter region or functional equivalent thereof operably linked to a nucleotide sequence as set forth in SEQ ID NO: 1 or a polynucleotide sequence having at least about 70% identity thereto after optimal alignment or a polynucleotide sequence capable of hybridizing to SEQ ID NO: 1 under low stringency conditions.

The present invention extends to and encompasses bacterial cells, fungal cells, plant cells, plants and parts of plants, such as flowering and reproductive parts including seeds, transformed with one or more genetic constructs as set forth herein.

Preferably, the transformed plant or part of said plant is of the genus *Elaeis* and in particular *E. guineensis* and *E. oleifera*.

Preferably, the transformed bacteria are *Escherichia coli*.

A summary of sequence identifiers used throughout the subject specification is provided in Table 1.

TABLE 1

Summary of sequence identifiers

Nucleotide sequence of central part of gene encoding KAS II enzyme (KasEg7a) from oil palm

SEQ ID NO:1

```
CATTATGCTGAGTGATATCTTTTTTTTTTGCCTTGCTCACAAGTTATTGCCACATC
CTGAAGGTAGAGGGGTTATCCTTTGTATTGAAAATGCACTAGCAGATGCAGGAG
TAGCAAAGGAAGACATTAATTATGTAAATGCCCATGCAACATCGACGCAGATGG
GTGATTTGAAGGAATTTGAAGCTCTCAACCGCTGTTTTGGTCAGAACCCTCAGCT
TAGAGTAAACTCAACAAAGTCAATGACGGGTCATCTGCTAGGAGCTGCAGGTGG
AATAGAAGCTGTGGCTGCTATACAAGCTATAAGGACTGGTTGGGTCCACCCAAA
TATCAATTTAGACAACCCGGAGAAAAATGTGGATGTCAGCATTCTAGTGGGATC
ACAAAAAGAGAGATGTGATGTAAAGGTGGCGTTGTCGAACTCGTTCGGATTCGG
TGGGCATAACTCAA:
```

Nucleotide sequence of full-length oil palm KAS II (KasEg2C)

SEQ ID NO:2

```
AAAGCTCGTGCCTTTTCTTCCNTAAGATCGATGCCATCTTTCATTCCCTTCGTCAG
CTTTTCTCCCCTCCCAAAACCTTTCGCCATCCTCTTCGACCCGTTTCCTCCTTCCC
AAAATCGCATATTTTCTCGTTAAAAATCGCTCTTTTTTCTCTCGCTGTTTCTTAGT
CCGCTCTTTGAGATCTTGAATTCGCCCTTGGCCTCTTCTCCTCTCTCAACTTCGAT
CGGAACGTTCTCGAGTTCTAGCTTCTGCCCGCTCCGCTTTTGGAGCTTCTCTCCTC
CCTTATTCCGGCTTTGCTCTGTTCTTCTCCAATGGCGGGCGCCGCCGTGGCCTCGC
CGCTGTGCACGTGGCTGGTGGCGGCGTGCATGACGGTGGCGTGCGACAAGGAGT
GGCCGCTGGGGCCGGGGAGTGCGTCCCCCGGCGGAGGTGGCGGAGGGCGTCGC
TCTCCGGCGGCGTGGGCCGGGCTTCGCCGAGGCGGCTGATCTCGGCCTTCTGTGG
GGCGGGATCCAGGGGTTGATGAGCTCGTGCCTGGCCTTCGAGCCCTGCGCCGA
GTTCTACAGCTCGAGAAATGGGTCGGCGTTCTTTGGGGGGATGGCTTCTCTCTG
CTTGGGCGGCAGAATGCTGAGACTACTCGAAGGCAGCGAAGGGGTGCCCGTTCT
TCTCCTTCTTCTGTTGCAGGAAAAGTCATGTCCATTGCTGTGCAGCCTGAAAAGA
AGGTTGCAGAGAAAGAGAGAACCCAAACCAAACAGCGGAGGGTTGTTGTGACG
GGAATGGGTGTGGTGACTCCATTAGGCCATGATCCAGATCATTTCTATGAAGAGC
```

TABLE 1-continued

Summary of sequence identifiers

TCCTCAAGGGTGTTAGTGGCATAAGTGAAATAGAAACATTCGACTGTTCCAGTTA
TCCAACGAGGATTGCAGGAGAAATTAAATCTTTTTCCTCGGATGGATGGGTGGCA
CCAAAACTATCCAAAAGGATGGACAAGTTTATGCTTTACTTACTTACTGCTGGCA
AGAAAGCATTGGAAAATGGTGGACTTACAGAAGAGGCTATGAGTTGGTTGGATA
AGGAAAGATGTGGAGTTCTCATTGGGTCTGCAATGGGTGGAATGAAAGTTTTTA
ATGATGCAATTGAGGCTTTAAGGATCTCGTACAAGAAGATGAACCCCTTTTGTGT
ACCCTTTGCAACTACGAATATGGGCTCTGCAATGCTTGCAATGGATCTAGGTTGG
ATGGGCCCAAACTATTCTATTTCTACTGCATGTGCAACTAGCAACTTCTGTATTTT
GAATGCAGCAAACCATATTATAAGAGATGAAGCTGATGTGATGCTTTGTGGTGG
CTCTGATGCAGCAATTATACCAATTGGATTGGGGGGTTTTGTGGCATGCGGAGCA
CTCTCGCAGAGAAATAGTGATCCGACTAAAGCGTCACGGCCTTGGGACATTGAT
CGTGATGGATTCGTGATGGGGGAGGGGGCTGGCGTGCTTCTACTGGAAGAATTA
GAGCATGCTAAGCAAAGAGGAGCAAATATCTATGCTGAATTTCTTGGGGGAAGC
TTCACATGTGATGCTTACCACATGACTGAGCCACATCCTGAGGGGGCAGGCATTG
CTCTTTGCATTGAGAACGCATTAGCACAAGCAGGGGTAGCCAAAGAAGATGTTA
ATTATGTAAATGCTCATGCAACTTCAACACCTGCTGGTGACCTAAAAGAGTATCA
AGCTCTCATTCGTTGTTTTGGGCAGAATCCTGAGCTGAGAGTGAACTCTACAAAA
TCAATGATTGGTCACCTACTAGGAGCTTCTGGTGCGGTGGAAGCTGTTGCTGCAA
TTCAGGCAATTCGAACAGGGTGGGTCCATCCAAATGTCAATCTCGAAAACCCAG
AAAAAAGTGTGGATATAAATGTGCTGGTGGGCTCGAAAAAAGGAAAAGGTTGG
ACGTCAATAAGCTGGTGGGCTCAAAGAAGGAAAGATTGGATGTGAAGGTGGCCC
TGTCAAACTCTTTTGGCTTTGGTGGCCACAACTCGTCTATCCTGTTTGCACCCATAC
AAATAAGCATCAGCTATGGGCCTACAAAAGCATAAGGGCGAATTCCATCTTACA
TGTAATTTGTATCAGAAATGACTGTGTGGTGCTTATGTTTTTATTTGGCACCAACA
TCTTGATCATATGGAATTGGTCTAGATGCCGTTATAGCTCATAATAGAATGGTAT
ATAGTGCACTACTTTCAAAAAAAAAAAAAAACTCAGG:

Nucleotide sequence of 5'-UTR
                                                SEQ ID NO:3
CCACTACAAGGTAAAGAATAAAAAAGTTGGTTTAACTTTAATCACCTTTTTTTCT
TTCCCCTCTTTGCAAGTTGGCGATGGCTTTCGCCACTCCCCTTGGTTTCGCCAAAG
CTCGTGCCTTTTCTTCCTAAGATCGATGCCATCTTTTCATTCCCTTCGTCAGCTTTTC
TCCCCTCCCAAAACCTTTCGCCATCCTCTTCGACCCGTTTCCTCCTTCCCAAAATC
GCATATTTTCTCGTTAAAAATCGCTCTTTTTTCTCGCTGTTTCTTAGTCCGCTCT
TTGAGATCTTGAATCCCTTCTTGGCCTCTTCTCCTCTCTCAACTTCGATCGGAACG
TTCTCGAGTTCTAGCTTCTGCCCGCTCCGCTTTTGGAGCTTCTCTCCTCCCTTATTC
CGGCTTTGCTCTGTTCTTCTCCA:

Nucleotide sequence of 3'-UTR
                                                SEQ ID NO:4
ATAAGCTGGTGGGCTCAAAGAAGGAAAGATTGGATGTGAAGGTGGCCCTGTCAA
ACTCTTTTGGCTTTGGTGGCCACAACTCGTCTATCCTGTTTGCACCATACAAATAA
GCATCAGCTATGGGCCTACAAAAGCATCAAGGTCATCTTACATGTAATTTGTATC
AGAAATGACTGTGTGGTGCTTATGTTTTTATTTGGCACCAACATCTTGATCATATG
GAATTGGTCTAGATGCCGTTATAGCTCATAATAGAATGGTATATAGTGCACTACT
TTCAAAAAAAAAAAAAAACTCAGG:

Nucleotide sequence of KasU86m (FIG. 2)
                                                SEQ ID NO:5
GCCCTTCTCTCGCAGAGAAATAGTGATCCGACTAAAGCGTCACGGCCTTGGGAC
ATTGATCGTGATGGATTCGTGATGGGGGAGGGGGCTGGCGTGCTTCTACTGGAA
GAATTAGAGCATGCTAAGCAAAGAGGAGCAAATATCTATGCTGAATTTCTTGGG
GGAAGCTTCACATGTGATGCTTACCACATGACTGAGCCACATCCTGAGGGGGCA
GGCATTGCTCTTTGCATTGAGAACGCATTAGCACAAGCAGGGGTAGCCAAAGAA
GATGTTAATTATGTAAATGCTCATGCAACTTCAACACCTGCTGGTGACCTAAAAG
AGTATCAAGCTCTCATTCGTTGTTTTGGGCAGAATCCTGAGCTGAGAGTGAACTC
TACAAAATCAATGATTGGTCACCTACTAGGAGCTTCTGGTGCGGTGGAAGCTGTT
GCTGCAATTCAGGCAATTCGAACAGGGTGGGTCCATCCAAATGTCAATCTCGAA
AACCCAGAAAAAAGTGTGGATATAAATGTGCTGGTGGGCTCGAAAAAAGGAAA
AGGTTGGATGTGATAAGCTGGTGGGCTCAAAGAAGGAAAGATTGGATGTGAAGG
TGGCCCTGTCAAACTCTTTTGGCTTTGGTGGCCACAACTCGTCTATCCTGTTTGCA
CCATACAAATAAGCATCAGCTATGGGCCTACAAAAGCATCAAGGTCATCTTACA
TGTAATTTGTATCAGAAATGACTGTGTGGTGCTTATGTTTTTATTTGGCACCAACA
TCTTGATCATATGGAATTGGTCTAGATGCCGTTATAGCTCATAATAGAATGGTAT
ATAGTGCACTACTTTCAAAAAAAAAAAAAAACTCAGG:

Nucleotide sequence of KasU26R (FIG. 3)
                                                SEQ ID NO:6
GCCCTTGGACACTGACATGGACTGAAGGAGTAGAAAATTGCAGGAGAAATTAAT
TTTTTTTCAACAGATGGATTGGTGGCACCTAAATTATCTAAACGAATGGCAAATT
CATGCTCTATTTACTTATTGCTGGAAAGAAAGCATTAGCCAATGGTGGGGTTATT
GAAGAGGTCATGAGTCAGCTTGACAAGGCAAAATGCGGAGTGCTCATAGGCTCT
GCGATGGGTGGAATGAAGGTTTTTAATGATGCCATCGAAGCTTTAAGGGTCTCAT
ATAAGAAGATGAATCCATTTTGTGTTCCATTTGCAACGACAAACATGGGTTCTGC
AATCCTTGCCATGGATCTGGGTTGGATGGGCCCAAATTACTCTATTTCAACTGCT
TGTGCTACAAGCAATTTCTGTATCCTGAATGCAGCAAACCATATAATAAGAGGG
GAAGCGGATGTGATGCTTTGTGGTGGATCAGATGCTGCTATTATACCAATTGGAC TABLE 1-continued Summary of sequence identifiers TGGGGGGTTTTGTTGCTTGCAGAGCACTCTCGCAGAGAAATAGTGATCCGACTAA
AGCGTCACGGCCTTGGGACATTGATCGTGATGGATTCGTGATGGGGGAGGGGGC
TGGCGTGCTTCTACTGGAAGAATTAGAGCATGCTAAGGGCGAATTCGTTTAAACC
TGCAGGACTAGTCCCTTTAGTGAGGGTTAATTCTGAGCTTGGCGTAGGCAGGTCA
ACGTTTTAACCTC:

Nucleotide sequence of KasU11/12
                                                 SEQ ID NO:7
CGGCGTGAATTGTAATACGACTCACTATAGGGCGAATTGAATTTAGCGGCCGCG
AATTCGCCCTTGGACACTGACATGGCTGAAGGACTACAAATCGTGACAGGGATG
GGTGTGGTGACTCCACTGGGCGTTGATCCTGATATCTTCTACAATAACCTTCTTG
ATGGTGTCAGTGGTATAAGTCAAATTGAAACATTTGACTGTACCAACTATCCAAC
AAGAATTGCAGGAGAAATTAAATCTTTTTCAACAGATGGATTGGTGGCACCTAA
ATTATCTAAACGAATGGACAAATTCATGCTCTATTTACTTATTGCTGGAAAGAAA
GCATTAGCCAATGGTGGGGTTACTGAAGAGGTCATGAGTCAGCTTGACAAGGCA
AAATGCGGAGTGCTCATAGGCTCTGCGATGGGTGGAATGAAGGTTTTTAATGAT
GCCATCGAAGCTTTAAGGGTCTCATATAAGAAGATGAATCCATTTTGTGTTCCAT
TTGCAACGACAAACATGGGTTCTGCAATCCTTGCCATGGATCTGGGTTGGATGGG
CCCAAATTACTCTATTTCAACTGCTTGTGCTACAAGCAATTTCTGTATCCTGAATG
CAGCAAACCATATAATAAGAGGGGAAGCGGATGTGATGCTTTGTGGTGGATCAA
ATGCTGCAAGGGCGAATTCCTTTAAACCTGCAGGACTAGTCCCTTTAGTGAGGGG
TAATTCTTGACCTTGGCGTAAATCATCGGCCATAGCCTGGTTACCCTGCGTCCAA
AATGGTTTTTCCCCTACCAAAATTTCCCTCAACATTTCCAAACCCCGGAAACCAT
AAANGGTTGAAAACCCCNGGGGGGGGCCTTAATTGAAGTGGAACCTCACTTCCC
AATTTAATTTGCCTTTGCCCCTCACTTGCCCCCTTTTTCCCAATCCGGG:

Nucleotide sequence of KasU24a (FIG. 5)
                                                 SEQ ID NO:8
CCACTCACAAGGCTGTAAAGAATAAAAAAGTTAGGTTTAAACTTTAAATCACCTT
TTTATATCTATATCCCCTCTTTNGCAAGTTGGCGATGGCTTTCGCCACGTCCCCTT
GGTTTCGCCAAAGCTCGTGCCTTTTCTTCCGTAAGATCGATGCCATCTTTCATTCC
CTTCGTCAGCTTTTCTCCCCTCCCAAAACCTTTCGCCATCCTCTTCGACCCGTTTC
CTCCTTCCCAAAATCGCATATTTTCTCGTTAAAAATCGCTCTTTTTTCTCTCGCTG
TTTCTTAGTCCGCTCTTTGAGATCTTGAATCCCTTCTTGGCCTCTTCTCCTCTCTCA
ACTTCGATCGGAACGTTCTCGAGTTCTAGCTTCTGCCCGCTCCGCTTTTGGAGCTT
CTCTCCTCCCTTATTCCGGCTTTGCTCTGTTCTTCTCCAATGGCGGGCGCCGCCGT
GGCCTCGCCGCTGTGCACGTGGCTGGTGGCGGCGTGCATGACGGTGGCGTGCGA
CAAGGAGTGGCCGCTGGGGCCGGGGAGTGCGTCCCCCCGGCGGAGGTGGCGGA
GGGCGTCGCTCTCCGGCGGCGTGGGCCGGGCTTCGCCGAGGCGGCTGATCTCGG
CCTTCTGTGGGCGGGGATCCAGGGGTTGATGAGCTCGTGCCTGGCCTTCGAGCC
CTGCGCCGAGTTCTACAGCTCGAGAAATGGGTCGGCGTTCTTTGGGGGGATGG
CTTCTCTCTGCTTGGGCGGCAGAATGCTGAGACTACTCGAAGGCAGCGAAGGGG
TGCCCGTTCTTCTCCTTCTTCTGTTGCAGGAAAAGTCATGTCCATTGCTGTGCAGC
CTGAAAAGAAGGTTGCAGAGAAAGAGAGAACCCAAACCAAACAGCGGAGGGTT
GTTGTGACGGGAATGGGTGTGGTGACTCCATTAGGCCATGATCCAGATCATTTCT
ATGAAGAGCTCCTCAAGGGTGTTAGTGGCATAAGTGAAATAGAAACATTCGACT
GTTCCAGTTATCCAACGAGGATTGCAGGAGAAATTAAATCTTTTTCCTCGGATGG
ATGGGTGGCACCAAAACTATCCAAAAGGATGGACAAGTTTATGCTTTACTTACTT
ACTGCTGGCAAGAAAGCATTGGAAATGGTGGACTTACAGAAGAGGCTATGAGT
TGGTTGGATAAGGAAAGATGTGGAGTTCTCATTGGGTCTGCAATGGGTGGAATG
AAAGTTTTTAATGATGCAATTGAGGCTTTAAGGATCTCGTACAAGAAGATGAAC
CCCTTTTGTGTACCCTTTGCAACTACGAATATGGGCTCTGCAATGCTTGCAATGG
ATCTAGGTTGGATGGGCCCAAACTATTCTATTTCTACTGCATGTGCAACTAGCAA
CTTCTGTATTTTGAATGCAGCAAACCATATTATAAGAGATGAAGCTGATGTGATG
CTTTGTGGTGGCTCTGATGCAGCAATTATACCAATTGGATTGGGG GGTTTTGTGG
CATGCGGAGCACTTTCAC:

Kas sense primer P1 (KasP1) sequence:
                                                 SEQ ID NO:9
5'-GCCACATCCTGAAGGTAGAG-3'

Kas antisense primer P2 (KasP2) sequence:
                                                 SEQ ID NO:10
5'TGAGTTATGCCCACCGAATC-3'

Gene-specific primer GKAS1:
                                                 SEQ ID NO:11
5'CACCAGATGGTGTTGAAGTTGCATGAGC-3'

Nested primer GKAS2 GKAS2
                                                 SEQ ID NO:12
5'-CCTGATTCTGCTAGCGCCTTCTCAATG C-3'

Gene-specific primer 1 GKAS 20F:
                                                 SEQ ID NO:13
5'-CTCTCGCAGAGAAATAGTGATCCGACTAAAGCGTCACGGCCT-3'

TABLE 1-continued

Summary of sequence identifiers

Gene-specific primer 2 GKAS21F
SEQ ID NO:14
5'-GGGCTGGCGTGCTTCTACTGGAAGAATTAGAGCATGCT-3'

Gene-specific primer 1 GKAS1 Sequence:
SEQ ID NO:15
5'-TGTGGCTCAGTCATGTGGTAAGCATCACATGTGAAGC-3'

Gene-specific primer 2 GKAS10 Sequence:
SEQ ID NO:16
5'-AGCATGCTCTAATTCTTCCAGTAGAAGCACGCCAGCCC-3'

Gene-specific primer 1 GKAS11 Sequence:
SEQ ID NO:17
5'-GCC GTG ACG CTT TAG TCG GAT CAC TAT TTC TCT GCG AGA G-3'

Gene-specific primer 2 GKAS12 Sequence:
SEQ ID NO:18
5'-GCAGCATCTGATCCACCACAAAGCATCACA-3'

Gene-specific primer 1 GKAS7 Sequence:
SEQ ID NO:19
5'-CAACATCCCAGGGGCGAGAAGCTTTCACTG-3'

Gene-specific primer 2 GKAS8 Sequence:
SEQ ID NO:20
5'-GTGAAAGTGCTCCGCATGCCACAAAACC-3'

Primer GKAS13
SEQ ID NO:21
5'-GGGATGGGTGTGGTGACTCCACTGGGCGTTGAT CCT GA-3'

Primer PU1 PU1:
SEQ ID NO:22
5'-ATGGACAAGTTTATGCTTTACTTACTT-3'

Primer GKAS27
SEQ ID NO:23
5'-ATGCTTTTGTAGGCCCATAGCTGATGC-3'

Primer GKAS28
SEQ ID NO:24
5'-TTCCATATGATCAAGATGTTGGTGCC-3'

Primer GKAS29
SEQ ID NO:25
5'-TGAGATCGATGCCATCTCTCATTCCCTTCGTC-3'

Primer GKAS30
SEQ ID NO:26
5'-TCTTGGCCTCTTCTCCTCTCTCAACTTC-3'

A list of abbreviations used herein is provided in Table 2.

TABLE 2

Abbreviations

| ABBREVIATION | DESCRIPTION |
| --- | --- |
| RACE | rapid amplification cDNA ends |
| KAS II | β-ketoacyl ACP synthase II |
| ACP | acyl carrier protein |
| UTR | untranslated region |
| PCR | polymerase chain reaction |
| RT-PCR | reverse transcriptase PCR |

Single and three letter abbreviations used throughout the specification are defined in Table 3.

TABLE 3

Single and three letter amino acid abbreviations

| AMINO ACID | THREE-LETTER ABBREVIATION | ONE-LETTER SYMBOL |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |

TABLE 3-continued

Single and three letter amino acid abbreviations

| AMINO ACID | THREE-LETTER ABBREVIATION | ONE-LETTER SYMBOL |
|---|---|---|
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

BRIEF DESCRIPTION OF THE DRAWINGS

FIG. 1 is a representation showing the nucleotide sequence of oil palm encoding KAS II gene, designated KasEg7a (SEQ ID NO: 1). Degenerate oligonucleotide primers (P1 and P2) were designed using a comparison of the KAS II genes from rice and other plants. The central part of the oil palm KAS II gene, designated KasEg7a, was first amplified by RT-PCR from 17 week mesocarp using these primers, cloned and sequenced. For this, first strand cDNA synthesis was carried out using homopolymer tail poly (dT) and Superscript II RNase H⁻ Reverse Transcriptase. Sense primer (P1) was subsequently introducing using Advantage Polymerase Mix (Clontech) during primary PCR. The antisense primer (P2) together with the primary PCR product were used in the secondary PCR reaction to ensure amplification of the desired sequence. The product from secondary PCR reaction which is about 450 bp was cloned and sequenced.

FIG. 2 is a representation showing the complete sequence of KasU86m (SEQ ID NO: 5) sequenced from both directions using M13 forward and reverse reaction primer. The KasU86m has the stop codon and coded for a peptide 159 amino acids in length which was 80% and 77% identical to the deduced amino acid of oil palm and *Cuphea wrightii*, respectively.

FIG. 3 is a representation showing the complete sequence of KasU26R (SEQ ID NO: 6).

FIG. 4 is a representation showing the complete sequence of KasU26R (SEQ ID NO: 6) sequenced from both directions using M13 forward and reverse reaction primer aligned with the cDNA sequence of KasU86m (SEQ ID NO: 5). The sequence obtained showed further 5' extension to the original cDNA sequence of KasU86m. It was found that approximately 120 bp of the 3' terminal region of the 5' RACE product (Kas26RC) overlapped with the 5' terminal region of the 3' RACE product (KasU86m). Within the overlapping region, the two sequences were approximately 100% homologous.

FIG. 5 is a representation showing the complete sequence of KasU24a (SEQ ID NO: 8) obtained from the 5' RACE. The size is approximately 1.5 kb and sequencing analysis showed the clone has the start codon and thus produced a further 5' extension to the original KasU11/12 clone (SEQ ID NO: 7).

FIG. 6 is a representation showing the sequence obtained from the method of FIG. 5 showed further 5' extension to the original cDNA sequence of KasU86m (SEQ ID NO: 5). The first methionine at the 5' end of the cloned 5' RACE product is a likely coding region start codon. It was found that approximately 485 bp of the 3' terminal region of the second 5' RACE product (SEQ ID NO: 8) overlapped with the 5' terminal region of the first 5' RACE product (SEQ ID NO: 6). Within the overlapping region, the two sequences were approximately 84% homologous.

FIG. 7 is a representation showing the nucleotide sequence of KasEg2C (SEQ ID NO: 2).

FIG. 8 is a representation showing strong conserved nucleotide residues between KasEg2C (SEQ ID NO: 2) and other KAS II sequences from the GenBank database.

DETAILED DESCRIPTION OF THE PREFERRED EMBODIMENT

Figure 9:
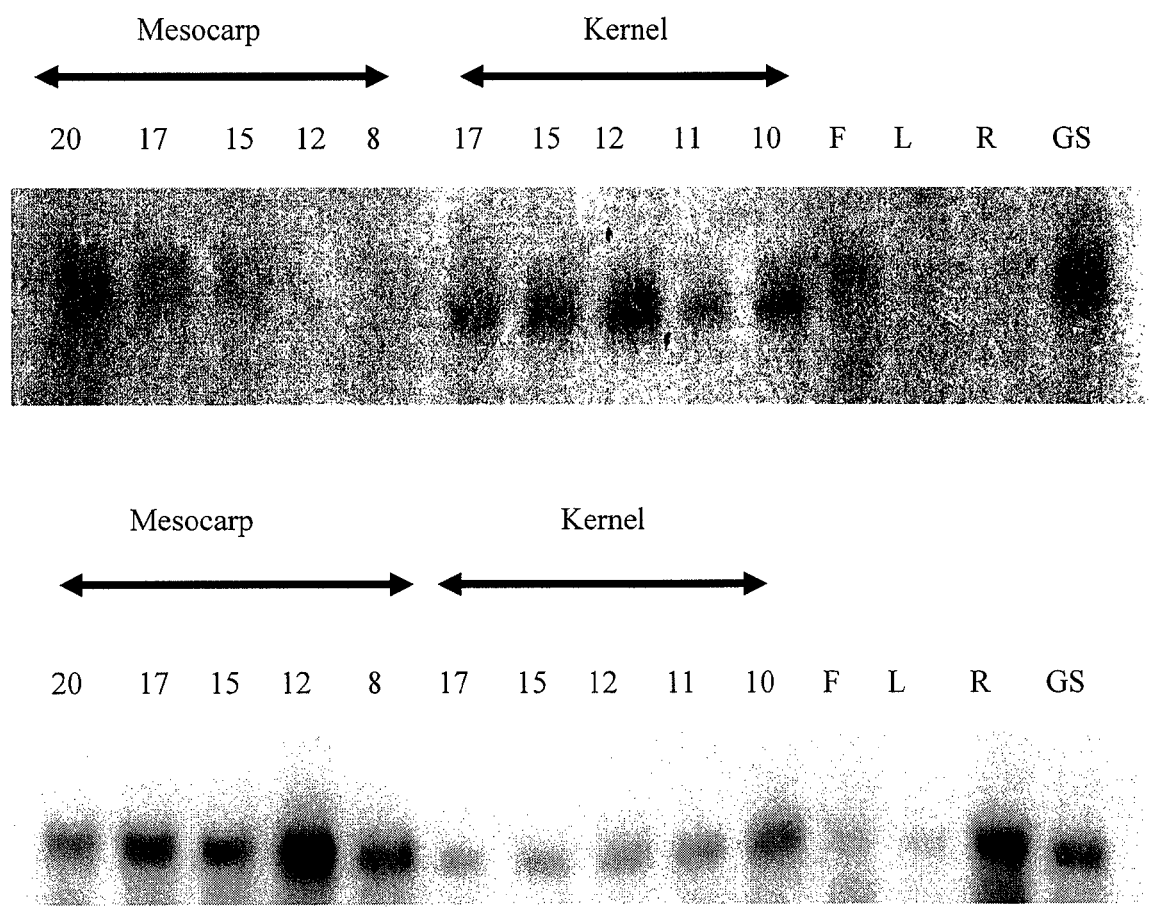
FIG. 9. Expression pattern of KASII gene in different oil palm tissues; mesocarp, kernel, flower (F), spear leaf (L), roots (R) and germinated seedlings (GS). The blot was hybridized with $^{32}$P-labelled probe prepared using entire insert of clone KasEg2C (full-length KASII). The membrane was reprobed with ribosomal DNA to check for equal loading of RNA samples. WAA=weeks after anathesis; F=Flower; L=Leaves; R=roots; GS=germinated seedlings.

The present invention provides an isolated nucleic acid molecule comprising a polynucleotide sequence encoding a polypeptide having KAS II activity from an oil palm plant.

Initially, PCR was used to clone a partial length cDNA of the KAS II genetic sequence from total RNA. Initial amplification involved degenerate oligonucleotide primers that were designed based on conserved regions of rice KAS II (AU031953). The first partial length oil palm KAS II genetic sequence was obtained by RT-PCR and the size was about 480 bp and displayed homology to other KAS II genes in GenBank. Different methods were used to amplify the 5' and 3' end regions. RACE was used to amplify sequence further up-stream and down-stream of the KAS II partial sequence as well as the stop and start codons. For RACE experiments, gene specific primers were designed based on the partial sequence of the oil palm KAS II genetic sequence as well as the oil palm KAS II genetic sequence in GenBank (AF220453). The 5' and 3' end region (including the start and stop codons) of the full-length KAS II genetic sequence were captured by 5' and 3' RACE. The overlapping region of the products showed total homology with the partial length of KAS II.

PCR was used to amplify the full-length cDNA clone of the KAS II genetic sequence. The full-length cDNA clone was isolated by PCR from 17-week *E. guineensis* mesocarp total RNA extract using primers designed based on consensus sequence and the size is about 2.0 kb. The sequence of KAS II genetic sequence from *E. guineensis* is about 80-90% identical at the nucleotide levels and 60-70% identity at amino acid level with other KAS II genetic sequences in GenBank. Alignment analysis also showed there was a distinct variation between oil palm KAS II and the KAS II from other plants. Oil palm KAS II has a 3' untranslated non-coding region which is entirely different from other plant KAS II genes. A distinct variation was also observed at the 5' region.

Accordingly, one aspect of the present invention provides an isolated nucleic acid molecule comprising a sequence of nucleotides encoding or complementary to a sequence encoding a peptide, polypeptide or protein having KAS II activity comprising the amino acid sequence encoded by the SEQ ID NO: 2 or SEQ ID NO: 1 or an amino acid sequence having at least about 70% similarity thereto after optimal alignment.

In a related embodiment, the present invention provides an isolated nucleic acid molecule encoding a peptide, polypeptide or protein having KAS II activity, said nucleic acid molecule comprising a sequence of nucleotides as set forth in SEQ ID NO: 1 or a nucleotide sequence having at least about 70% identity thereto after optimal alignment or a nucleotide sequence capable of hybridizing to SEQ ID NO: 1 or its complementary form under low stringency conditions.

Reference herein to a "nucleic acid molecule" includes reference to DNA, cDNA or RNA (e.g. mRNA and rRNA) as well as DNA/DNA and DNA/RNA hybrids. A nucleic acid molecule may also be referred to herein inter alia as a genetic molecule, genetic sequence, nucleotide sequence or polynucleotide sequence. Reference to a DNA molecule includes genomic DNA. In one preferred embodiment, the nucleic acid molecule is a cDNA molecule. The term "gene" may also be used to cover a cDNA molecule or genomic sequence encoding the KAS II polypeptide. The terms "peptide", "polypeptide" and "protein" are used interchangeably herein.

By "isolated" is meant material that is substantially or essentially free from components that normally accompany it in its native state. For example, an "isolated nucleic acid molecule" as used herein refers to a nucleic acid molecule, which has been purified from the sequences which flank it in a naturally occurring state, e.g. a DNA fragment which has been removed from the sequences which are normally adjacent to the fragment. Preferably but not necessarily, an isolated nucleic acid molecule is in a form capable of being sequenced (i.e. sequenciably pure).

The term "nucleic acid molecule" or other terms such as "genetic molecule" or "polynucleotide sequence" of the present invention encompasses derivatives including fragments, portions, parts, mutants and homologs thereto.

By "derivative" also includes any single or multiple nucleotide deletions, additions or substitutions as well as mutants, fragments, portions or parts of the isolated nucleic acid molecule. All such deletions, additions, substitutions, mutants, fragments, portions, or parts are encompassed by the term "derivative" and are encompassed by the term "nucleic acid molecule" or similar term such as "polynucleotide sequence". Particularly useful derivatives include alterations to the 5' end portion of the polynucleotide sequence or the 3' end portion or a nucleotide sequence spanning the 5' and 3' portions. Synthetic derivatives may also be useful, for example, in diagnostic assays. A derivative also conveniently includes a nucleotide sequence having less than 100% identity with the nucleotide sequence set forth in SEQ ID NO: 1.

Generally, however, the derivative is capable of hybridizing to SEQ ID NO: 1 or a complementary form under low stringency conditions and has at least 70% identity to SEQ ID NO: 1 after optimal alignment.

Examples of percentage identity include 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% identity to SEQ ID NO: 1.

Reference herein to a "polypeptide" includes reference to a peptide or protein. The term "enzyme" may also be used. The polypeptide of the present invention is produced via expression of the nucleotide sequence herein disclosed and functions during fatty acid biosynthesis as it has KAS II activity. A polypeptide having KAS II activity includes a naturally occurring KAS II enzyme, a recombinant KAS II enzyme as well as a genetically engineered protein or mutated protein exhibiting KAS II activity.

Higher plants synthesize fatty acids via a common pathway. In developing seeds, de novo production of fatty acids takes place in the proplastids. These fatty acids are attached to triacylglycerides and stored as a source of energy for further germination. The first step is the formation of acetyl-ACP from acetyl-CoA and ACP catalyzed by the enzyme, acetyl-CoA:ACP transacylase. Elongation of acetyl-ACP to 16- and 18-carbon fatty acids involves a series of four reactions; condensation with a two-carbon unit from malonyl-ACP to form a β-ketoacyl ACP (β-ketoacyl ACP synthase), reduction of the keto-function to an alcohol (β-ketoacyl ACP reductase), dehydration to form enoyl-ACP (β-hydroxyacyl-ACP dehydrase) and finally reduction of the enoyl-ACP to form the elongated saturated acyl-ACP (enoyl-ACP reductase). β-ketoacyl ACP synthase I catalyzes elongation of the main saturated fatty acid in plants, palmitoyl-ACP (C16:0). Elongation of palmitoyl-ACP to stearoyl-ACP requires β-ketoacyl ACP synthase II. Common plant unsaturated fatty acids are synthesized by desaturase. Desaturation of stearoyl-ACP by a soluble δ-9 desaturase form oleoyl-ACP (C18:1). Further desaturation takes place by action of membrane bound δ-12 desaturase to form linoleoyl-ACP (C18:2) and subsequently to α-linoleoyl-ACP by dδ-15 desaturase.

One way to modulate the levels of particular fatty acids that are produced is to alter the expression of genes involved in the biosynthesis of the fatty acids. Up-regulation or down-regulation of any of these genes would potentially alter the production of particular fatty acids. With respect to the present invention, one strategy of genetic manipulation is to increase the expression of a KAS II genetic sequence and potentially combine this with the use of antisense nucleotide sequences directed to a palmitoyl-ACP thioesterase encoding genetic sequence in order to reduce palmitic acid production and increase production of towards 18 carbon acyl chains. Manipulation of the stearoyl ACP desaturase gene may also be required to cope with the possible accumulation of stearic acid so that more oleic acid can be produced.

The availability of the nucleotide sequence of the present invention makes alterations to the expression of the KAS II genetic sequence possible. The nucleotide sequence set forth herein would facilitate the production of chimeric genetic constructs that can be inserted into vectors for the transformation of eukaryotic or prokaryotic cells or any multicellular structures generated from such cells. The genetic constructs may be used to increase the expression of KAS II in plants or other higher life forms such as plants and organisms: alternatively, constructs may be used to down-regulate or knock-out the KAS II gene in plant cells or other organisms.

"Chimeric genetic constructs" generally comprise, in addition, one or more regulatory regions such as inter alia promoters and 5' up-stream enhancer regions and 3' terminator sequences. These may be derived from any suitable heterologous genetic material, and are operably linked to the nucleic acid molecule of the present invention to generate the chimeric construct. By "operably linked" is meant that transcriptional and translational regulatory nucleic acids are positioned relative to a functional coding region in such a manner that the functional coding region is transcribed and optionally translated into a polypeptide. The term "functional" includes a nucleotide sequence which encodes a peptide, polypeptide or protein, or which exhibits some other function such as but not limited to binding to DNA or RNA. The transformed cell is thereby provided with a fully functional genetic unit which is capable of being integrated into the genome and which may be expressed by the transgenic cell. Alternatively, the introduced construct may exist extra-chromosomally. In the context of the present invention, "expressed" may refer to one or more or both of the transcription and translation of the introduced nucleotide sequence by the cell. The genetic construct may also be used to down-regulate a KAS II gene and/or other genes encoding enzymes or proteins involved in fatty acid biosynthesis.

Cells contemplated by the present invention which act as hosts to express a KAS II genetic sequence include plants, bacteria, fingi, yeasts, insects and other animal cells. In other words, any prokaryotic or eukaryotic cell is contemplated by the present invention.

Preferably, however, the cells are plant cells. Plants of the present invention include monocotyledonous and dicotyledonous plants, but are preferably monocotyledonous plants. Particularly preferred monocotyledonous plants are members of the Gramineae, Palmae, Juncaceae and Achenes families. More preferably, the plants are oil palm plants such as the species *E. guineensis* and *E. oleifera* including modified varieties or genetic variants thereof.

Bacteria of the present invention include Gram negative and Gram positive organisms, but preferably those bacteria suitable for the expression of heterologous proteins. Whilst the skilled artisan will be able to determine which bacteria are suitable for the expression of heterologous proteins, particularly preferred bacteria include *Escherichia coli, Bacillus subtilus* and *Streptomyces* spp. Within the *Streptomyces* genus, particularly suitable species are *Streptomyces lividans* and *Streptomyces coelicolor*. In a particularly preferred embodiment, the bacterial species is *E. coli*.

Fungi of the present invention include fungi suitable for the expression of heterologous proteins. Non-limiting examples of useful fungi are yeasts such as *Pichia pastoris, Saccharomyces cerevisiae* and *Saccharomyces pombe*.

Chimeric constructs further comprise 5' sequences, including a promoter sequence for driving the expression of the operably linked nucleic acid molecule. Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. A promoter is usually, but not necessarily, positioned upstream or 5' of a structural gene region, the expression of which it regulates. Furthermore, the regulatory elements comprising a promoter are usually positioned within 2 kb of the start site of transcription of the gene. In the construction of heterologous promoter/structural gene combinations, it is generally preferred to position the promoter at a distance from the gene transcription start site that is approximately the same as the distance between that promoter and the gene it controls in its natural setting. As is known in the art, however, some variation in this distance can be accommodated without loss of promoter function.

The promoter may regulate the expression of the structural gene component constitutively, or differentially with respect to the cell, tissue or organ in which expression occurs or, with respect to the developmental stage at which expression occurs, or in response to external stimuli such as physiological stresses, or pathogens, or metal ions, amongst others.

Preferably, the promoter is capable of regulating expression of a nucleic acid molecule in a prokaryotic cell or a eukaryotic cell, tissue or organ, at least during the period of time over which the target gene is expressed therein and more preferably also immediately preceding the commencement of detectable expression of the target gene in the cell, tissue or organ.

Plant-, bacterial- and fungal-operable promoters are particularly preferred for use in the construct of the present invention. Examples of preferred promoters include but are not limited to the bacteriophage T7 promoter, bacteriophage T3 promoter, SP6 promoter, lac operator-promoter, tac promoter, SV40 late promoter, SV40 early promoter, RSV-LTR promoter, CMV IE promoter, cauliflower mosaic virus (CaMV) 35S promoter, SCSV promoter, SCBV promoter and the like.

As mentioned above, the construct preferably contains additional regulatory elements for efficient transcription, for example, a 3' terminator sequence.

The term "terminator" refers to a DNA sequence at the end of a transcriptional unit, which signals termination of transcription. Terminators are 3' non-translated DNA sequences containing a polyadenylation signal, which facilitates the addition of polyadenylate sequences to the 3' end of a primary transcript. Terminators active in plants and/or bacteria and/or fungi are known and described in the literature. They may be isolated from bacteria, fungi, viruses, animals and/or plants or synthesized de novo. In the context of the present invention, the terminator may be any terminator sequence that is operable in the cells, tissues or organs in which it is intended to be used.

Examples of terminators particularly suitable for use in the various nucleotide sequences of the present invention include the SV40 polyadenylation signal, the HSV TK polyadenylation signal, the CYC1 terminator, ADH terminator, SPA terminator, nopaline synthase (NOS) gene terminator of *Agrobacterium tumefaciens*, the terminator of the CaMV 35S gene, the zein gene terminator from *Zea mays*, the Rubisco small subunit gene (SSU) gene terminator sequences, subclover stunt virus (SCSV) gene sequence terminators, any rho-independent *E. coli* terminator, or the lacZ α terminator, amongst others. Those skilled in the art will be aware of additional terminator sequences, which may be suitable for use in performing the invention. Such sequences may readily be used without any undue experimentation.

In an alternative embodiment, chimeric genetic constructs may comprise a nucleotide sequence defining a genomic region of the KAS II genetic sequence, beginning from either the "ATG" start codon or the putative transcription initiation site, and including the 3' termination sequence located following the "TAA" stop codon. Either way, chimeric genetic constructs so constituted may then be cloned into suitable vectors for the transformation of target organisms, in order to deliver the means for adding or subtracting a desirable trait or phenotype.

By "vector" is meant a nucleic acid molecule, preferably a polynucleotide sequence such as a DNA molecule derived, for example, from a plasmid, bacteriophage, transposon or virus, into which a genetic construct may be inserted or cloned. A vector preferably contains one or more unique restriction sites and may be capable of autonomous replication in a defined host cell, including a target cell or tissue or a progenitor cell or tissue thereof. The vector may contain any means for assuring self-replication. Alternatively, it may be integrable with the genome of the defined host such that the cloned sequence is reproducible. Accordingly, the vector may be an autonomously replicating vector (i.e. a vector that exists as an extra-chromosomal entity, the replication of which is independent of chromosomal replication; for example, a linear or closed circular plasmid), an extra-chromosomal element, a mini-chromosome or an artificial chromosome.

A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a second chimeric genetic construct, which comprises a selectable marker, such as an antibiotic resistance gene that can be used for selection of suitable transformants. Examples of such resistance genes are well known to those of skill in the art.

Once constructed, genetic constructs may be cloned into a suitable vector for delivery via any number of methods, into the target cell.

"Stringency" as used herein, refers to the temperature and ionic strength conditions, and presence or absence of certain organic solvents, during hybridization and washing procedures. The higher the stringency, the higher will be the degree of complementarity between immobilized target nucleotide sequences and the labeled probe polynucleotide sequences that remain hybridized to the target after washing.

"Stringency conditions" refers to temperature and ionic conditions under which only nucleotide sequences having a high frequency of complementary bases will hybridize. The stringency required is nucleotide sequence dependent and depends upon the various components present during hybridization and subsequent washes, and the time allowed for these processes. Generally, in order to maximize the hybridization rate, non-stringent hybridization conditions are selected: about 20-25° C. (e.g. 20, 21, 22, 23, 24 or 25° C.) lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5-15° C. (e.g. 5, 6, 7, 8, 9, 10, 11, 12, 13, 14 or 15° C.) lower than the $T_m$. In order to require at least about 70% nucleotide complementarity of hybridized sequences, moderately stringent washing conditions are selected to be about 15-30° C. (e.g. 15, 16, 17, 18, 19 or 20° C.) lower than the $T_m$. Highly permissive (low stringency) washing conditions may be as low as 50° C. below the $T_m$, allowing a high level of mismatching between hybridized sequences. Those skilled in the art will recognize that other physical and chemical parameters in the hybridization and wash stages can also be altered to affect the outcome of a detectable hybridization signal from a specific level of homology between target and probe sequences.

Reference herein to a low stringency includes and encompasses from at least about 0 to at least about 15% v/v formamide (e.g. 0, 1, 2, 3, 4, 5, 6, 7, 8, 9, 10, 11, 12, 13, 14 or 15% v/v) and from at least about 1 M to at least about 2 M salt for hybridization, and at least about 1 M to at least about 2 M salt for washing conditions. Generally, low stringency is at from about 25-30° C. to about 42° C. such as 25, 26, 27, 28, 29, 30, 31, 32, 33, 34, 35, 36, 37, 38, 39, 40, 41 or 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C)%. However, the $T_m$ of a duplex DNA decreases by 1° C. with every increase of 1% in the number of mismatch base pairs. Formamide is optional in these hybridization conditions. Accordingly, particularly preferred levels of stringency are defined as follows: low stringency is 6×SSC buffer, 0.1% w/v SDS at 25-42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

Terms such as "hybridization", "hybridizing" and the like are used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

The term "similarity" as used herein includes exact identity between compared sequences at the nucleotide or amino acid level. Where there is non-identity at the nucleotide level, "similarity" includes differences between sequences, which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window", to identify and compare local regions of sequence similarity. A "comparison window" refers to a conceptual segment of typically 12 contiguous residues that is compared to a reference sequence. The comparison window may comprise additions or deletions (that is, gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA), or by inspection and the best alignment (i.e. resulting in the highest percentage homology over the comparison window) generated by any of the various methods selected. Reference also may be made to the BLAST family of programs as for example disclosed by Altschul et al. (*Nucl. Acids Res.* 25:3389-3402, 1997). A detailed discussion of sequence analysis can be found in Unit 19.3 of Ausubel et al. ("Current Protocols in Molecular Biology" John Wiley & Sons Inc, 1994-1998, Chapter 15, 1998).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e.: the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

As indicated above, reference to at least about 70% identity (for nucleotide sequences) or 70% similarity (for amino acid sequences) includes amounts of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

A particularly preferred embodiment of the instant invention provides an isolated nucleic acid molecule comprising a sequence of nucleotides as set forth in SEQ ID NO: 1. Furthermore, although the present invention is particularly exemplified with respect to oil palm plants, this is done with the understanding that the instant invention extends to any monocotyledonous plant. Reference herein to a monocotyledonous plant includes any member of the Gramineae, Palmae, Juncaceae and Achenes plant families. Examples include cereals, grasses, maize, sugar cane, oats, wheat, barley as well as oil palm.

Accordingly, once a chimeric genetic construct has been cloned into a vector and transformed into target cell, the exogenously introduced KAS II coding sequence of the present invention may be expressed by the cell and translated into the encoded protein, in this case, the fatty acid biosynthetic enzyme, KAS II or a polynucleotide having KAS II activity. The action of the introduced protein may effect a desirable phenotype that would otherwise not be present. In this regard, particularly preferred phenotypes include an alteration of the total quantity, or relative amounts of fatty acids produced by the organism. In a particularly preferred embodiment the introduced KAS II gene is over-expressed by a plant, particularly an oil palm, wherein the over-expression of KAS II leads to an increase in the total amount of fatty acids, or an increase in the relative proportion C18 to C16 fatty acids, produced by said oil palm.

The present invention further provides a vector for use in generating transgenic plants exhibiting a modified phenotype wherein the cells of the transgenic plants produce a polypeptide having an amino acid sequence encoded by the nucleotide sequence as set forth in SEQ ID NO: 2 or SEQ ID NO: 1 or an amino acid sequence having at least 70% similarity to the amino acid sequence encoded by the nucleotide sequence as set forth in SEQ ID NO: 2 or SEQ ID NO: 1 after optimal alignment.

Means of introducing the vectors and chimeric genetic construct(s) of the present invention into a cell, cells or tissues (i.e. transfecting or transforming target cell, cells or tissues) are various and are well known to those skilled in the art. The technique used may vary depending on the known successful techniques for that particular organism. Possible techniques include but are not limited to, heat shock, transformation using $CaCl_2$ and variations thereof; direct DNA uptake into protoplasts; PEG-mediated uptake to protoplasts; electroporation; micro-injection of DNA; micro-particle bombardment of tissue explants or cells; vacuum-infiltration of tissue with nucleic acid, and T-DNA-mediated transfer from *Agrobacterium* to plant tissue.

By way of example, for micro-particle bombardment of cells, a micro-particle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). Examples of microparticles suitable for use in such systems include 0.1 to 10 μm and more particularly 10.5 to 5 μm tungsten or gold spheres. The DNA construct may be deposited on the micro-particle by any suitable technique, such as by precipitation.

Plant tissue capable of subsequent clonal propagation, whether by organogenesis or embryogenesis, may be transformed with a chimeric genetic construct of the present invention and a whole plant generated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g. apical meristem, axillary buds, and root meristem), and induced meristem tissue (e.g. cotyledon meristem and hypocotyl meristem).

The regenerated transformed plants may be propagated by a variety of means, such as by clonal propagation or classical breeding techniques. For example, a first generation (or T1) transformed plant may be selfed to give homozygous second generation (or T2) transformant, and the T2 plants further propagated through classical breeding techniques.

Transformed regenerated plantlets thereby generated may then exhibit a modified phenotype, by virtue of the effect of the exogenously introduced nucleotide sequence. For example, the introduction of a vector comprising a chimeric construct comprising a sequence encoding an enzyme having KAS II activity having an amino acid sequence encoded by the nucleotide sequence as set forth in SEQ ID NO: 2 or SEQ ID NO: 1.

Another aspect of the present invention provides an isolated polypeptide having KAS II activity or a biologically active fragment thereof, said polypeptide comprising an amino acid sequence encoded by the nucleotide sequence as set forth in SEQ ID NO: 2 or SEQ ID NO: 1 or an amino acid sequence having at least 70% similarity to the sequence encoded by the nucleotide sequence as set forth in SEQ ID NO: 2 or SEQ ID NO: 1 after optimal alignment.

It is to be understood that, as was the case for the isolated nucleic acid molecules set forth herein, the isolated polypeptide of the present invention also extends to encompass derivatives including, for example, fragments, variants, mutants and homologs of the said sequence. A "derivative" encompasses any single or multiple amino acid deletions, additions or substitutions as well as mutants, fragments, portions or parts of the polypeptide molecule. All such deletions, additions, substitutions, mutants, fragments, portions, or parts are encompassed by the term "derivative".

Accordingly, the nucleic acid molecule of the present invention may be used to introduce an ability for a plant cell to produce a KAS II enzyme, to down-regulate expression of a KAS II genetic sequence or the nucleic acid molecule may be used in a diagnostic manner. For example, the KAS II genetic sequence may be used to produce probes or primers to identify particular oil palm cultivars exhibiting high or altered KAS II activity and, hence, produce high quantities of valuable C18 fatty acids. It can also be used to monitor for somoclonal variants in propagating palm oil plants.

A further related aspect of the present invention contemplates the transformation of, in particular, monocotyledonous plant material such as that of *Elaeis* species, with other desirable chimeric genetic constructs in order to add to or subtract from the target plant material particular traits or phenotypes relating to fatty acid biosynthesis.

The present invention further contemplates promoter regions that may also include associated 5' regulatory regions, which provide a mechanism whereby the control of expression of an introduced nucleic acid molecule may be effected. It may be necessary and/or desirable to direct the expression of the exogenously introduced sequence to the appropriate tissue, for example, or to cause its expression in a developmentally regulated manner. Alternatively, constitutive expression may be desirable. The contemplated promoter region of the present invention is the natural promoter of the isolated nucleic acid molecule set forth in SEQ ID NO: 3 which in vivo is operably linked to the nucleic acid molecule.

Preferably, for expression in plants, the use of promoters capable of preferentially directing transcription and translation in other tissues to regulate the expression of a KAS II genetic sequence may be desired. For example, to target gene expression to the mesocarp, a nucleic acid sequence which regulates expression in the mesocarp of certain plants is needed. Alternatively, the gene to be targeted to a particular location is fused to a carrier protein.

Accordingly, in a related aspect, the present invention provides an isolated polynucleotide defining a 5' regulatory region and comprising a sequence of nucleotides as set forth in SEQ ID NO: 3, or a sequence having at least about 70% identity thereto after optimal alignment or a nucleotide sequence capable of hybridizing to SEQ ID NO: 3 or its complementary form under low stringency conditions.

Reference herein to the "5' regulatory region" includes, but is not limited to, the promoter, enhancer, 5' non-translated sequence, transcription initiation start site.

The polynucleotide promoter region of the present invention may be utilized, as described above, in the generation of a genetic construct, which comprises the polynucleotide promoter together with the nucleic acid molecule of the present invention and appropriate 3' sequences. The 3' sequences may be those also derived from the same isolated and cloned genetic sequences set forth herein or, alternatively, may be derived from other heterologous sequences. Furthermore, the polynucleotide promoter may be utilized in the generation of a chimeric genetic construct, which comprises the said promoter together with other heterologous nucleic acid sequences. Hence, the isolated polynucleotide promoter may be used to drive the expression of any genetic sequence capable to being used to provide and/or withdraw a particular phenotype to or from a target cell into which it is introduced.

Preferably, the target cell is derived from a plant from the Gramineae, Palmae, Juncaceae and Achenes families, more preferably from a plant of the family Palmae and even more preferably, a plant of the genus *Elaeis* and in particular *E. guineensis* and *E. oleifera*.

Therefore, the nucleic acid sequences disclosed herein may be applied to alter or modulate a particular trait/phenotype of a target cell or tissue in a plant, animal or cell and preferably a plant of the species *E. guineensis* or *E. oleifera*.

Nucleic acid sequences encoding KAS II biologically active in a host cell may be employed in nucleic acid constructs to change/modulate the amount of KAS II activity present in host cell, which includes prokaryotic or eukaryotic cells. KAS II may be used, alone or in combination with other enzymes, to catalyze the elongation condensation reactions of fatty acid synthesis depending upon the desired result. Preferably, the particular trait is the amount, and relative proportions of fatty acids found in the host cell or organism, or it may be one of any number of other traits. Function studies using the complete coding region of oil palm KAS II gene with *E. coli* demonstrate KAS II activity. This was confirmed by measuring the level of fatty acids produced by the cells from transformed and untransformed recombinant clones. In this analysis, the oil palm KAS II gene was cloned into expression vector and transformed into *E. coli* cells. Significant increases in C18:1 at the expense of C16:0 were detected in the *E. coli* cells that have been transformed with the oil palm KAS II gene. Protein or protein preparations displaying such activities, alone or in combination, may be used together with fatty acid synthesis substrates to drive synthase condensation reactions. The amino acid and nucleic acid sequences corresponding to the various preparations may be deduced and used to obtain other homologously related KAS II or other condensing enzymes.

Modulation may be effected, for example, by providing a genomic clone of the KAS II genetic sequence complete with its associated intron sequences, in either case driven by its own or a heterologous promoter region. Alternatively, modulation may be effected by providing a chimeric genetic construct comprising the polynucleotide promoter of the present invention driving another heterologous nucleic acid sequence. The terms "modulating" and "modulate" include up-regulating and down-regulating expression of the subject nucleic acid molecule or levels of the instant polypeptide.

Particularly desired phenotypes contemplated herein include, increased or decreased total fatty acid yield, and/or an increased proportion of stearic acids (C18:0) and subsequently oleic acids (C18:1).

Accordingly, another aspect of the present invention contemplates a method for generating a plant with a modified phenotype, said method comprising introducing into the genome of a plant cell or group of plant cells a genetic construct comprising a polynucleotide promoter region or functional equivalent thereof operably linked to a nucleotide sequence encoding a polypeptide having KAS II activity and having an amino acid sequence as set forth in SEQ ID NO: 2 or an amino acid sequence having at least 70% similarity to the sequence set forth in SEQ ID NO: 2 after optimal alignment.

In a related embodiment, the present invention contemplates a method for generating a plant with a modified phenotype, said method comprising introducing into the genome of a plant cell or group of plant cells a genetic construct comprising a polynucleotide sequence encoding a protein having KAS II activity, said polynucleotide sequence as set forth in SEQ ID NO: 1 or a polynucleotide sequence having 70% identity to SEQ ID NO: 1 after optimal alignment or a polynucleotide sequence capable of hybridizing to SEQ ID NO: 1 or its complementary form under low stringency conditions.

In a further preferred embodiment, the polynucleotide sequence encoding a KAS II polypeptide having an amino acid sequence encoded by the nucleotide sequence as set forth in SEQ ID NO: 2 or SEQ ID NO: 1 or an amino acid sequence having at least 70% similarity to the sequence encoded by the nucleotide sequence as set forth in SEQ ID NO: 2 or SEQ ID NO: 1 after optimal alignment is that set forth in SEQ ID NO: 1.

In an alternative preferred embodiment, the polynucleotide promoter region may be any other suitable promoter.

In yet another alternative embodiment, the modified trait or phenotype may be effected via modulation of the expression of an endogenous gene, using an introduced genetic construct comprising, for example, selected genomic intron and/or exon sequences. This aspect of the present invention is based on the proposal that intron and exon sequences are involved in genetic networking. The introns or exons may act as receiver sequences or signal sequences. In addition, the present invention extends to the use of genetic sequences to de-methylate nucleotide sequences or protect nucleotide sequences from methylation in order to prevent gene silencing. The present invention further contemplates RNAi or other post-transcriptional gene silencing techniques to silence a KAS II-encoding gene or an inhibitor of KAS II or a KAS II gene expression.

Yet another aspect of the present invention therefore contemplates an intron defined by an isolated genomic sequence comprising a sequence of nucleotides as set forth in SEQ ID NO: 5 or SEQ ID NO: 6 or a sequence having at least about 70% identity thereto or a sequence capable of hybridizing to SEQ ID NO: 5 or SEQ ID NO: 6 or complementary forms thereof under low stringency conditions.

The present invention extends to and encompasses bacterial cells, fungal cells, plant cells, plants and parts of plants, such as flowering and reproductive parts including seeds, transformed with one or more genetic constructs as set forth herein. In particular, the present invention provides genetically modified palm oil plants such as palm oil plants which produce modified amounts or ratios of fatty acids compared to non-genetically modified plants. This aspect of the present invention extends to parts of plants such as seeds, flowers, stems, leaves, embryos, roots, meristems and the like. Furthermore, the present invention extends to sees or embryos packaged for sale with instructions for use in generating genetically altered plants such as palm oil plants.

Preferably, the transformed plant or part of the plant is of the genus *Elaeis* and in particular *E. guineensis* and *E. oleifera*.

The present invention is further described by the following non-limiting Examples.

EXAMPLE 1

Reverse Transcriptase-Polymerase Chain Reaction (RT-PCR) to Amplify Partial Length KAS II (a) Methods One µg of total RNA from 17-week oil palm mesocarp was used to synthesize first strand cDNA from the polyA tail. A sense gene-specific primer (P1) designed based on the 5'-end of highly conserved region of rice KAS II gene (AU031953) (sequence: 5'-GCC ACA TCC TGA AGG TAG AG-3' [SEQ ID NO: 9]) was used to synthesize second strand cDNA in a linear amplification procedure. For this, 1.5 µl of 0.5 pmol primer P1 was used in total reaction volume of 25 µl containing 2.5 µl 10× ADVANTAGE (trademark) PCR Buffer (Clontech Laboratories, Inc.), 0.5 µl of 50× ADVANTAGE (trademark) Polymerase Mix and 0.5 µl of 10 mM each of dNTPs mix. The PCR mixture was heated at 95° C. for 3 min in PE GeneAmp Systems 9600 (Perkin Elmer). Thirty cycles of linear amplification were performed as follows: denaturation for 30 sec at 94° C., annealing for 90 sec at 55° C. and extension for 2 min at 68° C. Immediately following the linear amplification, PCR was performed using the KasP1 primer and anchored poly-dT primer with non-specific 5'-tail. For this, 22.5 µl reaction mixture containing 0.75 µl of 20 µM poly-dT primer, 2 µl of 5 mM dNTPs mix, 2.25 µl of 10× ADVANTAGE (trademark) PCR Buffer and 0.75 µl of 50× ADVANTAGE (trademark) Polymerase Mix was added to the linear amplification reactions. Two PCR cycles (94° C. for 30 sec, 40° C. for 2 min and 68° C. for 3 min) were performed to allow proper annealing of the poly-dT primer to the poly-A sequence. Subsequently, 1.5 µl of 10 pmol P1 primer in 2.5 µl was added to the PCR mix and cycling was immediately continued for 30 cycles at a higher annealing temperature using the linear amplification cycling conditions described above. One µl of this PCR product was used in a second PCR with identical conditions, but with an antisense gene-specific primer (P2) instead of the P1 primer. KasP2 primer is complementary to the 3' end of KAS II gene (sequence: 5' TGA GTT ATG CCC ACC GAA TC-3' [SEQ ID NO: 10]). PCR products from the second exponential amplification were electrophoresed on agarose gel to confirm production of amplicon. The band of interest was excised from the gel, eluted and cloned directly into PCR 2.1-TOPO (registered trademark) vector (Invitrogen, CA), and positive clones were analyzed by sequencing.

(b) Results

The first partial fragment of the oil palm KAS II gene was isolated by a three-step PCR procedure which included an asymmetric PCR with the P1 primer, and the two exponential amplification steps towards the polyA tail with the P1 primer and the P2 primer respectively, as described by van der Linden et al. 2002 (van der Linden, C. G., Vosman, B. and Smulders, M. J. M. Cloning and characterization of four apple MADS box genes isolated from vegetative tissue *J. Exp. Bot.* 2002 53: 1025-1036).

This resulted in a DNA fragment approximately 450 bp in size. Putative clones were sequenced. FIG. 1 shows the nucleotide sequence of the plasmid. The nucleotide and deduced amino acid sequence of the positive clone isolated was designated as KasEg7a. Nucleotide homology searches were carried out using BLASTx and BLASTn provided by the website of the National Center for Biotechnology Information (NCBI), a division of the National Library of Medicine (NLM) at the National Institutes of Health (NIH). Blast results were exclusively mRNA sequences for KAS II and KAS from various plants. The greatest similarity of 87% identity was with KAS II from *Hordeum vulgare* (Z34269.1). Thus, KasEg7a is believed to encode an oil palm KAS II.

EXAMPLE 2

Genome Walking to Obtain 5' End cDNA Sequence (a) Methods

A 1 kb partial clone of KAS II was obtained from an Expressed Sequence Tag (EST) library. An EST clone (EA1666C) was identified that exhibited 88% nucleotide sequence identity to the nucleotide sequence of KAS II. The 1.0 kb partial clone of KAS II was used to generate two antisense primers. First primer was a gene-specific primer GKAS1 (5' CAC CAG ATG GTG TTG AAG TTG CAT GAG C-3' [SEQ ID NO: 11] and secondly was a nested primer GKAS2 (5'-CCT GAT TCT GCT AGC GCC TTC TCA ATG C-3' [SEQ ID NO: 12]). These primers were used in 5' RACE reactions to amplify 5' sequence using the technique of genome walking based on the method recommended by the supplier (Clontech). For this, total DNA was isolated and purified from oil palm spear leaves using DNeasy Plant Mini Kit from Qiagen. Aliquots containing 2.5 µg DNA were digested with restriction enzymes DraI, EcoRV, PvuII and StuI that produce blunt ends and ligated to the GenomeWalker Adaptor creating the GenomeWalker libraries. Primary PCR was performed using 12 µl aliquots of each library with primer GKASI and primer AP1 provided with the Kit. The PCR product was diluted 50× and 1 µl was used in secondary PCR reaction using antisense nested gene-specific primer GKAS2 and primer AP2 from the Kit. PCR was carried out using Advantage Tth Polymerase Mix from Clontech and a Perkin-Elmer 9600 thermal cycler following the cycling conditions recommended in the GenomeWalker Kit. The secondary PCR product was analysed and purified from agarose gel using gel extraction kit from Qiagen and cloned into PCRII-TOPO vector (Invitrogen). The recombinant clone was sequenced using M 13 forward and reverse primers.

(b) Results

An approximately 630 bp PCR product was obtained in the primary PCR reaction using the DraI genome walker library and primer GKASI. The primary PCR product was used in a secondary PCR reaction using the nested primer GKAS2 and a product of approximately 610 bp was obtained. This was expected because the position of the primer GKAS2 is about 20 bp up-stream of GKAS1. The secondary PCR product was cloned. Plasmid preparation of the cloned product was produced and used for restriction analysis and sequencing. The nucleotide sequence of the cloned insert was compared with other KAS II gene sequences in GenBank using BLAST. The nucleotide sequence designated 4gkasII exhibited high sequence similarity with the corresponding region of the KAS II genes from other plants. Alignment analysis showed that this sequence overlaps with the 5' end of the 1.0 kb EST sequence (approximately 100 bp total homology). However, the genome walking procedure produced two intronic regions (non-coding), thus sequence analysis was difficult and this clone provided only about 100 bp of new sequence at the 5' end.

EXAMPLE 3

Rapid Amplification of cDNA Ends (RACE)

(a) Methods

Rapid Amplification of cDNA Ends (RACE) was carried out to obtain the 3' and 5' ends of the full-length KAS II. RACE-ready cDNA template was synthesized from 17 week oil palm mesocarp total RNA according to the method provided by the manufacturer (GeneRacer Kit, Invitrogen). To this, 1 µl of GeneRacer Oligo dT Primer provided with the kit was used in a 12 µl reaction mixture containing 10 µl of RNA and 1 µl of dNTPs Mix. The mixture was incubated at 65° C. for 5 min to remove any secondary structure followed by chilling on ice for 2 min. Subsequently, the following reagents were introduced into the reaction mixture: 4 µl of 5× First Strand buffer, 2 µl of 0.1 mM DTT, 1 µl of RNaseOUT (40 U/µl) and 1 µl of Superscript II RT (200 U/µl) in a total volume of 20 µl. The reaction was incubated at 42° C. for 50 min. The reaction was terminated by heating up the samples at 70° C. for 15 min followed by 2 min cooling on ice. Subsequently, 1 µl of RNaseH (2 U) was added to the mixture followed by incubation at 37° C. for 30 min.

The RACE-ready cDNA served as template in PCR to amplify either 3' or 5'cDNA ends of KAS II gene. 3' RACE approach was used to amplify 3' cDNA ends of KAS II gene and the transcription termination site. For this, PCR reaction was carried out using sense gene-specific primers that have been designed based on oil palm KAS II sequence (AF220453.1) (Table 4). The PCR reaction was prepared in total volume of 50 µl containing 1 µl of 10 µM of sense gene specific primer, 1 µl of cDNA template, 5 µl of 10× High Fidelity PCR buffer, 3 µl of 10 µM GeneRacer 3' primer provided with the kit, 1 µl of dNTP mix (10 mM each), 2 µl of 50 mM MgSO$_4$ and 0.5 µl of Platinum High Fidelity Taq DNA Polymerase (5 U/µl). PCR conditions were as follows: one cycle: 94° C. for 2 min, followed by five cycles; 94° C. for 30 sec and 72° C. for 1 min. Another five cycles of PCR were performed as follows; 94° C. for 30 sec and 70° C. for 1 min. Twenty PCR cycles were performed as follows; 94° C. for 30 sec, 65° C. for 30 sec and 72° C. for 1 min followed by one cycle of PCR at 72° C. for 10 min. One µl of the PCR product was used as template in secondary PCR reaction with identical conditions, but with nested GeneRacer 3' primer provided with the kit and a nested gene-specific primer instead of primer 2 (Table 4). The secondary PCR was carried out using the following PCR program; one cycle; 94° C. for 2 min followed by 25 cycles; 94° C. for 30 sec, 65° C. for 30 sec and 68° C. for 2 min and finally one cycle; 68° C. for 10 min. The PCR product was analyzed and purified from agarose gel using gel extraction kit (Nucleospin) and clones into PCR 2.1 TOPO (registered trademark) vector (Invitrogen).

For 5' RACE, PCR reactions with identical conditions as described for 3' RACE were carried out using an antisense gene-specific primer 1 (Table 5). Several antisense gene-specific primers were designed based on clone 4gkasII and the partial sequence of oil palm KAS II (AF220453). PCR products from the first and second amplification were electrophoresed on agarose gel to confirm production of amplicons. Bands of interest were cut out of the gel, eluted and cloned into PCR 2.1-TOPO (registered trademark) and the recombinant clones were analyzed by sequencing.

TABLE 4

Primer combinations of sense gene-specific primer 1 and nested gene-specific primer 2 used in 3' RACE experiments

| Gene-specific primer 1 | Nested gene-specific primer 2 |
|---|---|
| GKAS 20F (5'- CTC TCG CAG AGA AAT AGT GAT CCG ACT AAA GCG TCA CGG CCT-3' [SEQ ID NO:13]) | GKAS21F (5'- GGG CTG GCG TGC TTC TAC TGG AAG AAT TAG AGC ATG CT-3' [SEQ ID NO:14]) |

TABLE 5

Primer combinations of antisense gene-specific primer 1 and nested gene-specific primer 2 used in 5' RACE experiments.

| | 5' Gene-specific RACE primer 1 | Nested gene-specific primer 2 | Sequence origin for primer design |
|---|---|---|---|
| 1 | GKAS1 (Sequence: 5'-TGT GGC TCA GTC ATG TGG TAA GCA TCA CAT GTG AAG C-3' [SEQ ID NO:15]) | GKAS10 (Sequence: 5'-AGC ATG CTC TAA TTC TTC CAG TAG AAG GAG GCC AGC CC-3' [SEQ ID NO:16]) | Oil palm KAS II (AF220453.1) |
| 2 | GKAS11 (Sequence: 5'-GCC GTG ACG CTT TAG TCG GAT CAC TAT TTC TCT GCG AGA G-3' [SEQ ID NO:17] | GKAS12 (Sequence: 5'GCA GCA TCT GAT CCA CCA CAA AGC ATC ACA-3' [SEQ ID NO:18] | Oil palm KAS II (AF220453.1) |
| 3 | GKAS7 (Sequence: 5'-CAA CAT CCC AGG GGC GAG AAG CTT TCA CTG-3' [SEQ ID NO:19] | GKAS8 (Sequence: 5'-GTG AAA GTG CTC CGC ATG CCA CAA AAC C-3' [SEQ ID NO:20] | Clone 4gkasII |

(b) Results

Total RNA from 17 week oil palm mesocarp was used as template in 3' RACE reactions in order to obtain the 3' end sequence information of the KAS II gene and the stop codon. A gene-specific primer (GKAS20F [SEQ ID NO: 13]) was used in the primary PCR together with GeneRacer 3' primer. GKAS20F (SEQ ID NO: 13] was designed based on partial sequence of oil palm KAS II (AF220543.1). Since the product of the primary PCR was not specific, several bands were obtained. Therefore, 1 ml of the primary PCR product was used in a second round PCR reaction. In this reaction, a 38-mer nested gene-specific (GKAS21F [SEQ ID NO: 14]) and nested primer from the GeneRacer kit were used. This secondary PCR specifically amplified a 1.0 kb fragment. The band was purified from the agarose gel and cloned into PCR 2.1 TOPO (registered trademark) vector (Invitrogen). One of the recombinant clones designated KasU86m (SEQ ID NO: 5) was sequenced for both directions using M13 forward and reverse primers. The complete sequence of KasU86m (SEQ ID NO: 5) is given in FIG. 2. The sequence has significant homology with the partial KAS II gene from oil palm (AF220453.1) as well as other KAS II sequences. Open reading frame (ORF) analysis on the nucleotide sequence of KasU86m (SEQ ID NO: 5) indicated an ORF containing 159 amino acids. The 3' end of the cDNA has a stop codon and a further 300 bp of the 3' untranslated region (3' UTR).

In order to obtain the 5' end sequence of oil palm KAS II, 5' RACE was used. Several primers were designed based on the partial clone of KAS II (clone 4GKASII) and the partial length sequence of oil palm KAS II (AF220453.1) to maximize the number of putative KAS II sequences that may be amplified by these primers. Three independent 5'-RACE experiments were carried out using the combination of primers as shown in Table 5. Initial amplification using degenerate oligonucleotide primers generated a 700 bp amplicon. The product was cloned and sequenced on both strands using the M13 forward and reverse primers. Sequence analysis showed that the cDNA (designated KasU26RC) was incomplete. FIG. 3 shows the complete sequence of KasU26RC (SEQ ID NO: 6). Results showed 70 bp of the 3'-terminal region of KasU26RC overlaps with the 5'-terminal sequence of the genome walking product, clone 4GKASII. Within the overlapping region, the two sequences are 85% identical. Greater homology was observed between KasU26RC and KasU86m (SEQ ID NO: 5). The 3'-terminal region of KasU26RC (120 bp) overlaps with 100% identity to the 5'-terminal sequence of the KasU86m (SEQ ID NO: 5) indicating that the 3' and 5'amplified products were derived from the same gene (FIG. 4). Thus, the sequence obtained as included a further 5' extension of about 500 bp, to the cDNA sequence of KasU86m (SEQ ID NO: 5). The new sequence had an open reading frame of 318 amino acids.

Another 5'RACE reaction used primer GKAS10 (SEQ ID NO: 16) and GKA11 (SEQ ID NO: 17) produced ~900 bp insert. The product from the nested PCR reaction was cloned and sequenced. The sequence obtained showed further 5' extension to the original cDNA sequence of KasU26RC. However, alignment analysis with full-length KAS II genes from other plants suggests that the 5' end of the cDNA did not have a start codon. This clone, designated as 3GKAS11/12, contained a 937 bp insert. The third 5'RACE reaction was carried out using primer GKAS7 (SEQ ID NO: 19) and GKAS8 (SEQ ID NO: 20). The amplified product (~1.5 kb) was cloned and sequenced. This clone, designated KasU24 was completely sequenced on both strands using the M13 forward and reverse primers. Additional primers were designed based on the first sequencing data: primer GKAS13: 5'-GGG ATG GGT GTG GTG ACT CCA CTG GGC GTT GAT CCT GA-3' (SEQ ID NO: 21) and primer PU1: 5'-ATG GAC AAG TTT ATG CTT TAC TTA CTT-3' (SEQ ID NO: 22). FIG. 5 shows the complete sequence of KasU24 (SEQ ID NO: 8) obtained from the 5'RACE. The nucleotide sequences of KasU24 were compared with other KAS genes using BLAST. Alignment analysis showed that the nucleotide sequence of KasU24 overlaps (82% identical) with the 5' end of the KasU26RC sequence (approximately 485 bp). Therefore KasU24 provided the remaining 5' end sequence of KAS II. The sequence of clone KasU24 contains 400 bp of the 5'-UTR. The three clones were thus used to produce a final consensus sequence of the 5' end for the KAS II gene.

FIG. 6 shows a multiple sequence alignment for clones KasU86m, KasU26RC and KasU24 to produce the final consensus sequence of the full-length KAS II.

EXAMPLE 4

Direct Amplification of the Full Length KASII cDNA (a) Methods

The entire open reading and some of the untranslated regions at each end were amplified using primers designed using the consensus sequence. Two sense primers (GKAS27 and GKAS28 [SEQ ID NO: 23 and SEQ ID NO: 24, respectively) were designed that bound up-stream of the start codon while the antisense primers (GKAS29 and GKAS30 [SEQ ID NO: 25 and SEQ ID NO: 26, respectively) were located down-stream of the stop codon (Table 6). Preparation of cDNA and PCR amplification were carried out using SMART RACE cDNA Amplification kit and Expand High Fidelity PCR system (Roche). cDNA used was derived from RNA isolated from 17-week mesocarp tissue. PCR parameters were optimized with all combinations of sense and antisense primers. A specific product of the expected size was obtained using two primer combinations, namely GKAS27/GKAS29 (SEQ ID NO: 23/SEQ ID NO: 25) and GKAS27/GKAS30 (SEQ ID NO: 23/SEQ ID NO: 26), which gave products of 2.1 kb and 2.0 kb, respectively. The amplification was carried out using 35 cycles of 30 sec at 94° C., 30 sec at 58° C. and 2 min 30 sec at 72° C. Fragments were purified and subsequently cloned into PCRII-TOPO vector (Invitrogen) for sequence analysis.

TABLE 6

Sequence of primers used in end to end PCR to amplify the full-length KAS II gene

| Primer | Sequence | |
|---|---|---|
| GKAS27 | 5'-ATGCTTTTGTAGGCCCATAGCTGAT GC-3' | [SEQ ID NO:23] |
| GKAS28 | 5'-TTCCATATGATCAAGATGTTGGTGC C-3' | [SEQ ID NO:24] |
| GKAS29 | 5'-TGAGATCGATGCCATCTCTCATTCC CTTCGTC-3' | [SEQ ID NO:25] |
| GKAS30 | 5'-TCTTGGCCTCTTCTCCTCTCTCAAC TTC-3' | [SEQ ID NO:26] |

(b) Results

DNA sequence analysis of the 10 putative colonies indicated that positive clones having total homology to the consensus sequence of oil palm KAS II were recovered. DNA and translated amino acid sequences of one positive clone designated KasEg2C, are presented in FIG. 7. The nucleotide sequence of clone KasEg2c was compared with the sequences of other KAS II genes in the GenBank database using the BLASTN search. Homology ranged from 96-97% identity to corresponding regions of partial length KAS II sequences from *E. oleifera* (AY089977.1) and *E. guineensis* (AF220453.1), to 80-84% identity with other KAS II sequences from various organisms as the top 50 best matches. The greatest similarity over the full-length gene of oil palm KAS II of 84% identity, was with sequence from castor bean chloroplast synthase (L13241.1). FIG. 8 shows alignment analysis between the nucleotide sequences of KasEg2C and other KAS II sequences from the GenBank database.

The transit peptide cleavage site of the KAS II gene is not known. In order to identify a putative or possible start site for the gene, the oil palm KAS II sequence was compared with other KAS II genes. Multiple sequence analysis suggests that region of MAGAAV is the start site for the coding region and thus, the final sequence contains a 1610 bp open reading frame coding for 536 amino acids with predicted molecular weight ~55 kDa.

EXAMPLE 5

Northern Blotting (a) Methods

Northern blot analysis was carried out using 5 μg of messenger RNA per lane. mRNA was extracted from 8-, 12-, 15-, 17- and 20-week after anthesis oil palm mesocarp, germinated seedlings, spear leaf, root and flower tissues, and also 10-, 11-, 12-, 15- and 17-week after anthesis oil palm kernel. mRNAs were denatured in 18 μl of solution containing 78% v/v deionized formamide, 16% v/v deionized glyoxal, and 10 mM $NaH_2PO_4/Na_2HPO_4$ (pH 7.0) by heating for 15 min at 55° C. followed by immediate cooling. Denatured mRNA was separated on 1.2% w/v agarose gel (3 hours) using 40 mM Tris-acetate (pH 7.0) as the electrophoresis buffer. The lane containing RNA Millenium markers (Ambion) was excised from the gel and stained with ethidium bromide and the markers were visualized by UV transillumination. Transfer to a nylon membrane (Hybond-N Amersham) was carried out using a VacuGene XL vacuum blotter (Amersham Pharmacia Biotech) (60 cm $H_2O$, 4 hours) in 20×SSC (1×SSC is 0.15 M NaCl, 15 mM trisodium citrate $2H_2O$, pH 7.0). The membrane was rinsed in 2×SSPE (1×SSPE is 0.18 M NaCl, 10 mM $NaH_2PO_4$, pH 7.5, 1 mM EDTA) before continuing with prehybridization. The cDNA insert from a KAS II clone was purified and subsequently labeled with $[\alpha\text{-}^{32}P]dCTP$ (Amersham Pharmacia Biotech) using Megaprime DNA Labelling system (Amersham Pharmacia Biotech) according to the method of the supplier. The unincorporated $[\alpha\text{-}^{32}P]$ dCTP was removed from the probe by gel filtration using a Chromaspin TE-10 column (Clontech). Prehybridization of the membrane was performed at 65° C. for 2 hours in 5×SSPE, 5× Denhardt's (1× Denhardt's solution in 0.02% v/v Ficoll 400, bovine serum albumin and polyvinylpyrrolidone), 0.5% w/v SDS and 100 μg/ml denatured herring sperm DNA. This is followed by hybridization of the membranes with $1\times10^6\text{-}5\times10^6$ cpm/ml radiolabeled probe overnight at 65° C. The membranes were then washed once in 2×SSC, 0.1% w/v SDS at 37° C. for 15 min and twice in 0.1×SSC, 0.5% w/v SDS at 65° C. for 45 min prior to autoradiography. The membranes were subsequently exposed to Hyperfilm MP X-ray films (Amersham Pharmacia Biotech) at –80° C. overnight or for 48 hours in a cassette with an intensifying screen, depending on the desired intensity and level of background.

(b) Results

Northern blot analysis was carried out using the 2.0 kb oil palm KAS II as the probe. The clone (KasEg2c) contains the 3'- and 5'-UTR as well as the full coding region of the gene. Poly $(A)^+$ RNA used were from different stages of development of mesocarp ranging from very young at 8 weeks of age followed by mid stage of 12, 15 weeks of age and mature stage at 17 and 20 weeks of age where active oil accumulation is occurring. Poly $(A)^+$ RNA from five stages of kernel development, i.e. 10, 11, 12, 15 and 17-week kernel were also included. At 12 weeks of age, active oil synthesis has started in the kernel. Poly $(A)^+$ RNA from the flower as well as vegetative tissues including young leaves, germinated seedlings and roots were also used. It was observed that the probe hybridized to an approximately 2.0 kb transcript in all tissues (FIG. 9). The highest level of KAS II expression was observed in the 20-week mesocarp, 12 week kernel and germinated seedlings. KAS II plays a role in the synthesis of C18:0 saturated fatty acid which undergo further unsaturation reactions to C18:1, C8:2 and C18:3. These fatty acids are required as components of plant membranes, and may explain the expression of KAS II in germinated seedlings. The level of gene expression was also detected in the flower but very negligible in roots and young leaves. Expression of KAS II in the mesocarp was low in younger tissues (8 and 12-week) and higher at the 17 and 20-week stage, which correlates well with the period of oil synthesis in this tissue.

EXAMPLE 6

Expression of Oil Palm KASII in *E. coli*

(a) Methods

TOPO vector containing full length KASII and expression vector pET-29 (Novagen) were digested with EcoRI (Fermentas, USA). The digested pET-29 was dephosphorylated with 1 U shrimp alkaline phosphatase (Promega, USA).

100 μg of EcoR1 digested DNA was dephosphorylated with 1 U of alkaline phosphatase. The dephosphorylation cocktail consisted of 2 µl digested DNA (200 µg total), 1 µl 10×SAP buffer, 5 µl water and 2 µl SAP (1 U/µl). This was incubated at 37° C. followed by 65° C. for 15 minutes each. The excess alkaline phosphatase was eliminated using the Qiaquick PCR purification kit (Qiagen, Germany). Linearized pET vector and KasEg2c were ligated with T4 DNA ligase according to the manufacturer's directions (Fermentas, USA). The ligation was then incubated overnight at 16° C. followed by inactivation at 65° C. for 10 minutes.

Competent *E. coli* BL21(DE3)pLysS was used as a recipient for the construct. One microliter of ligation mixture was added to the cells and the mixture was swirled gently to mix. The cells were incubated for 5 minutes on ice, followed by heat shock for 30 seconds at 42° C. Eighty microliters of SOC media was added to the cells followed by further incubation for 30 minutes at 37° C. with shaking. The cells were evenly spread onto LB media supplemented with kanamycin (30 µg/ml) and chloramphenicol (34 µg/ml) and incubated overnight at 37° C. Putative transformants were passaged onto the same selective medium. Screening for positive transformants was carried out by PCR using the gene-specific primers, GKAS27 (SEQ ID NO: 23) and GKAS30 (SEQ ID NO: 26). Positive transformants were identified by the production of a 2.0 kb PCR product.

Transformants confirmed by PCR were induced with IPTG. For this, a single colony was grown in 5 ml LB with appropriate antibiotics (kanamycin [30 µg/ml] and chloramphenicol [34 µg/ml]) overnight at 37° C. with shaking at 200 rpm. The next day, 1 ml culture was transferred into 49 ml of new LB containing antibiotics and incubated until the $OD_{600}$ was 0.4 to 0.6 (mid log phase, approximately 6 hour). Half of the culture was saved to serve as a control before IPTG induction. IPTG (1 mM final concentration) were added to the rest of the culture and incubation continued overnight. Cells were harvested by centrifugation at 4000 rpm for 15 minutes at 4° C. The pellet was then re-suspended in 0.25 volume with 20 mM Tris-HCl pH 8.0 and stored in −20° C. for SDS-PAGE analysis.

(b) SDS-PAGE Gel Analysis

Gel electrophoresis was performed using a Biorad protein Iixi dual slab cell system. Discontinuous gel at a 12% w/v acrylamide concentration, comprising a resolving gel and a stacking gel were cast as follows.

The separating gel was prepared by combining distilled water (25.125 ml), 1.5 M Tris-HCl pH 8.8 (18.75 ml), acrylamide/Bis (30% v/v stock—29.2 g acrylamide/100 ml, 2.4 g N'N'-bis-methylene-acrylamide/100 ml) (30 ml) 10% w/v SDS (0.75 ml), 10% w/v ammonium persulfate (APS) (0.375 ml) and TEMED (0.0375 ml) and the solution was swirled gently to mix. This made 75 ml of the gel solution which was enough for two gels.

The gel solution was pipetted between the glass plates, which had been previously cleaned with ethanol. The gel solution was covered with a layer of distilled water to give a straight edge on setting and left for 1.5 hour to polymerize. Water was removed from the gel surface and the gel surface was dried with filter paper.

The stacking gel solution, consisting of distilled water (6.71 ml), 0.5 M Tris-HCl pH 6.8 (2.75 ml), 10% w/v SDS (0.11 ml), acrylamide/Bis (30% stock) (1.43 ml), 10% APS (0.055 ml) and TEMED (0.011 ml) was pipetted on top of the separating gel. The comb was inserted and the stacking gel was left to set for a further 1.5 hour.

Protein samples were incubated with 0.06 M Tris-HCl (pH 6.8) buffer containing 20% v/v glycerol, 5% v/v 2-β-mercaptoethanol, 2% w/v SDS and 0.0025% w/v) bromophenol blue.

The samples were heated at 90° C. for 5 minutes prior to loading. SDS-PAGE low range molecular-weight standards (Bio-Rad) were used.

The running buffer was made from a pre-prepared 10 times strength stock which contained Tris-HCl pH 8.3 (30.3 g/L), glycine (144 g/L) and SDS (10 g/L) and was stored at 4° C. and diluted with distilled water before use. The gel was run for approximately 18 hours at 30V (constant voltage setting) or until the dye of the sample buffer had reached the bottom seal, approximately 5 mm above the bottom of the glass plates.

Gels were removed from the gel apparatus and rinsed with distilled water before immersion in 0.2% w/v Coomassie brilliant blue in 40% v/v methanol, 10% v/v acetic acid and 50% v/v distilled water for 1 hour. Protein bands were visualized after destaining with 40% v/v methanol, 10% v/v acetic acid in distilled water.

(c) Fatty Acid Analysis

Analysis of *E. coli* cells containing the KAS II construct and control cells lacking this construct was conducted to determine their fatty acid composition. Lipids were extracted from pelleted *E. coli* cells and the fatty acids were analysed by methanalysis and gas-liquid chromatography essentially as described by Browse et al. 1986 (Browse, J., McCourt, P. J. and Somerville, C. R. Fatty acid composition of leaf lipids determined after combined digestion and fatty acid methyl ester formation from fresh tissue. *Anal Biochem* 152: 141-145). Fatty acid composition of leaf lipids determined after combined digestion and fatty acid methyl ester formation from fresh tissue. Results are presented in Table 7.

TABLE 7

Analysis of fatty acids in sense-KAS II transformed *E. coli*

| Fatty Acid | | % Fatty Acid Composition | |
|---|---|---|---|
| | | Control (n = 2) | Sense KAS II (n = 5) |
| C14.0 | Myristic | 7.0 | 12.5 ± 1.0 |
| C16.0 | Palmitic | 58.2 | 26.2 ± 1.9 |
| C18.0 | Stearic | 11.2 | 6.7 ± 3.0 |
| C18.1 | Oleic | 18.6 | 47.5 ± 5.2 |
| C18.2 | Linoleic | 4.8 | 6.1 ± 0.7 |

These results demonstrate that the percentage of C18 fatty acids in *E. coli* increases upon expression of the oil palm KAS II protein in *E. coli*. Biochemical studies had confirmed that KAS II is an important regulatory enzyme that is responsible for palmitic acid accumulation in the oil palm mesocarp (Umi Salamah Ramli and Sambanthamurthi, R. (1996) β-Ketoacyl ACP synthase II in the oil palm (*Elaeis guineensis* Jacq.) mesocarp. In Physiology, Biochemistry and Molecular Biology of Plant Lipids (Williams, J. P., Khan, U. M. and Lem, N. W. eds) pp. 69-71, Kluwer Academic Publ., Toronto). Increasing the activity of this enzyme will decrease the palmitic acid (C16:0) and increase oleic acid (C18:1) content of palm oil. Thus, the expression studies with *E. coli* have demonstrated proof of the principle.

EXAMPLE 7

Expression of Oil Palm KASII in *Arabidopsis thaliana*

(a) Methods pCB302-1 vector (~6.8 kb), which includes the CaMV 35S promoter, was digested with EcoRI. The full length KASII gene (~2.0 kb), derived from KasEg2C was digested with EcoRI and purified using Qiaquick gel extraction method. Cloning of the full length KAS II gene (~2.0 kb) into pCB302-1 was carried out by sticky end ligation into the EcoRI restriction site. The vector (pCB302-1) and insert (KAS II gene) were ligated using a 1:3 vector to insert end ratio. Transformation of *E. coli* DH5α competent cells was carried out using heat shock method (Hanahan, D. 1983. Studies on transformation of *E. coli* with plasmids. *J. Mol. Biol.* 166: 557-580).

Fifty mg/L kanamycin was used as a selection agent. Putative transformants were inoculated into 10 ml Luria Broth supplemented with 50 mg/L kanamycin. After incubation, plasmids were isolated from the putative transformants using alkaline lysis.

Figure 10A:
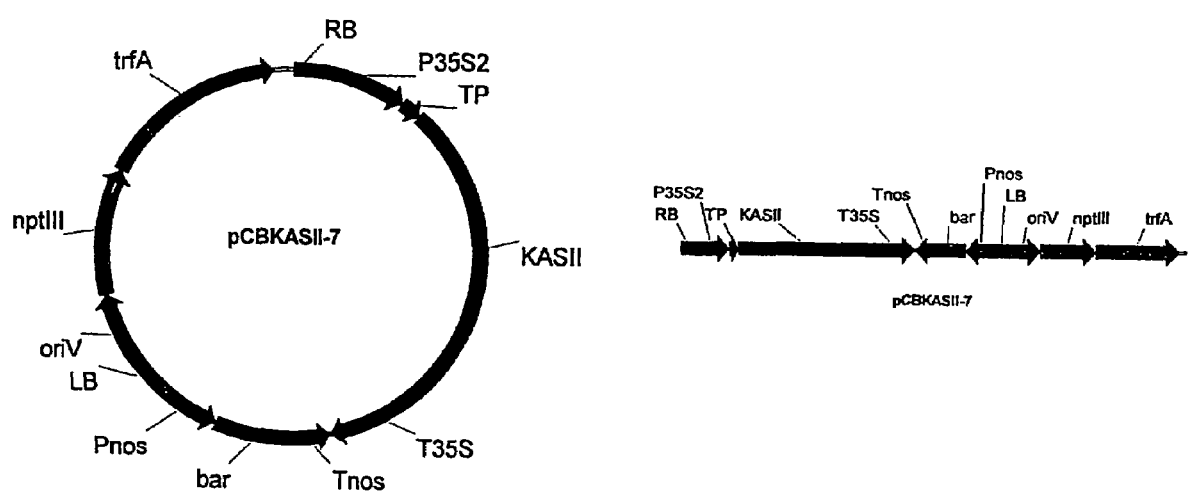
FIG. 10A is a schematic diagram of plasmid pCBKASII-7. The arrow indicates the orientation of each DNA fragments assembled. RB, right border of T-DNA; P35S2, 35S promoter with double enhancers; TP, plastid targeting sequence of Rubisco small subunit; KAS II, sense KASII gene; T35S, terminator of cauliflower mosaic virus; Tnos, terminator of nos (nopaline synthase) gene; bar, gene for phosphinothricin acetyltransferase; Pnos, promoter of nos (nopaline synthase) gene; LB, left border of T-DNA; oriV, part of RK2 origin of replication (from pBIN19); nptIII, gene for neomycin phosphotransferase for kanamycin resistance (from pBIN19); trfA, part of RK2 origin of replication.
Figure 10B:
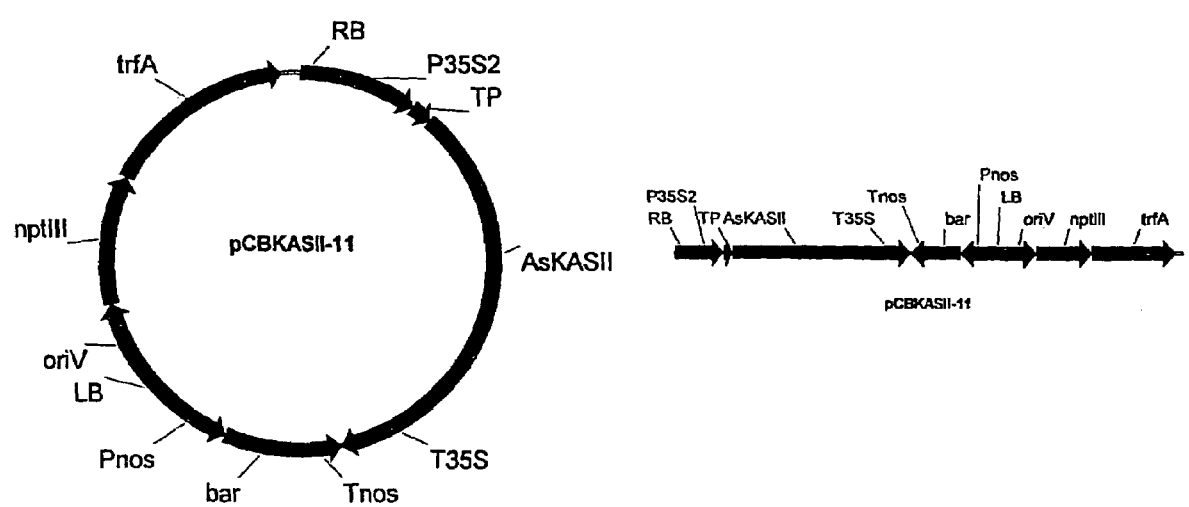
FIG. 10B is a representation showing plasmid pCBKASII-11. The arrow indicates the orientation of each DNA fragments assembled. RB, right border of T-DNA; P35S2, 35S promoter with double enhancers; TP, plastid targeting sequence of Rubisco small subunit; AsKAS II, antisense KAS II gene; T35S, terminator of cauliflower mosaic virus; Tnos, terminator of nos (nopaline synthase) gene; bar, gene for phosphinothricin acetyltransferase; Pnos, promoter of nos (nopaline synthase) gene; LB, left border of T-DNA; oriV, part of RK2 origin of replication (from pBIN19); nptIII, gene for neomycin phosphotransferase for kanamycin resistance (from pBIN19); trfA, part of RK2 origin of replication.

The positive clones were selected by re-digestion of the plasmid with EcoRI. The orientation of the insert was confirmed by digestion with BamHI to yield approximately 0.3 kb and 8.8 kb fragments for sense orientation, and approximately 1.2 kb and 7.9 kb fragments for antisense orientation. Two final plasmids were designed, pCBKASII-7 (sense KAS II; FIG. 10A) and pCBKASII-11 (antisense KAS II; FIG. 10B) as:

(i) pCBKASII-7
[Right border-(P35S-TP-sense KAS II-T35S>)-(<-Tnos-bar-Pnos)-Left border]

(ii) pCBKASII-11
[Right border-(P35S-TP-antisenseKAS II-T35S>)-(<-Tnos-bar-Pnos) Left border]

(b) *Agrobacterium tumefaciens* Transformation

*Agrobacterium tumefaciens* strain LBA4404 was transformed with either plasmid pCBKASII-7, a binary vector carrying oil palm sense KAS II and bar genes driven by CaMV 35S promoters, or pCBKASII-11 a binary vector carrying oil palm antisense KAS II and bar genes driven by CaMV 35S promoters, via electroporation using the Bio-Rad GENE PULSER. *A. tumefaciens* was grown overnight at 27° C. in of 2×YT medium (1% w/v NaCl, 1% w/v tryptone and 0.5% v/v yeast extract, pH 7). Two 1.5 ml aliquots of bacteria were centrifuged. The bacterial pellets were then resuspended in 0.5 ml ice-cold 10% v/v glycerol and re-centrifuged. The pellets were again resuspended in 20 µl of 10% v/v glycerol and contents of both tubes were combined. One µl of each plasmid was added into 2×40 µl aliquots of *Agrobacterium* and left on ice for 2 min. The mixture was pulsed in an ice-cold 0.2 cm Bio-Rad cuvette. The GENE PULSER was set at 25 µF capacitance, 2.5 KV charge and the pulse controller to 400 Ω resistance. Immediately after the pulse, 1 ml of SOC broth was added into each tube. The mixture was incubated at 27° C. for 4-6 hours before plating on 2×YT agar containing 10 µg/ml chloramphenicol and 50 µg/ml [2×YT (10C50K)]. Plates were incubated overnight and ten resistant colonies were selected randomly and inoculated into 10 ml 2×YT medium containing the above antibiotics. The transformed cells were confirmed after isolation and digestion of the plasmids.

(c) Small Scale Plasmid Isolation

Ten microliters of overnight culture was inoculated into 10 ml of 2×YT (10C50K) medium. The overnight culture was transferred to microfuge tubes and bacteria were pelleted by centrifugation at 4,000 rpm, 5 min and 4° C. Plasmid isolation was carried out using alkaline lysis. The bacterial pellet was resuspended in 200 µl of ice cold solution I (25 mM Tris-HCl, 10 mM $Na_2$-EDTA, 50 mM glucose pH 8.0 {5 mg/ml lysozyme}) and the mixture was kept at room temperature for 5 min. 300 µl of solution II (0.2M NaOH, 1% w/v SDS) was added, mixed by gentle inverting and incubated on ice for 5 min. 250 µl of solution III (5M KAc) was added, mixed vigorously and incubated on ice for 5 min. The lysate was centrifuged (15,000 rpm, 15 min and 4° C.) and the supernatant transferred to a new microfuge tube. 600 µl of phenol:chlorofom (1:1) was added to each tube, mixed for 2 minutes and centrifuged (15,000 rpm, 5 min and 4° C.). The aqueous phase was then transferred to 600 µl of chloroform, mixed for 2 min and centrifuged (15,000 rpm, 5 min and 4° C.). The aqueous phase was transferred to a new tube, one volume of isopropanol and 100 µl of 10M $NH_4Ac$ were added, mixed gently and incubated at room temperature for 15 min. Nucleic acids were collected by centrifugation (15,000 rpm, 15 min and room temperature), rinsed with 70% v/v ethanol and dried at room temperature for 30 min. The final pellet was resuspended in 100 µl of TE buffer (10 mM Tris, Im M EDTA, pH 8.0), gently mixed, treated with RNase (75 µl {5 mg/ml}, 15 min and 37° C.).

(d) *Arabidopsis thaliana* Plant Growth Before Infiltration

*Arabidopsis* seeds (ecotypes: Columbia, Landsberg ecrecta and a KAS II mutant) were harvested on wet compost in plastic pots. The pots were place at 4° C. for stratification. The pots were later placed in Conviron growth chamber (Model TC30) with a 16 hour day photoperiod, 20 to 25° C. with additional artificial light (105:E/m 2/s) and subirrigation with a layer of tap water under the pots. The optimal stage for floral-dipping is when the plants have formed the first siliques and the secondary floral stems are appearing.

(e) *Arabidopsis thaliana* Floral-dip Transformation with *Agrobacterium tumefaciens* LBA4404

*Agrobacterium tumefaciens* strains LBA4404 carrying the binary plasmid pCBKASII-7 or pCBKASII-11 were used in all experiments for which data are shown. Unless noted, bacteria were grown to stationary phase in liquid culture at 25-28° C., 250-280 rpm in sterilized 2×YT (10C50K) medium. Cells were harvested by centrifugation (5 500×g) for 20 min at room temperature and then resuspended in floral-dip medium to a final $OD_{500}$ of approximately 0.80 prior to use. The floral dip inoculation medium contained 5.0% w/v sucrose and 0.05% w/v Sliwet L-77. The inoculum was added to a beaker, plants were inverted into this suspension such that all aboveground tissues were submerged, and plants were then removed after 3-5 sec of gentle agitation. Dipped plants were removed from the beaker, placed in a plastic tray and covered with a tall clear-plastic dome to maintain humidity. Plants were left in a low light or dark location overnight and returned to the growth chamber the next day. Domes were removed approximately 12-24 h after treatment, plants were grown for a further 3-5 weeks until siliques were brown and dry. Seeds were harvested by gentle pulling of grouped inflorescences through fingers over a piece of clean paper and stored in a microcentrifuge tube prior to screening.

(f) Screening of Transformants

Seeds were harvested on wet compost in plastic pots. The compost was wetted with water containing Basta (Final 10 ppm). The selection with herbicide is more efficient (to avoid escaped plants) as compared to antibiotics. The pots were place at 4° C. for stratification. The pots were later placed in Conviron growth chamber (Model TC30) with a 16 hour day photoperiod, 20 to 25° C. with additional artificial light (105: E/m 2/s) and subirrigation with a layer of tap water containing Basta. Once the plants produced normal green cotyledons and two true leaves, they were sprayed with Basta solution (Final 50 ppm). The plants were sprayed again with the same Basta solution after two weeks. The resistant plantlets were transferred into individual pots when they are sufficiently developed (4-5 leaf-stage) to prevent cross-pollination and/or seed contamination. The surviving plants were grown until the siliques were brown and dry. T2 Seeds were harvested by gentle pulling of grouped inflorescences through fingers over a piece of clean paper and stored in a microcentrifuge tube.

Gas Chromatography Analysis

Samples (calli, embryogenic calli, polyembryogenic calli or seeds) were extracted and subjected to Gas Chromatography to determine fatty acid composition. Methylation methods for Fatty Acid Methyl Esters (F.A.M.E) was done. The detection of every compound was done based on the retention time that was referred to F. A. M. E. RM-6 Standards (C14:0, C16:0, C16:1, C18:0, C18:1, C18:2 and C18:3) [Supelco].

Sample Preparation Procedure 2 gram of sample (callus, embryogenic callus, polyembryogenic callus or seeds) was added and vortexed with 2 ml toluene and 2 ml 2.5% acidic methanol. Condenser was attached and placed in heating block, and then sample was refluxed at 85° C. for 2 hours. After 2 hours, sample was transferred into new vial and 3 ml hexane and 5 ml 5% NaCl was added. Sample was mixed and centrifuged for 5 minutes at 2500 rpm. Upper layer was transferred into new vial and then sample was added with 2 ml hexane and 10 ml 2% $KHCO_3$. Sample was mixed and centrifuged again for 2 minutes at 2500 rpm. Upper layer was transferred into new vial and the hexane were evaporated in vacuum or under a nitrogen blanket. Sample was diluted 1:5 v/v in hexane before injection into GC.

Instrumentation.

GC/FID analysis were performed on Agilent GC6890N (Agilent, USA) that equipped with splitless injector at 250° C. Around 1 µl of the solution of FAMEs 1:5 v/v in hexane was applied into GC. Agilent autosampler, AOL series (Agilent 7683 Series) and FID at 300° C. were used ($H_2$ flow 40 ml $min^{-1}$, air flow 350 ml $min^{-1}$ and makeup He 45 ml $min^{-1}$). Data acquisition was performed by MSD and MSD Data Analysis software (Agilent, USA). A columns, DB-23 (J & W P/N:123-2332) (0.25 mm×30 m×0.20 µm film) was used for the analysis. The temperature program was as follows: 50° C. initial temperature for 2 minutes, ramp 1: 50° C.-180° C. at 10° C./min, ramp 2: 180° C. for 5 min, while final temperature 180° C.-240° C. at 5° C./min. (total runtime 37 min). Helium was used as a carrier gas (1 ml $min^{-1}$). The FAC was calculated as normalized percentages from the peak areas.

EXAMPLE 8

Antisense KAS II Expression in *A. thaliana*

The methods described in Example 7 for transformation and analysis of fatty acids were used in this experiment.

The antisense KAS II construct, pCBKASII-11, was transformed into *Arabidopsis thaliana* and fatty acid analysis of the transformed and control seeds was performed using Gas Chromatography (GC). Results of the analysis are presented in Table 8.

TABLE 8

Analysis of fatty acids in antisense-KAS II transformed *A. thaliana*

| | | % Fatty Acid Composition | |
| --- | --- | --- | --- |
| Fatty Acid | | Control (n = 7) | Antisense KAS II (n = 7) |
| C14:0 | Myristic | 4.8 ± 1.8 | 1.0 ± 0.3 |
| C16:0 | Palmitic | 37.8 ± 8.6 | 66.3 ± 7.1 |
| C16:1 | Palmitoleic | 4.6 ± 1.1 | 1.6 ± 0.6 |
| C18:0 | Stearic | 21.2 ± 5.0 | 8.6 ± 1.8 |

TABLE 8-continued

Analysis of fatty acids in antisense-KAS II transformed *A. thaliana*

| | | % Fatty Acid Composition | |
| --- | --- | --- | --- |
| Fatty Acid | | Control (n = 7) | Antisense KAS II (n = 7) |
| C18:1 | Oleic | 21.9 ± 5.0 | 21.6 ± 7.0 |
| C18:2 | Linoleic | 4.0 ± 0.6 | 0.3 ± 0.3 |
| C18:3 | Linolenic | 5.7 ± 0.4 | 0.5 ± 0.1 |

EXAMPLE 9

Transgenic Expression of KASII in Plants

Higher plants synthesize fatty acids via a common pathway. In developing seeds, de novo production of fatty acids takes place in the proplastids. These fatty acids are attached to triacylglycerides and stored as a source of energy for further germination. The first step is the formation of acetyl-ACP from acetyl-CoA and ACP catalyzed by the enzyme, acetyl-CoA:ACP transacylase. Elongation of acetyl-ACP to 16- and 18-carbon fatty acids involves a series of four reactions; condensation with a two-carbon unit from malonyl-ACP to form a β-ketoacyl ACP (β-ketoacyl ACP synthase), reduction of the keto-function to an alcohol (β-ketoacyl ACP reductase), dehydration to form enoyl-ACP (β-hydroxyacyl-ACP dehydrase) and finally reduction of the enoyl-ACP to form the elongated saturated acyl-ACP (enoyl-ACP reductase). β-ketoacyl ACP synthase I catalyzes elongation of the main saturated fatty acid in plants, palmitoyl-ACP (C16:0). Elongation of palmitoyl-ACP to stearoyl-ACP requires β-ketoacyl ACP synthase II (KAS II). Common plant unsaturated fatty acids are synthesized by desaturase. Desaturation of stearoyl-ACP by a soluble δ-9 desaturase form oleoyl-ACP (C18:1). Further desaturation takes place by action of membrane bound δ-12 desaturase to form linoleoyl-ACP (C18:2) and subsequently to α-linolenoyl-ACP by δ-15 desaturase.

The levels of particular fatty acids in plants are modulated by altering the expression of the genes involved in the biosynthesis of the fatty acids. Up-regulation or down-regulation of any of these genes potentially alters the production of particular fatty acids. Specifically, in one strategy, the relative or absolute quantities of C18 and/or unsaturated fatty acids are increased in a plant by the expression of a KAS II genetic sequence. In order to effect this expression, the plant is transformed with a vector such as pCBKASII-7, using the methods described in Example 7. Optionally, this is combined with the use of antisense nucleotide sequences directed to a palmitoyl-ACP thioesterase encoding genetic sequence, in order to reduce palmitic acid production and increase production of towards 18 carbon acyl chains. Manipulation of the stearoyl ACP desaturase gene can also be performed to reduce accumulation of stearic acid (C18:0) and direct metabolic flux toward the production of higher levels unsaturated acids such as oleic acid (C18:1).

In order to study the effects of KAS II expression, a model plant such as *A. thaliana* or a *Nicotiana* spp. is used to express KAS II. However, in order to produce large quantities of a C18 or unsaturated fatty acid, a plant from the Gramineae, Palmae, Juncaceae or Achenes familes is used, which specifically includes oil palm species from the genus *Elaeis*.

What is claimed is:

1. An isolated nucleic acid molecule comprising a sequence of nucleotides encoding a β-ketoacyl ACP synthase II from a plant, or a variant, derivative, homolog or analog of said β-ketoacyl ACP synthase II, wherein said variant, derivative, homolog or analog of said β-ketoacyl ACP synthase II has β-ketoacyl ACP synthase II activity, and wherein the sequence of nucleotides is set forth in SEQ ID NO: 2, or a nucleotide sequence having at least 95% identity to SEQ ID NO: 2 after optimal alignment.

2. The isolated nucleic acid of claim 1, further comprising a 3' untranslated region, said 3' untranslated region comprising the nucleotide sequence set forth in SEQ ID NO: 4.

3. The isolated nucleic acid of claim 1, wherein said plant is selected from the group consisting of the families Gramineae, Palmeae, Juncaceae and Achenes.

4. The isolated nucleic acid of claim 3, wherein said plant is from the Palmeae family.

5. The isolated nucleic acid of claim 4, wherein said plant is of the genus *Elaeis*.

6. The isolated nucleic acid of claim 5, wherein said plant is of the species *Elaeis guineensis* or *Elaeis oleifera*.

7. A vector comprising a nucleic acid molecule of claim 1.

8. The vector of claim 7, wherein the vector is a cloning vector.

9. The vector of claim 7, wherein the vector comprises a gene disruption construct.

10. The vector of claim 7, wherein the vector is an expression vector.

11. The vector of claim 7, wherein the vector is operable in a prokaryotic cell.

12. The vector of claim 11, wherein the prokaryotic cell is a bacterial cell.

13. The vector of claim 12, wherein the bacterial cell is an *E. coli* cell.

14. A genetically modified cell comprising the nucleic acid of claim 1.

15. The genetically modified cell of claim 14, wherein the cell is a prokaryotic cell.

16. The genetically modified cell of claim 15, wherein the prokaryotic cell is an *E. coli* cell.

* * * * *

SEQUENCE LISTING

<160> NUMBER OF SEQ ID NOS: 26

<210> SEQ ID NO 1
<211> LENGTH: 449
<212> TYPE: DNA
<213> ORGANISM: Elaeis guineensis

<400> SEQUENCE: 1

```
cattatgctg agtgatatct ttttttttg ccttgctcac aagttattgc cacatcctga      60
aggtagaggg gttatccttt gtattgaaaa tgcactagca gatgcaggag tagcaaagga     120
agacattaat tatgtaaatg cccatgcaac atcgacgcag atgggtgatt tgaaggaatt     180
tgaagctctc aaccgctgtt ttggtcagaa ccctcagctt agagtaaact caacaaagtc     240
aatgacgggt catctgctag gagctgcagg tggaatagaa gctgtggctg ctatacaagc     300
tataaggact ggttgggtcc acccaaatat caatttagac aacccggaga aaatgtgga     360
tgtcagcatt ctagtgggat cacaaaaaga gagatgtgat gtaaaggtgg cgttgtcgaa     420
ctcgttcgga ttcggtgggc ataactcaa                                       449
```

<210> SEQ ID NO 2
<211> LENGTH: 2228
<212> TYPE: DNA
<213> ORGANISM: Elaeis guineensis
<220> FEATURE:
<221> NAME/KEY: misc_feature
<222> LOCATION: (1)...(2228)
<223> OTHER INFORMATION: n = A,T,C or G

<400> SEQUENCE: 2

```
aaagctcgtg cctttttcttc cntaagatcg atgccatctt tcattccctt cgtcagcttt      60
tctcccctcc caaaaccttt cgccatcctc ttcgacccgt ttcctcctcc ccaaaatcgc     120
atattttctc gttaaaaatc gctctttttt ctctcgctgt ttcttagtcc gctctttgag     180
atcttgaatt cgcccttggc ctcttctcct ctctcaactt cgatcggaac gttctcgagt     240
tctagcttct gcccgctccg cttttggagc ttctctcctc ccttattccg gctttgctct     300
gttcttctcc aatggcgggc gccgccgtgg cctcgccgct gtgcacgtgg ctggtggcgg     360
cgtgcatgac ggtggcgtgc gacaaggagt ggccgctggg gccggggagt gcgtcccccc     420
ggcggaggtg gcggagggcg tcgctctccg gcggcgtggg ccgggcttcg ccgaggcggc     480
tgatctcggc cttctgtggg gcggggatcc aggggttgat gagctcgtgc ctggccttcg     540
agccctgcgc cgagttctac agctcgagaa atgggtcggc gttctttggg ggggatggct     600
tctctctgct tgggcggcag aatgctgaga ctactcgaag gcagcgaagg ggtgcccgtt     660
cttctccttc ttctgttgca ggaaaagtca tgtccattgc tgtgcagcct gaaaagaagg     720
ttgcagagaa agagagaacc caaaccaaac agcggagggt tgttgtgacg ggaatgggtg     780
tggtgactcc attaggccat gatccagatc atttctatga agagctcctc aagggtgtta     840
gtggcataag tgaaatagaa acattcgact gttccagtta tccaacgagg attgcaggag     900
aaattaaatc tttttcctcg gatggatggg tggcaccaaa actatccaaa aggatggaca     960
agtttatgct ttacttactt actgctggca agaaagcatt ggaaatggt ggacttacag    1020
aagaggctat gagttggttg ataaggaaa gatgtgagt tctcattggg tctgcaatgg    1080
gtggaatgaa agtttttaat gatgcaattg aggcttaag gatctcgtac aagaagatga    1140
accccttttg tgtacccttt gcaactacga atatgggctc tgcaatgctt gcaatggatc    1200
```

```
taggttggat gggcccaaac tattctattt ctactgcatg tgcaactagc aacttctgta    1260
ttttgaatgc agcaaaccat attataagag atgaagctga tgtgatgctt tgtggtggct    1320
ctgatgcagc aattatacca attggattgg ggggttttgt ggcatgcgga gcactctcgc    1380
agagaaatag tgatccgact aaagcgtcac ggccttggga cattgatcgt gatggattcg    1440
tgatggggga gggggctggc gtgcttctac tggaagaatt agagcatgct aagcaaagag    1500
gagcaaatat ctatgctgaa tttcttgggg aagcttcac atgtgatgct taccacatga    1560
ctgagccaca tcctgagggg gcaggcattg ctctttgcat tgagaacgca ttagcacaag    1620
caggggtagc caaagaagat gttaattatg taaatgctca tgcaacttca acacctgctg    1680
gtgacctaaa agagtatcaa gctctcattc gttgttttgg gcagaatcct gagctgagag    1740
tgaactctac aaaatcaatg attggtcacc tactaggagc ttctggtgcg gtggaagctg    1800
ttgctgcaat tcaggcaatt cgaacagggt gggtccatcc aaatgtcaat ctcgaaaacc    1860
cagaaaaaag tgtggatata aatgtgctgg tgggctcgaa aaaggaaaa ggttggacgt     1920 caataagctg gtgggctcaa agaaggaaag attggatgtg aaggtggccc tgtcaaactc    1980
ttttggcttt ggtggccaca actcgtctat cctgtttgca ccatacaaat aagcatcagc    2040
tatgggccta caaagcata agggcgaatt ccatcttaca tgtaatttgt atcagaaatg     2100
actgtgtggt gcttatgttt ttatttggca ccaacatctt gatcatatgg aattggtcta    2160
gatgccgtta tagctcataa tagaatggta tatagtgcac tactttcaaa aaaaaaaaa     2220 aactcagg                                                             2228

<210> SEQ ID NO 3
<211> LENGTH: 417
<212> TYPE: DNA
<213> ORGANISM: Elaeis guineensis

<400> SEQUENCE: 3
ccactacaag gtaaagaata aaaaagttgg tttaacttta atcaccttt tttctttccc      60 ctctttgcaa gttggcgatg ctttcgcca ctcccctggg tttcgccaaa gctcgtgcct     120
tttcttccta agatcgatgc catctttcat tcccttcgtc agcttttctc ccctcccaaa    180
acctttcgcc atcctcttcg acccgtttcc tccttcccaa aatcgcatat tttctcgtta    240
aaaatcgctc ttttttctct cgctgtttct tagtccgctc tttgagatct tgaatccctt    300
cttggcctct tctcctctct caacttcgat cggaacgttc tcgagttcta gcttctgccc    360
gctccgcttt tggagcttct ctcctcccct attccggctt tgctctgttc ttctcca       417

<210> SEQ ID NO 4
<211> LENGTH: 300
<212> TYPE: DNA
<213> ORGANISM: Elaeis guineensis

<400> SEQUENCE: 4
ataagctggt gggctcaaag aaggaaagat tggatgtgaa ggtggccctg tcaaactctt     60
ttggctttgg tggccacaac tcgtctatcc tgtttgcacc atacaaataa gcatcagcta    120
tgggcctaca aaagcatcaa ggtcatctta catgtaattt gtatcagaaa tgactgtgtg    180
gtgcttatgt ttttatttgg caccaacatc ttgatcatat ggaattggtc tagatgccgt    240
tatagctcat aatagaatgg tatatagtgc actactttca aaaaaaaaaa aaactcagg     300

<210> SEQ ID NO 5
```

```
<211> LENGTH: 854
<212> TYPE: DNA
<213> ORGANISM: Artificial Sequence
<220> FEATURE:
<223> OTHER INFORMATION: recombinant clone KasU86m

<400> SEQUENCE: 5
gcccttctct cgcagagaaa tagtgatccg actaaagcgt cacggccttg ggacattgat      60
cgtgatggat tcgtgatggg ggaggggggct ggcgtgcttc tactggaaga attagagcat    120
gctaagcaaa gaggagcaaa tatctatgct gaatttcttg ggggaagctt cacatgtgat    180
gcttaccaca tgactgagcc acatcctgag ggggcaggca ttgctctttg cattgagaac    240
gcattagcac aagcaggggt agccaaagaa gatgttaatt atgtaaatgc tcatgcaact    300
tcaacacctg ctggtgacct aaaagagtat caagctctca ttcgttgttt tgggcagaat    360
cctgagctga gagtgaactc tacaaaatca atgattggtc acctactagg agcttctggt    420
gcggtggaag ctgttgctgc aattcaggca attcgaacag gtgggtccca tccaaatgtc    480
aatctcgaaa acccagaaaa agtgtggat ataaatgtgc tggtgggctc gaaaaaagga    540
aaaggttgga tgtgataagc tggtgggctc aaagaaggaa agattggatg tgaaggtggc    600
cctgtcaaac tcttttggct ttggtggcca caactcgtct atcctgtttg caccatacaa    660
ataagcatca gctatgggcc tacaaaagca tcaaggtcat cttacatgta atttgtatca    720
gaaatgactg tgtggtgctt atgttttat ttggcaccaa catcttgatc atatggaatt    780
ggtctagatg ccgttatagc tcataataga atggtatata gtgcactact ttcaaaaaaa    840
aaaaaaaact cagg                                                       854

<210> SEQ ID NO 6
<211> LENGTH: 724
<212> TYPE: DNA
<213> ORGANISM: Artificial Sequence
<220> FEATURE:
<223> OTHER INFORMATION: recombinant clone KasU26RC

<400> SEQUENCE: 6
gcccttggac actgacatgg actgaaggag tagaaaattg caggagaaat taatttttt       60
tcaacagatg gattggtggc acctaaatta tctaaacgaa tggcaaattc atgctctatt    120
tacttattgc tggaaagaaa gcattagcca atggtggggt tattgaagag gtcatgagtc    180
agcttgacaa ggcaaaatgc ggagtgctca taggctctgc gatgggtgga atgaaggttt    240
ttaatgatgc catcgaagct ttaagggtct catataagaa gatgaatcca ttttgtgttc    300
catttgcaac gacaaacatg ggttctgcaa tccttgccat ggatctgggt tggatgggcc    360
caaattactc tatttcaact gcttgtgcta caagcaattt ctgtatcctg aatgcagcaa    420
accatataat aagaggggaa gcggatgtga tgctttgtgg tggatcagat gctgctatta    480
taccaattgg actggggggt tttgttgctt gcagagcact ctcgcagaga atagtgatc    540
cgactaaagc gtcacggcct tgggacattg atcgtgatgg attcgtgatg ggggagggggg    600
ctggcgtgct tctactggaa gaattagagc atgctaaggg cgaattcgtt taaacctgca    660
ggactagtcc cttagtgag ggttaattct gagcttggcg taggcaggtc aacgttttaa    720
cctc                                                                  724

<210> SEQ ID NO 7
<211> LENGTH: 923
<212> TYPE: DNA
<213> ORGANISM: Artificial Sequence
```

```
<220> FEATURE:
<223> OTHER INFORMATION: recombinant clone KasU11/12
<220> FEATURE:
<221> NAME/KEY: misc_feature
<222> LOCATION: (1)...(923)
<223> OTHER INFORMATION: n = A,T,C or G

<400> SEQUENCE: 7
cggcgtgaat tgtaatacga ctcactatag ggcgaattga atttagcggc cgcgaattcg      60
cccttggaca ctgacatggc tgaaggacta caaatcgtga cagggatggg tgtggtgact     120
ccactgggcg ttgatcctga tatcttctac aataaccttc ttgatggtgt cagtggtata     180
agtcaaattg aaacatttga ctgtaccaac tatccaacaa gaattgcagg agaaattaaa     240 tcttttttcaa cagatggatt ggtggcacct aaattatcta aacgaatgga caaattcatg     300
ctctatttac ttattgctgg aaagaaagca ttagccaatg gtggggttac tgaagaggtc     360
atgagtcagc ttgacaaggc aaaatgcgga gtgctcatag gctctgcgat gggtggaatg     420
aaggttttta atgatgccat cgaagcttta agggtctcat ataagaagat gaatccattt     480
tgtgttccat ttgcaacgac aaacatgggt tctgcaatcc ttgccatgga tctgggttgg     540
atgggcccaa attactctat ttcaactgct tgtgctacaa gcaatttctg tatcctgaat     600
gcagcaaacc atataataag aggggaagcg gatgtgatgc tttgtggtgg atcaaatgct     660
gcaagggcga attcctttaa acctgcagga ctagtcccct tagtgagggg taattcttga     720
ccttggcgta atcatcggc catagcctgg ttaccctgcg tccaaaatgg ttttccccct     780
accaaaattt ccctcaacat ttccaaaccc cggaaaccaa aaaggttgaa aaaccccngg     840 gggggggcctt aattgaagtg gaacctcact tcccaattta atttgccttt gcccctcact     900 tgccccttt ttcccaatcc ggg                                            923

<210> SEQ ID NO 8
<211> LENGTH: 1500
<212> TYPE: DNA
<213> ORGANISM: Artificial Sequence
<220> FEATURE:
<223> OTHER INFORMATION: recombinant clone KasU24a
<220> FEATURE:
<221> NAME/KEY: misc_feature
<222> LOCATION: (1)...(1500)
<223> OTHER INFORMATION: n = A,T,C or G

<400> SEQUENCE: 8
ccactcacaa ggctgtaaag aataaaaaag ttaggtttaa acttaaaatc accttttat       60 atctatatcc cctctttngc aagttggcga tggctttcgc cacgtcccct tggtttcgcc    120
aaagctcgtg ccttttcttc cgtaagatcg atgccatctt tcattccctt cgtcagcttt    180
tctcccctcc caaaaccttt cgccatcctc ttcgacccgt ttcctccttc ccaaaatcgc    240
atattttctc gttaaaaatc gctcttttt ctctcgctgt ttcttagtcc gctcttttgag    300 atcttgaatc ccttcttggc ctcttctcct ctctcaactt cgatcggaac gttctcgagt    360
tctagcttct gcccgctccg cttttggagc ttctctcctc ccttattccg gctttgctct    420
gttcttctcc aatggcgggc gccgccgtgg cctcgccgct gtgcacgtgg ctggtggcgg    480
cgtgcatgac ggtggcgtgc gacaaggagt ggccgctggg gccggggagt gcgtcccccc    540
ggcggaggtg gcggagggcg tcgctctccg gcgggcgtggg ccgggcttcg ccgaggcggc    600
tgatctcggc cttctgtggg gcgggatcc agggggttgat gagctcgtgc ctggccttcg    660
agccctgcgc cgagttctac agctcgagaa atgggtcggc gttctttggg ggggatggct    720
```

```
tctctctgct tgggcggcag aatgctgaga ctactcgaag gcagcgaagg ggtgcccgtt    780
cttctccttc ttctgttgca ggaaaagtca tgtccattgc tgtgcagcct gaaaagaagg    840
ttgcagagaa agagagaacc caaaccaaac agcggagggt tgttgtgacg ggaatgggtg    900
tggtgactcc attaggccat gatccagatc atttctatga agagctcctc aagggtgtta    960
gtggcataag tgaaatagaa acattcgact gttccagtta ccaacgagg  attgcaggag   1020 aaattaaatc tttttcctcg gatggatggg tggcaccaaa actatccaaa aggatggaca   1080
agtttatgct ttacttactt actgctggca agaaagcatt ggaaatggt  ggacttacag   1140 aagaggctat gagttggttg gataaggaaa gatgtgagt  tctcattggg tctgcaatgg   1200
gtggaatgaa agttttaat  gatgcaattg aggctttaag gatctcgtac aagaagatga   1260 acccctttg  tgtacccttt gcaactacga atatgggctc tgcaatgctt gcaatggatc   1320
taggttggat gggcccaaac tattctattt ctactgcatg tgcaactagc aacttctgta   1380
ttttgaatgc agcaaaccat attataagag atgaagctga tgtgatgctt tgtggtggct   1440
ctgatgcagc aattataccc attggattgg ggggttttgt ggcatgcgga gcactttcac   1500

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
gccacatcct gaaggtagag                                                20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
tgagttatgc ccaccgaatc                                                20

<210> SEQ ID NO 11
<211> LENGTH: 28
<212> TYPE: DNA
<213> ORGANISM: Artificial Sequence
<220> FEATURE:
<223> OTHER INFORMATION: synthetic primer

<400> SEQUENCE: 11
caccagatgg tgttgaagtt gcatgagc                                       28

<210> SEQ ID NO 12
<211> LENGTH: 28
<212> TYPE: DNA
<213> ORGANISM: Artificial Sequence
<220> FEATURE:
<223> OTHER INFORMATION: synthetic primer

<400> SEQUENCE: 12
cctgattctg ctagcgcctt ctcaatgc                                       28

<210> SEQ ID NO 13
<211> LENGTH: 42
<212> TYPE: DNA
<213> ORGANISM: Artificial Sequence
```

```
<220> FEATURE:
<223> OTHER INFORMATION: synthetic primer

<400> SEQUENCE: 13
ctctcgcaga gaaatagtga tccgactaaa gcgtcacggc ct                          42

<210> SEQ ID NO 14
<211> LENGTH: 38
<212> TYPE: DNA
<213> ORGANISM: Artificial Sequence
<220> FEATURE:
<223> OTHER INFORMATION: synthetic primer

<400> SEQUENCE: 14
gggctggcgt gcttctactg gaagaattag agcatgct                               38

<210> SEQ ID NO 15
<211> LENGTH: 37
<212> TYPE: DNA
<213> ORGANISM: Artificial Sequence
<220> FEATURE:
<223> OTHER INFORMATION: synthetic primer

<400> SEQUENCE: 15
tgtggctcag tcatgtggta agcatcacat gtgaagc                                37

<210> SEQ ID NO 16
<211> LENGTH: 38
<212> TYPE: DNA
<213> ORGANISM: Artificial Sequence
<220> FEATURE:
<223> OTHER INFORMATION: synthetic primer

<400> SEQUENCE: 16
agcatgctct aattcttcca gtagaagcac gccagccc                               38

<210> SEQ ID NO 17
<211> LENGTH: 40
<212> TYPE: DNA
<213> ORGANISM: Artificial Sequence
<220> FEATURE:
<223> OTHER INFORMATION: synthetic primer

<400> SEQUENCE: 17
gccgtgacgc tttagtcgga tcactatttc tctgcgagag                             40

<210> SEQ ID NO 18
<211> LENGTH: 30
<212> TYPE: DNA
<213> ORGANISM: Artificial Sequence
<220> FEATURE:
<223> OTHER INFORMATION: synthetic primer

<400> SEQUENCE: 18
gcagcatctg atccaccaca aagcatcaca                                        30

<210> SEQ ID NO 19
<211> LENGTH: 30
<212> TYPE: DNA
<213> ORGANISM: Artificial Sequence
<220> FEATURE:
<223> OTHER INFORMATION: synthetic primer

<400> SEQUENCE: 19
caacatccca ggggcgagaa gctttcactg                                        30
```

```
<210> SEQ ID NO 20
<211> LENGTH: 28
<212> TYPE: DNA
<213> ORGANISM: Artificial Sequence
<220> FEATURE:
<223> OTHER INFORMATION: synthetic primer

<400> SEQUENCE: 20
gtgaaagtgc tccgcatgcc acaaaacc                                              28

<210> SEQ ID NO 21
<211> LENGTH: 38
<212> TYPE: DNA
<213> ORGANISM: Artificial Sequence
<220> FEATURE:
<223> OTHER INFORMATION: synthetic primer

<400> SEQUENCE: 21
gggatgggtg tggtgactcc actgggcgtt gatcctga                                   38

<210> SEQ ID NO 22
<211> LENGTH: 27
<212> TYPE: DNA
<213> ORGANISM: Artificial Sequence
<220> FEATURE:
<223> OTHER INFORMATION: synthetic primer

<400> SEQUENCE: 22
atggacaagt ttatgcttta cttactt                                               27

<210> SEQ ID NO 23
<211> LENGTH: 27
<212> TYPE: DNA
<213> ORGANISM: Artificial Sequence
<220> FEATURE:
<223> OTHER INFORMATION: synthetic primer

<400> SEQUENCE: 23
atgcttttgt aggcccatag ctgatgc                                               27

<210> SEQ ID NO 24
<211> LENGTH: 26
<212> TYPE: DNA
<213> ORGANISM: Artificial Sequence
<220> FEATURE:
<223> OTHER INFORMATION: synthetic primer

<400> SEQUENCE: 24
ttccatatga tcaagatgtt ggtgcc                                                26

<210> SEQ ID NO 25
<211> LENGTH: 32
<212> TYPE: DNA
<213> ORGANISM: Artificial Sequence
<220> FEATURE:
<223> OTHER INFORMATION: synthetic primer

<400> SEQUENCE: 25
tgagatcgat gccatctctc attcccttcg tc                                         32

<210> SEQ ID NO 26
<211> LENGTH: 28
<212> TYPE: DNA
<213> ORGANISM: Artificial Sequence
```

```
<220> FEATURE:
<223> OTHER INFORMATION: synthetic primer

<400> SEQUENCE: 26
tcttggcctc ttctcctctc tcaacttc                                              28
```